(12) United States Patent
Westphal

(10) Patent No.: US 8,459,508 B2
(45) Date of Patent: Jun. 11, 2013

(54) SHROUD FOR A DISPENSER

(75) Inventor: Nathan R. Westphal, Union Grove, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 241 days.

(21) Appl. No.: 12/804,872

(22) Filed: Jul. 30, 2010

(65) Prior Publication Data

US 2012/0024902 A1  Feb. 2, 2012

(51) Int. Cl.
*B67D 7/06* (2010.01)
*B67D 7/78* (2010.01)
*B67D 7/84* (2010.01)
*B65D 83/00* (2006.01)

(52) U.S. Cl.
USPC ............... 222/183; 222/131; 222/402.13

(58) Field of Classification Search
USPC ............ 222/130, 131, 162, 182, 183, 394, 222/402.1, 402.13; 220/694, 699, 701, 915; 215/386, 390, 393, 395
See application file for complete search history.

(56) References Cited

U.S. PATENT DOCUMENTS

| | | | |
|---|---|---|---|
| 3,157,314 A | 11/1964 | Nadler | |
| 3,254,803 A | 6/1966 | Meshberg | |
| 3,272,391 A | 9/1966 | Meshberg | |
| 3,549,055 A | 12/1970 | Gatland | |
| 4,324,350 A | 4/1982 | Thompson | |
| 5,226,563 A | 7/1993 | Coggiola | |
| 5,358,147 A | 10/1994 | Adams et al. | |
| 5,377,869 A | 1/1995 | Weiss et al. | |
| D364,919 S | 12/1995 | Adams | |
| 5,487,489 A | 1/1996 | Weiss et al. | |
| 5,489,047 A | 2/1996 | Winder | |
| 5,507,733 A | 4/1996 | Larkin et al. | |
| 5,516,006 A | 5/1996 | Meshberg | |
| D390,941 S | 2/1998 | Cessaroni et al. | |
| D395,598 S | 6/1998 | Van Lit et al. | |
| 5,791,524 A * | 8/1998 | Demarest | 222/153.06 |
| 5,862,960 A | 1/1999 | Miller et al. | |
| 5,875,934 A | 3/1999 | Miller et al. | |
| D419,069 S | 1/2000 | Beck et al. | |
| 6,053,363 A | 4/2000 | Revenu | |
| D435,098 S | 12/2000 | Kemmis et al. | |
| D437,224 S | 2/2001 | Brozell | |
| D438,459 S | 3/2001 | Holthaus | |
| D447,949 S | 9/2001 | Richardson | |
| D447,953 S | 9/2001 | Brynestad et al. | |

(Continued)

FOREIGN PATENT DOCUMENTS

| | | |
|---|---|---|
| DE | 1491714 | 5/1969 |
| DE | 8612862 | 9/1986 |

(Continued)

OTHER PUBLICATIONS

PCT/US2010/002348 International Search Report dated Apr. 8, 2011.

(Continued)

*Primary Examiner* — Paul R Durand
*Assistant Examiner* — Vishal Pancholi

(57) ABSTRACT

A shroud includes a body portion having an opening adapted to receive one of at least two different containers. An upper portion of the body portion is adapted to interact with one of the at least two different containers.

29 Claims, 53 Drawing Sheets

U.S. PATENT DOCUMENTS

| | | | |
|---|---|---|---|
| 6,318,600 | B1 | 11/2001 | Winnett et al. |
| D451,763 | S | 12/2001 | McGuyer |
| 6,401,984 | B1 | 6/2002 | Jumel |
| 6,419,124 | B1 | 7/2002 | Hennemann et al. |
| D461,718 | S | 8/2002 | Brozell |
| 6,454,135 | B1 | 9/2002 | Brozell |
| D465,149 | S | 11/2002 | Bennett et al. |
| D465,152 | S | 11/2002 | Kaufman |
| D471,267 | S | 3/2003 | Ahn et al. |
| 6,569,387 | B1 | 5/2003 | Furner et al. |
| D476,235 | S | 6/2003 | Steinhoff |
| 6,592,011 | B1 | 7/2003 | Lammel et al. |
| 6,610,254 | B1 * | 8/2003 | Furner et al. ............. 422/123 |
| 6,644,305 | B2 | 11/2003 | MacRae et al. |
| D484,418 | S | 12/2003 | Diete |
| D491,255 | S | 6/2004 | Glucksman et al. |
| 6,745,760 | B2 | 6/2004 | Grychowski et al. |
| D493,257 | S | 7/2004 | McCorkindale |
| D493,576 | S | 7/2004 | Ward |
| 6,832,702 | B2 | 12/2004 | Garcia |
| D509,894 | S | 9/2005 | Hoyt et al. |
| D510,134 | S | 9/2005 | Lablaine |
| D510,135 | S | 9/2005 | Mariotti |
| D510,461 | S | 10/2005 | Vu |
| D511,568 | S | 11/2005 | Wheatley |
| D530,621 | S | 10/2006 | Rashid |
| D538,668 | S | 3/2007 | Campbell et al. |
| D538,915 | S | 3/2007 | Anderson et al. |
| D541,923 | S | 5/2007 | Castillo Higareda |
| D544,085 | S | 6/2007 | Schriner et al. |
| D547,189 | S | 7/2007 | Legros |
| D547,851 | S | 7/2007 | Anderson et al. |
| 7,303,553 | B2 | 12/2007 | Ott |
| 7,308,993 | B2 | 12/2007 | Mineau |
| D561,886 | S | 2/2008 | Furner et al. |
| D564,650 | S | 3/2008 | Hasik et al. |
| 7,353,971 | B2 | 4/2008 | Stradella |
| D570,233 | S | 6/2008 | Levinson et al. |
| D583,454 | S | 12/2008 | Kay et al. |
| D583,921 | S | 12/2008 | Kay et al. |
| D584,809 | S | 1/2009 | Porchia et al. |
| 7,552,728 | B2 | 6/2009 | Bonney et al. |
| D595,829 | S | 7/2009 | Drucker et al. |
| D596,432 | S | 7/2009 | Sarkar et al. |
| 7,614,526 | B2 | 11/2009 | Gaillen |
| D614,024 | S | 4/2010 | Eason et al. |
| D615,331 | S | 5/2010 | Meyerhoffer |
| D621,494 | S | 8/2010 | Li |
| D623,054 | S | 9/2010 | Eason et al. |
| D623,733 | S | 9/2010 | Busca et al. |
| D624,412 | S | 9/2010 | Jenkins |
| D624,426 | S | 9/2010 | Currington |
| D624,640 | S | 9/2010 | Kobayashi et al. |
| 7,798,370 | B2 | 9/2010 | Ciavarella et al. |
| D627,650 | S | 11/2010 | Yeung |
| D628,282 | S | 11/2010 | Espiritu, Jr. |
| D628,490 | S | 12/2010 | Sato et al. |
| D629,880 | S | 12/2010 | Hisey |
| 7,854,352 | B2 | 12/2010 | Davies et al. |
| D630,250 | S | 1/2011 | Yoon |
| D631,204 | S | 1/2011 | Dubitsky et al. |
| D632,211 | S | 2/2011 | Bradley et al. |
| D632,378 | S | 2/2011 | Deflorian et al. |
| 7,882,990 | B1 | 2/2011 | Walters et al. |
| 7,922,041 | B2 | 4/2011 | Gurrisi et al. |
| D644,313 | S | 8/2011 | Westphal |
| 8,061,562 | B2 | 11/2011 | Carpenter et al. |
| 8,079,498 | B2 | 12/2011 | Anderson et al. |
| 8,147,461 | B2 | 4/2012 | Bonney et al. |
| 2002/0074349 | A1 * | 6/2002 | Michaels et al. .......... 222/146.3 |
| 2002/0170928 | A1 * | 11/2002 | Grychowski et al. ........ 222/251 |
| 2005/0224525 | A1 | 10/2005 | Davies |
| 2006/0151536 | A1 | 7/2006 | Wong et al. |
| 2006/0211999 | A1 | 9/2006 | Fangrow |
| 2007/0131717 | A1 | 6/2007 | Davies et al. |
| 2007/0181609 | A1 | 8/2007 | Rymer |
| 2007/0241134 | A1 | 10/2007 | Gurrisi et al. |
| 2008/0054019 | A1 | 3/2008 | Stechschulte et al. |
| 2008/0061082 | A1 | 3/2008 | Anderson et al. |
| 2008/0116223 | A1 | 5/2008 | Stradella |
| 2008/0156896 | A1 | 7/2008 | Anderson et al. |
| 2010/0044609 | A1 | 2/2010 | Matsubara |
| 2010/0140298 | A1 | 6/2010 | Anderson et al. |

FOREIGN PATENT DOCUMENTS

| | | |
|---|---|---|
| DE | M9308146-0001 | 3/1994 |
| DE | M9705428-0001 | 11/1997 |
| DE | 49904597.1 | 9/1999 |
| DE | 40103188.8 | 7/2001 |
| DE | 40101915-0001 | 8/2001 |
| DE | 40301673-0001 | 9/2003 |
| DE | 40301673-0002 | 9/2003 |
| DE | 40501804-0001 | 9/2005 |
| DM | 047664 | 5/1999 |
| DM | 049719 | 10/1999 |
| DM | 057262 | 9/2001 |
| DM | 057578 | 9/2001 |
| DM | 064295 | 7/2003 |
| DM | 066461 | 3/2005 |
| DM | 067177 | 10/2005 |
| EM | 000040076-0003 | 12/2003 |
| EM | 000082425-0001 | 1/2004 |
| EM | 000227574-0001 | 11/2004 |
| EM | 001052286-0002 | 12/2008 |
| EM | 001105480-0001 | 3/2009 |
| EM | 001137947-0001 | 5/2009 |
| EM | 001149405-0001 | 9/2009 |
| EM | 001149405-0002 | 9/2009 |
| EM | 001606245-0001 | 9/2009 |
| EM | 001168314-0001 | 10/2009 |
| EM | 001621830-0001 | 10/2009 |
| EM | 001621830-0003 | 10/2009 |
| EM | 001621830-0007 | 10/2009 |
| EM | 001626821-0001 | 11/2009 |
| EP | 0743099 | 11/1996 |
| EP | 1076014 | 2/2001 |
| EP | 1386855 | 2/2004 |
| EP | 1997747 | 12/2008 |
| EP | 1848650 | 1/2009 |
| GB | 2025092 | 8/1992 |
| GB | 2025093 | 8/1992 |
| GB | 2034766 | 10/1993 |
| GB | 2042306 | 9/1994 |
| GB | 2075117 | 6/1998 |
| GB | 2076505 | 8/1998 |
| GB | 2095347 | 8/2000 |
| GB | 3006017 | 8/2002 |
| GB | 3008415 | 11/2002 |
| GB | 2443960 A | 5/2008 |
| WO | WO 96/08425 | 3/1996 |
| WO | 9838114 A1 | 3/1998 |
| WO | WO 00/01593 | 1/2000 |
| WO | 02096490 A2 | 5/2002 |
| WO | 03045819 A1 | 5/2003 |
| WO | WO 2005/044354 | 5/2005 |
| WO | WO 2005/087615 | 9/2005 |
| WO | 2006005615 A1 | 1/2006 |
| WO | WO 2006/005615 | 1/2006 |
| WO | WO 2006/005962 | 1/2006 |
| WO | 2006087514 A1 | 8/2006 |
| WO | WO 06/087515 | 8/2006 |
| WO | 2007062205 A2 | 5/2007 |
| WO | 2008059275 A2 | 5/2008 |
| WO | 2010110912 A1 | 9/2010 |

OTHER PUBLICATIONS

International Search Report, International Application No. PCT/US2010/002351, Apr. 7, 2011.

International Search Report, International Application No. PCT/US2010/002349, Apr. 12, 2011.

European Search Report, Application No. EP 09 15 6445, Jul. 7, 2009.

European Search Report, Application No. EP 09 17 4112, Dec. 11, 2009.

Non-final Office action mailed Oct. 22, 2012 for U.S. Appl. No. 12/804,849, 12 pages.

Final Office action mailed Jan. 30, 2012 for U.S. Appl. No. 12/804,849, 11 pages.

Non-final Office action mailed Aug. 7, 2012 for U.S. Appl. No. 12/804,859, 5 pages.

Final Office action mailed Jan. 3, 2013 for U.S. Appl. No. 12/804,859, 5 pages.

* cited by examiner

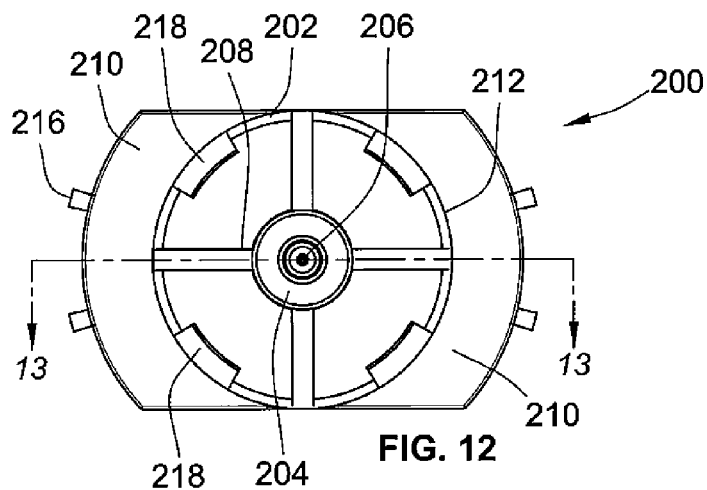
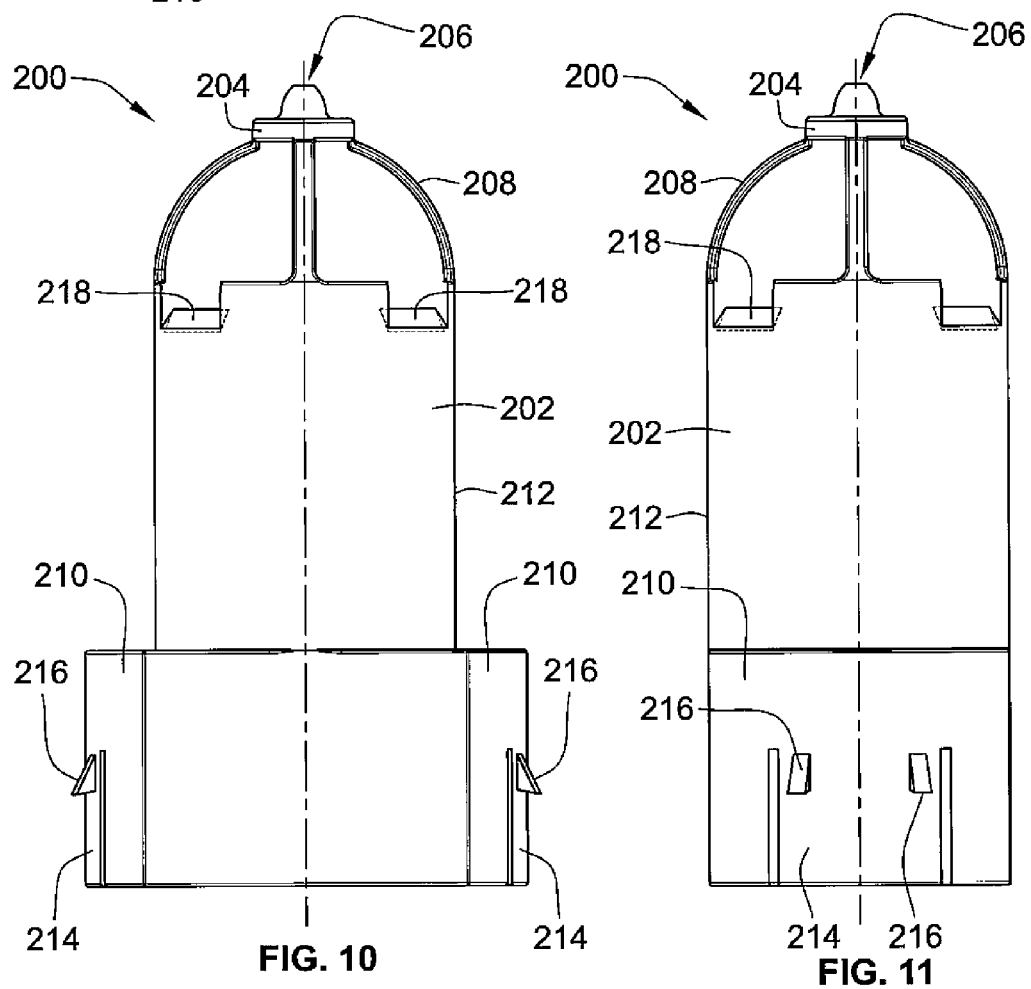

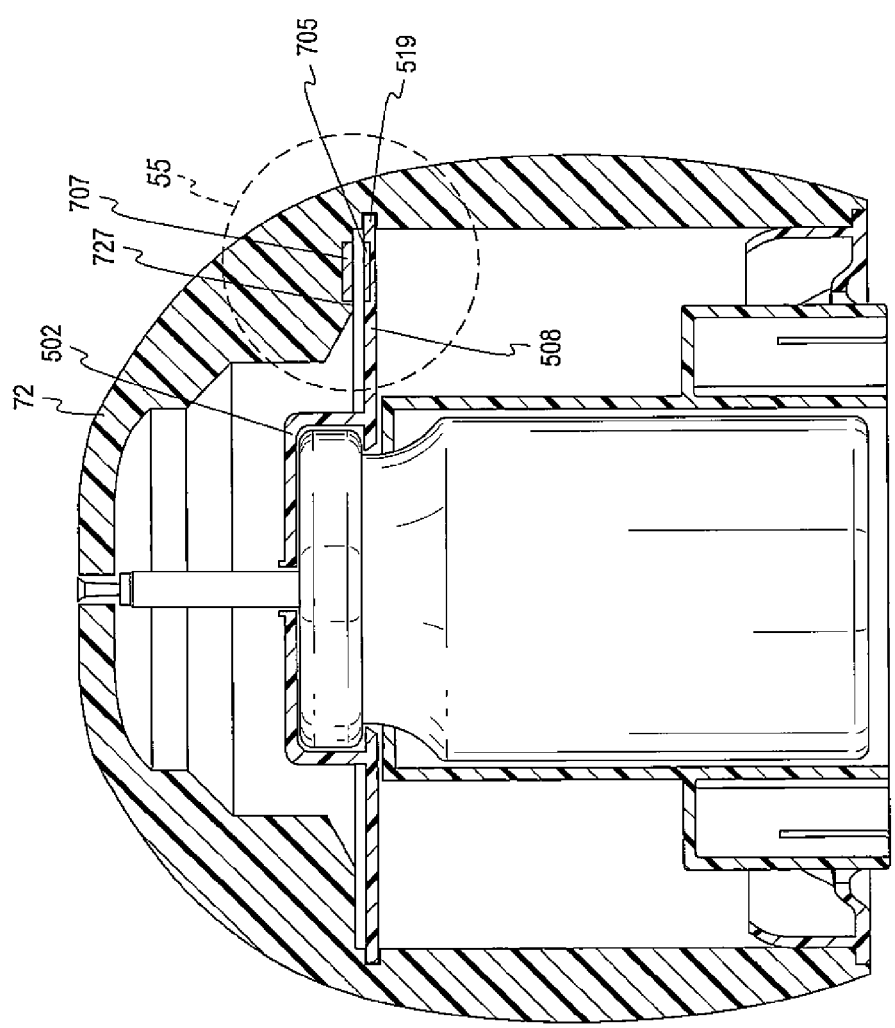
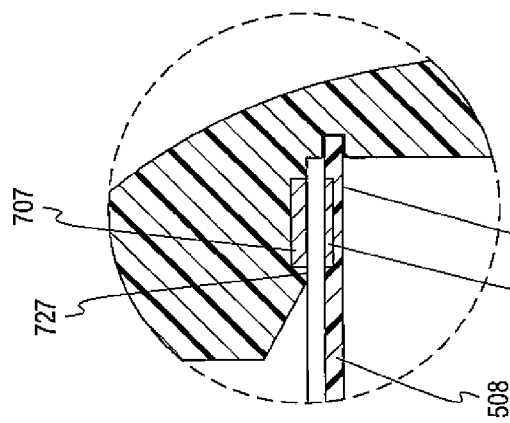
Fig. 54
Fig. 55

SHROUD FOR A DISPENSER

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure relates generally to a dispenser for the release of a volatile material from a container, and more particularly, to an ergonomic dispenser for the release of an aerosolized fluid from a container.

2. Description of the Background of the Invention

Aerosol containers are commonly used to store and dispense a variety of possible volatile materials such as air fresheners, deodorants, insecticides, germicides, decongestants, perfumes, and the like. The volatile material is stored under compression and a release valve on the aerosol container controls release of the volatile material. The release valve is activated by actuation of a valve stem through which the volatile material flows. However, aerosol containers typically include unwieldy canisters that are not ergonomically fashioned for ease of use and that appear intrusive in many home or work environments. The present disclosure provides an aerosol dispenser for housing an aerosol container in an ergonomically actuable housing, which appears like a naturally occurring object or includes naturally occurring elements in its construction. Further, such ergonomically actuable housings may be used in conjunction with any type of container having a compressed or compressible fluid, e.g., containers having a pump-type sprayer or containers that include a compressed or LPG, to name a few. It is contemplated that the present disclosure in connection with aerosol containers may be modified as known to one of skill in the art to be inclusive of these other types of containers.

SUMMARY OF THE INVENTION

According to one aspect of the invention, a shroud comprises a body portion having an opening adapted to receive one of at least two different containers. An upper portion of the body portion is adapted to interact with one of the at least two different containers.

According to another aspect of the invention, a shroud comprises a body portion having an upper portion truncated by a plurality of notches, wherein first and third opposing towers are provided having a first height and second and fourth opposing towers are provided having a second height less than the first height. A skirt extends downwardly and outwardly from the body portion. An opening extends through the body portion and the skirt adapted to receive a container.

BRIEF DESCRIPTION OF THE DRAWINGS

FIG. 10 is a side elevational view of a first embodiment of a shroud for use with the aerosol dispenser of FIG. 1;

FIG. 11 is another side elevational view of the shroud of FIG. 10;

FIG. 12 is a top plan view of the shroud of FIG. 10;

FIG. 54 is a partial sectional view of a different embodiment of an engagement mechanism including a housing having a container with a shroud disposed therein and another embodiment of an electrical system;

FIG. 55 is an enlarged sectional view of the electrical system of FIG. 54;

Other aspects and advantages of the present invention will become apparent upon consideration of the following detailed description, wherein similar structures have similar reference numerals.

DETAILED DESCRIPTION

Figure 1:
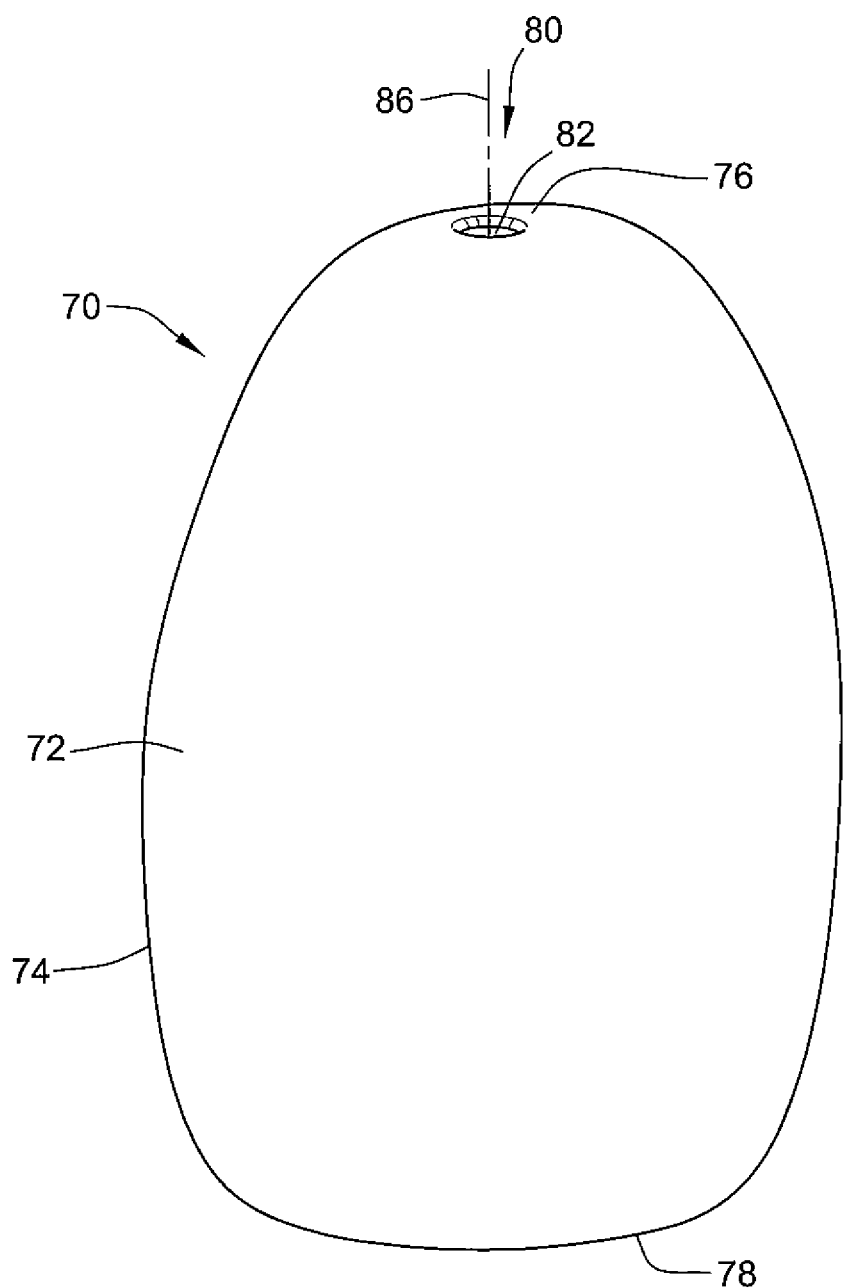
FIG. 1 is a top, front, and left side isometric view of a first embodiment of an aerosol dispenser.
Figure 2:
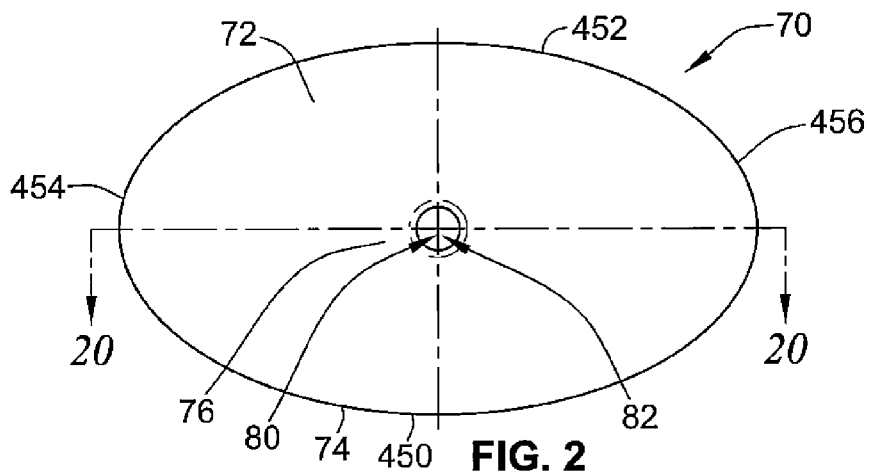
FIG. 2 is a top plan view of the aerosol dispenser of FIG. 1.
Figure 3:
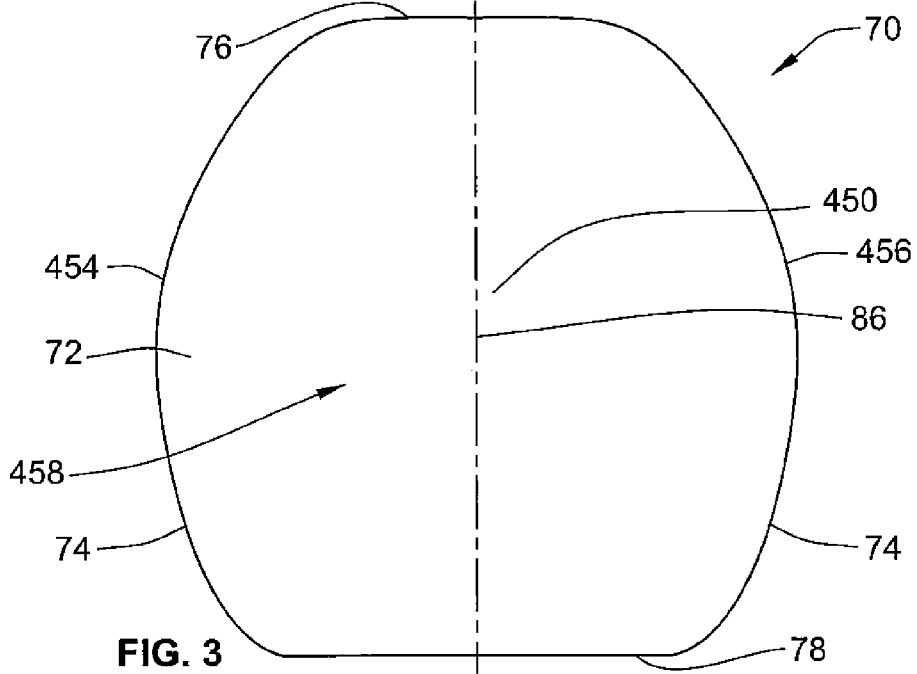
FIG. 3 is a side elevational view of the aerosol dispenser of FIG. 1.
Figure 4:
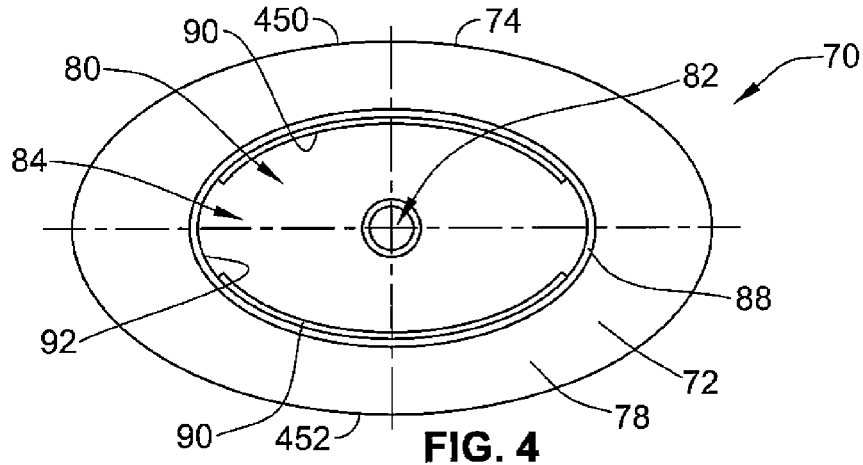
FIG. 4 is a bottom elevational view of the aerosol dispenser of FIG. 1.

A first embodiment of an aerosol dispenser 70 is depicted in FIGS. 1-4. The aerosol dispenser 70 includes a housing 72 having smooth or textured curvilinear sides 74 between a top end 76 and a bottom end 78. A bore 80 extends longitudinally through the housing 72 and includes a first aperture 82 at the top end 76 thereof and a second aperture 84 at the bottom end 78 thereof. The first and second apertures 82, 84 are each centered along a longitudinal axis 86 of the housing 72. As shown in FIG. 4, a groove 88 extends around a periphery of the second aperture 84. Two opposing lips 90 extend interiorly from a surface 92 of the housing 72 adjacent the groove 88.

A second embodiment of an aerosol dispenser 71 is shown in FIGS. 5-8. The aerosol dispenser 71 is similar to the first embodiment of the aerosol dispenser 70, except for the differences noted herein. A plurality of vertical elongate ribs 73 is disposed on an interior surface 75 of a housing 77. The housing 77 further includes two curvilinear protrusions 79 that circumscribe a portion of the inner surface 75 of the housing 77 and extend outwardly therefrom adjacent the second aperture 84. Opposing grooves 83 circumscribe a portion of the second aperture 84 beneath the two curvilinear protrusions 79.

Figure 9:
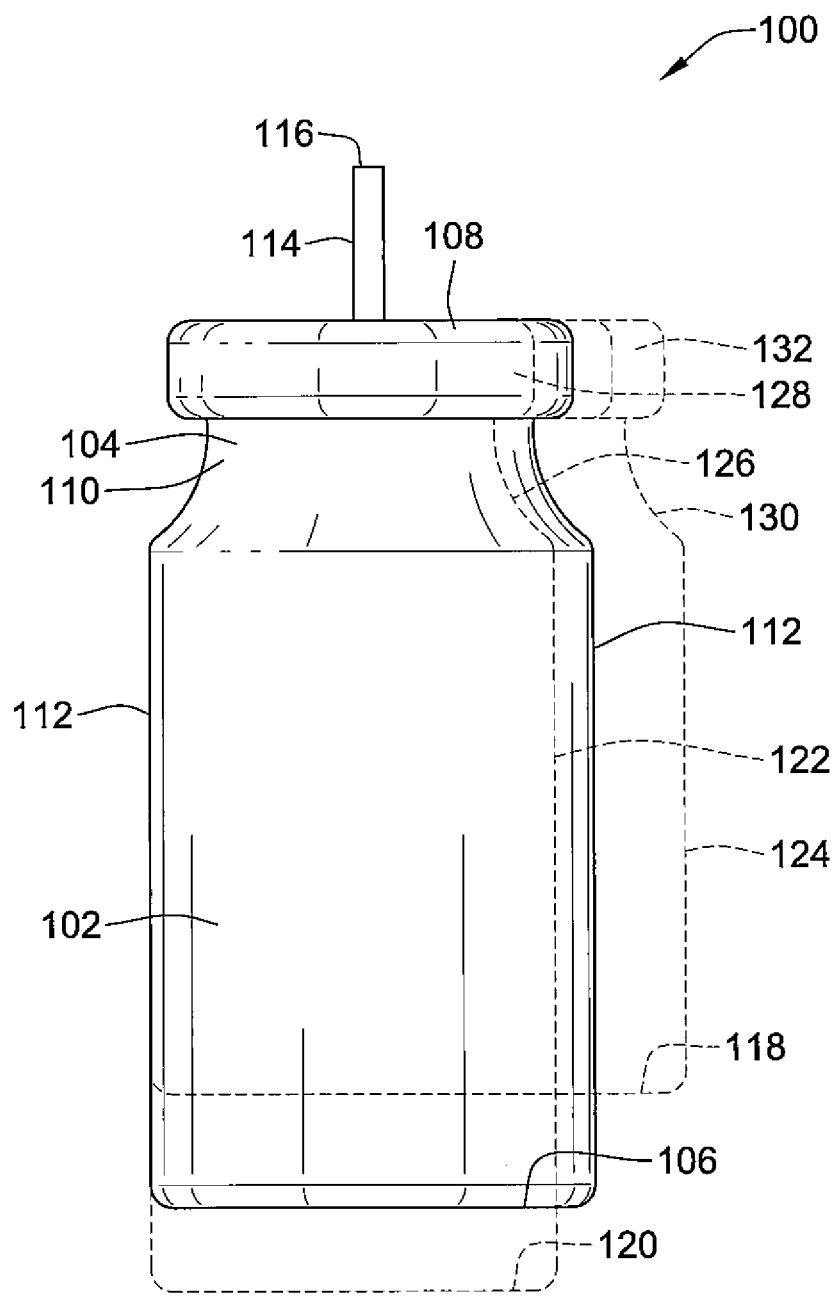
FIG. 9 is a side elevational view of an aerosol container, with alternative embodiments of the aerosol container shown in dashed lines.
Figure 13:
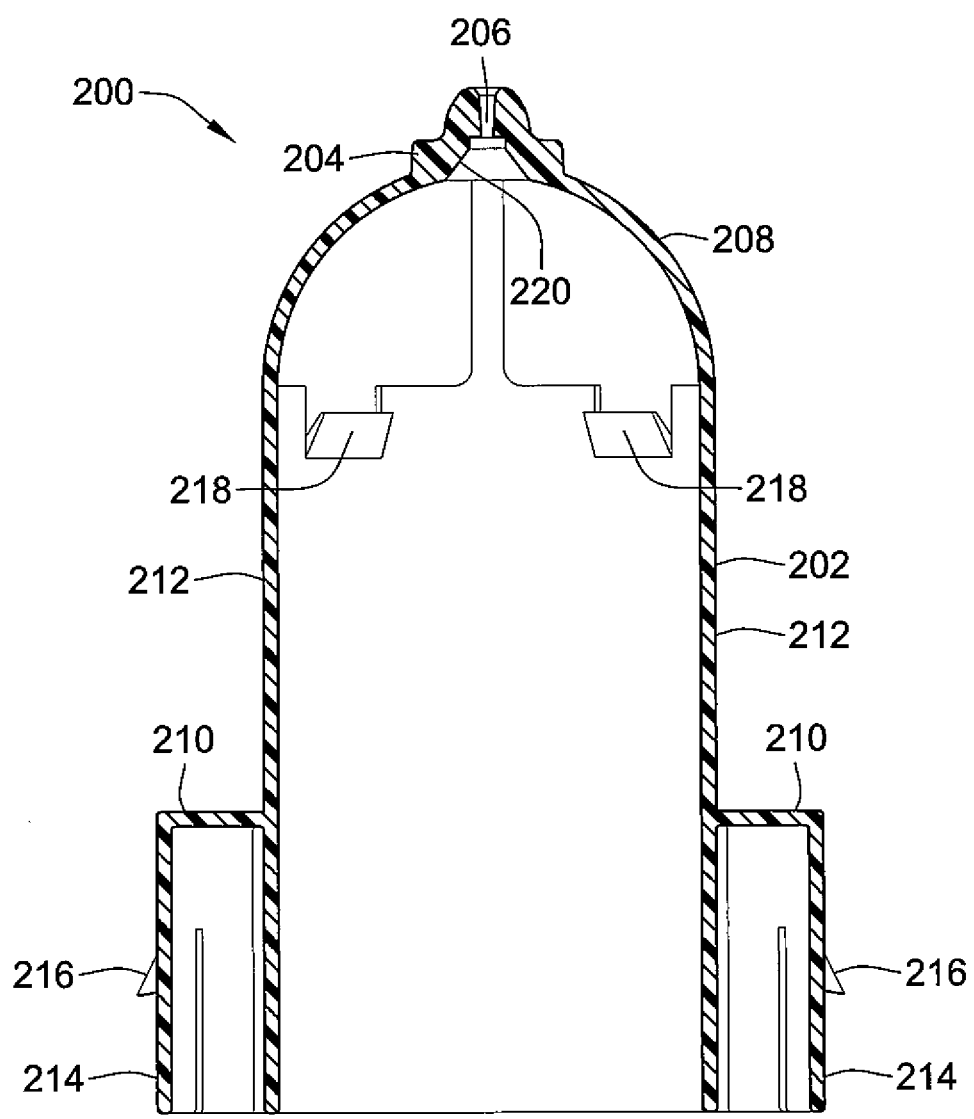
FIG. 13 is a sectional view of the shroud of FIG. 10 taken along the line 13-13 of FIG. 12.

Aerosol containers, such as the aerosol container 100 depicted in FIG. 9, are well known to those skilled in the art. The aerosol container 100 comprises a body 102 with a top end 104 and a bottom end 106. A mounting cup 108 is disposed above a neck 110 of the aerosol container 100. The body 102 is generally cylindrical in geometry and includes a wall 112. A valve assembly (not shown) within an upper portion of the aerosol container 100 includes a valve stem 114 that extends through the mounting cup 108. The valve stem 114 is a cylindrical tube having a passage 115 (see FIG. 14) disposed longitudinally therethrough. A distal end 116 of the valve stem 114 extends upwardly and away from the mounting cup 108 and a proximal end (not shown) is disposed within the valve assembly. The mounting cup 108 may optionally include a peripheral flange (not shown) that extends radially outwardly from a periphery of the mounting cup 108. The peripheral flange may be a part of the mounting cup 108 or may be an annular cap (not shown), which attaches over the mounting cup 108 such that the flange extends radially outwardly therefrom.

Axial compression, i.e., downward movement, of the valve stem 114 opens the valve assembly, which allows a pressure difference between an interior of the aerosol container 100 and the atmosphere to force the contents of the aerosol container 100 out through the distal end 116 of the valve stem 114. It is also contemplated that the aerosol container 100 could utilize a tilt activated valve stem with minimal or no modifications to the structure disclosed hereinafter. Further, in other embodiments a container 100 having a metered valve pump sprayer is used in lieu of an aerosol container to hold and dispense the volatile material. Indeed, it is contemplated that any type of non-aerosol container may be used in conjunction with the dispensers disclosed herein. For example, other containers may include a differing pump-type sprayer, a compressed gas, LPG, or any other compressible or compressed fluid, as would be known to one of skill in the art. The present disclosure with respect to aerosol containers should therefore be considered inclusive of these other types of non-aerosol containers.

Referring again to FIG. 9, the aerosol container 100 may have one of a multiplicity of diameters and/or lengths. For example, using the solid lines in FIG. 9 as a basis for comparison, the aerosol container 100 may have a length that is shorter or longer than the basis as illustrated by the dashed lines 118 and 120, respectively. Similarly, the aerosol container 100 may have a width that is narrower or wider than the basis as illustrated by the dashed lines 122 and 124, respectively. The aerosol container 100 having the narrower width 122 would also have a correspondingly narrower neck 126 and mounting cup 128. Similarly, the container 100 having the wider width 124 would also have a correspondingly wider neck 130 and mounting cup 132.

The aerosol dispenser 70 includes structure that can accommodate aerosol containers having a multiplicity of widths and lengths. An element of this structure is a first embodiment of a shroud 200, illustrated in FIGS. 10-13. The shroud 200 includes a body portion 202 flexibly attached to an actuator socket 204. The actuator socket 204 includes a passage 206 extending therethrough. The actuator socket 204 is attached to the body portion 202 by flexible members 208. The flexible members 208 allow one or both of the actuator socket 204 and the body portion 202 to be displaced toward one another. A bottom end of the shroud 200 includes shoulders 210 extending from an exterior surface 212 of the shroud 200. Each shoulder 210 includes a flexible arm 214 that has at least one tapered protrusion 216 extending outwardly therefrom. The protrusions 216 are adapted to engage a support member on an interior surface of an adapter, as discussed in greater detail below.

Figure 14:
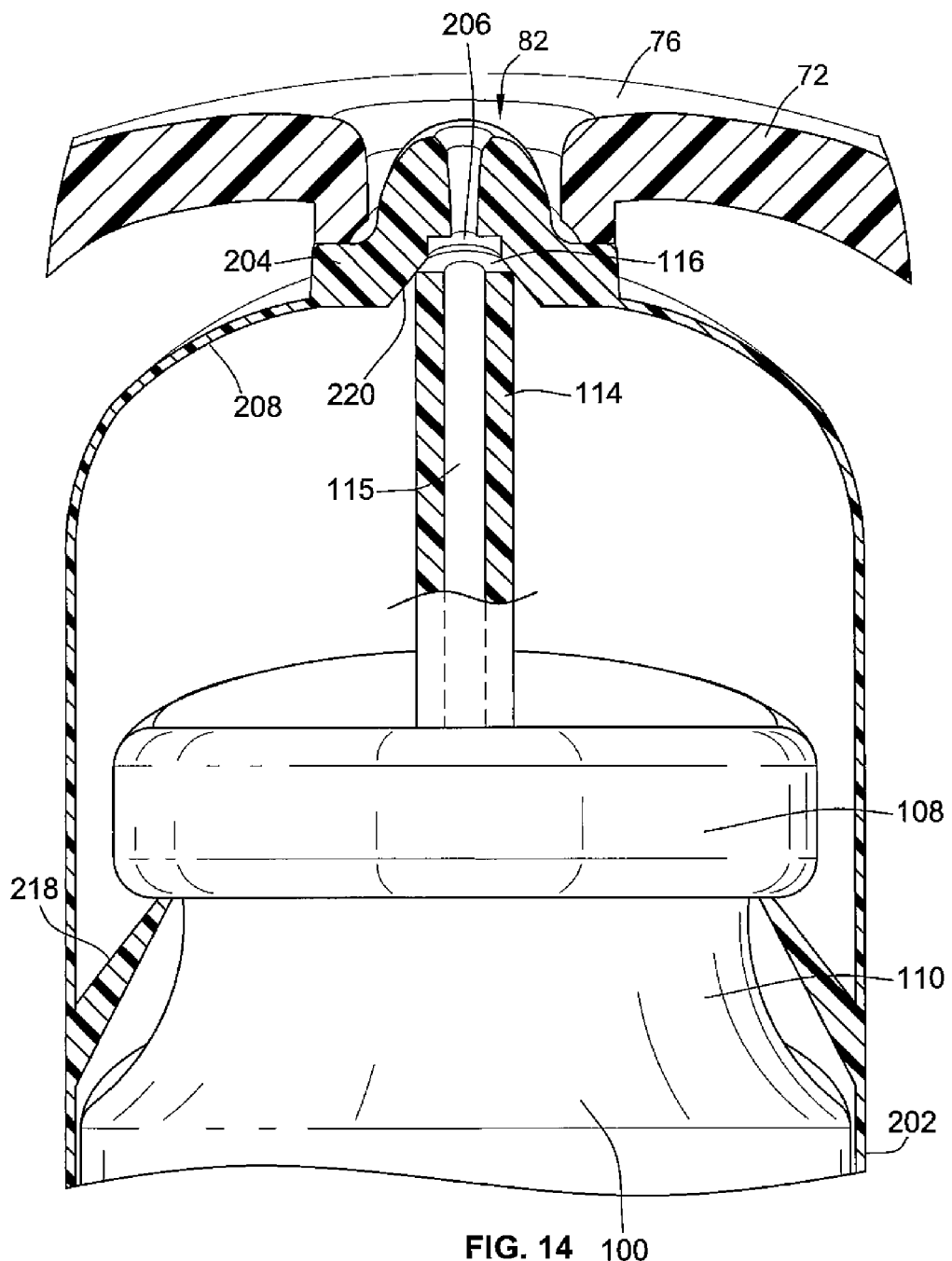
FIG. 14 is an enlarged, partial sectional view of the aerosol dispenser of FIG. 1 in combination with the shroud of FIG. 10 and the aerosol container of FIG. 9.

The shroud 200 is adapted to receive the aerosol container 100 therein such that the valve stem 114 of the aerosol container 100 is disposed within the actuator socket 204, as illustrated in FIG. 14. Referring to FIGS. 10-13, the shroud 200 includes flexible internal shoulders 218 that snap over the mounting cup 108 on the aerosol container 100. In use, the internal shoulders 218 fixedly hold the aerosol container 100 with respect to the body portion 202 of the shroud 200. An inlet 220 of the actuator socket 204 is sized to accommodate the valve stem 114 of the aerosol container 100. With the aerosol container 100 thus installed within the shroud 200, the valve stem 114 is in contact with the actuator socket 204. However, in the present rest state the valve stem 114 is not contacted to a degree sufficient to open the valve assembly within the aerosol container 100.

Turning to FIGS. 15-19, a second embodiment of an aerosol dispenser 230 (see FIG. 19) is shown. The aerosol dispenser 230 includes a shroud 250 (see FIG. 15). The shroud 250 is substantially similar to the shroud 200 discussed hereinabove with respect to FIGS. 10-13, except that the shroud 250 lacks the actuator socket 204 and the flexible members 208. In addition, the shroud 250 may have one or more support elements (not shown) running vertically, i.e., parallel to a longitudinal axis of the shroud 250, on the exterior surface 212 thereof, wherein each support element extends from one of the internal shoulders 218 toward the shoulders 210 or bottom end of the shroud 250. The support elements are sized to provide clearance within the bore 80 to allow for easy insertion therein and removal therefrom and to provide support to the internal shoulders 218 of the shroud 250, which abut the mounting cup 108 or collar of the container 100. Further, the support elements may be any shape, e.g., circular, triangular, etc.

Figure 16:
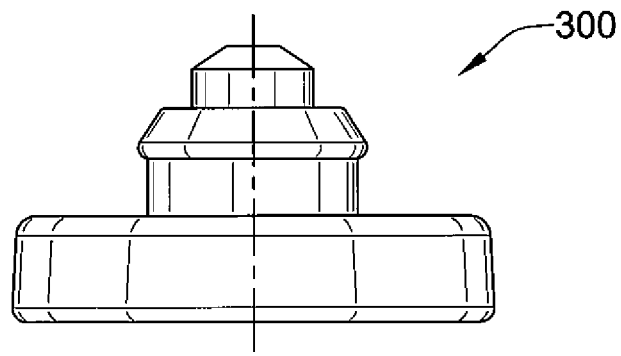
FIG. 16 is a side elevational view of an actuator socket.
Figure 17:
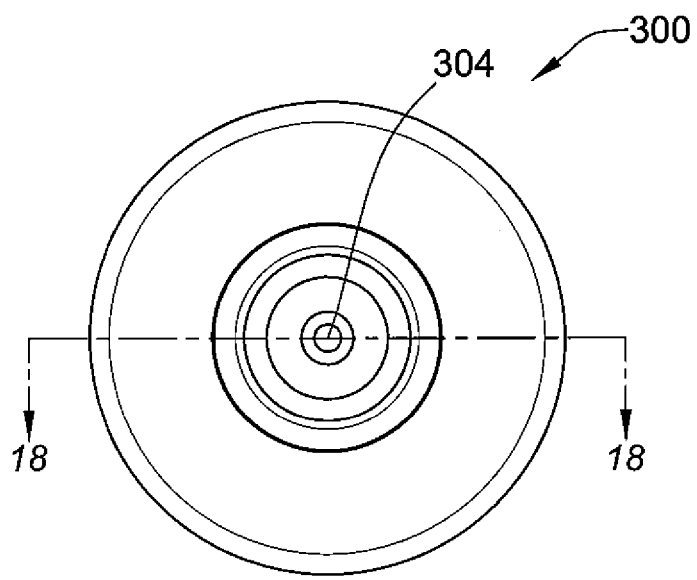
FIG. 17 is a top plan view of the actuator socket of FIG. 16.
Figure 18:
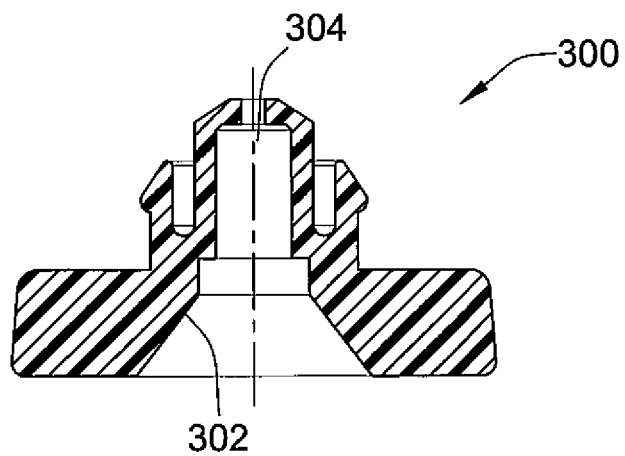
FIG. 18 is a side elevational, partial sectional view of the actuator socket of FIG. 16 taken along the line 18-18 of FIG. 17.

The shroud 250 is utilized in conjunction with an actuator socket 300, which is illustrated in FIGS. 16-18. The actuator socket 300 includes a frusto-conical inlet portion 302 and a passage 304 extending therethrough. The frusto-conical inlet portion 302 is adapted to receive any of a plurality of valve stems of an aerosol container having a uniformly cylindrical cross-section or a non-uniform cylindrical cross-section. The actuator socket 300 fits within the first aperture 82 of the housing 72 and is held therein by, for example, a press fit, a snap fit, an adhesive, or any other securing means. In a different embodiment, the actuator socket 300 is integral with a portion of the housing 72. Once thus disposed in the first aperture 82, the actuator socket 300 and the shroud 250 hold the aerosol container 100 therebetween with the valve stem 114 in contact with the actuator socket 300.

It is also contemplated that the shroud 200 could be utilized in conjunction with the actuator socket 300. In such an embodiment, illustrated as aerosol dispenser 230' in FIG. 20, passages 206 and 304, which extend through the actuator sockets 204 and 300, respectively, are guided into alignment and fluid communication by the frusto-conical inlet portion 302. This is made possible by the ability of the inlet portion 302 to receive the bulbous end of the actuator socket 204, which has a non-uniform cylindrical cross-section. An intermediate chamber 306 is formed between the passages 206 and 304. The intermediate chamber 306 may provide a disruption to a flow of the fluid dispensed from the aerosol container 100 to promote mixing and atomization thereof before release to the environment.

Figure 21:
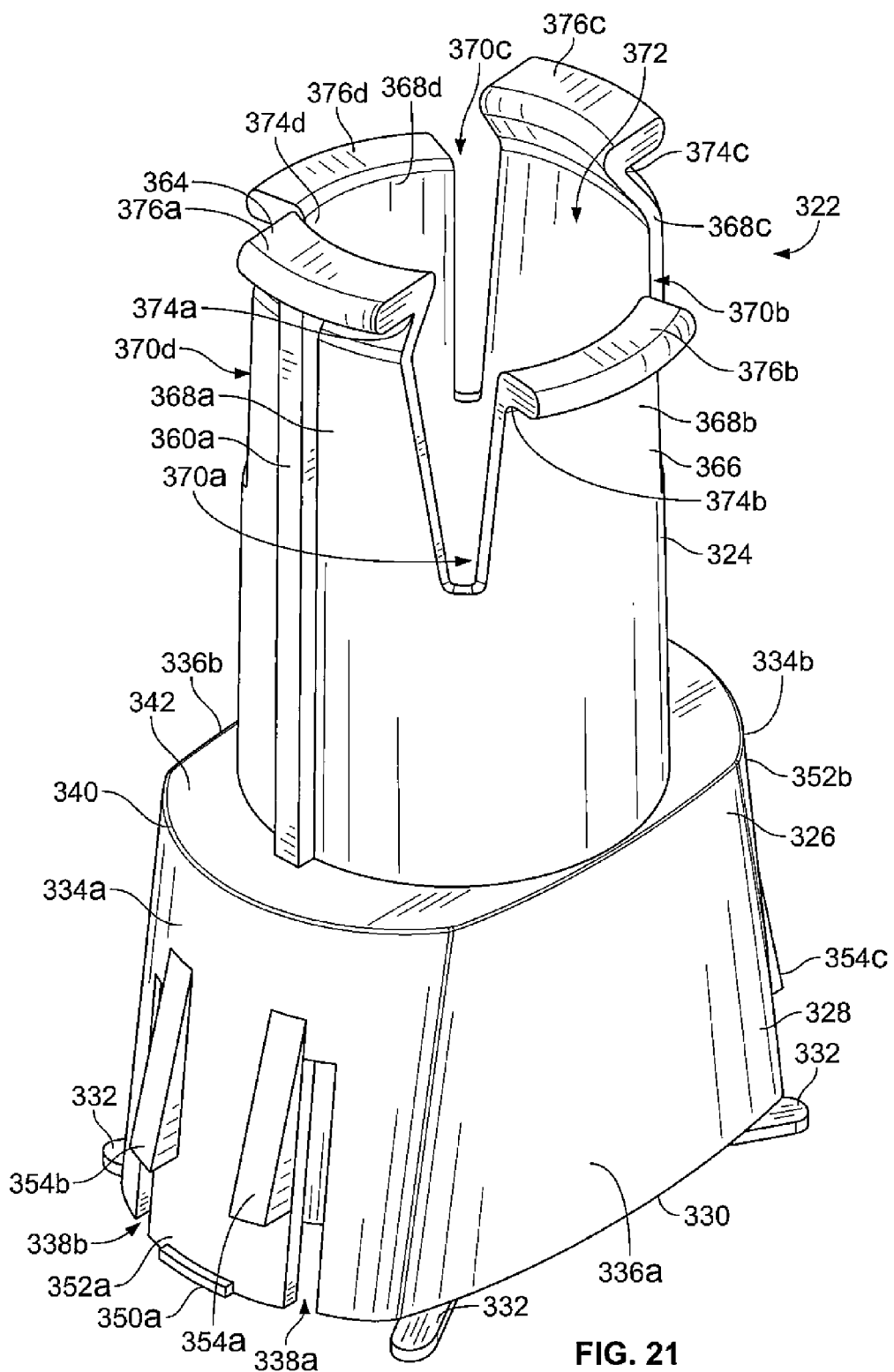
FIG. 21 is an isometric view of a third embodiment of a shroud.
Figure 22:
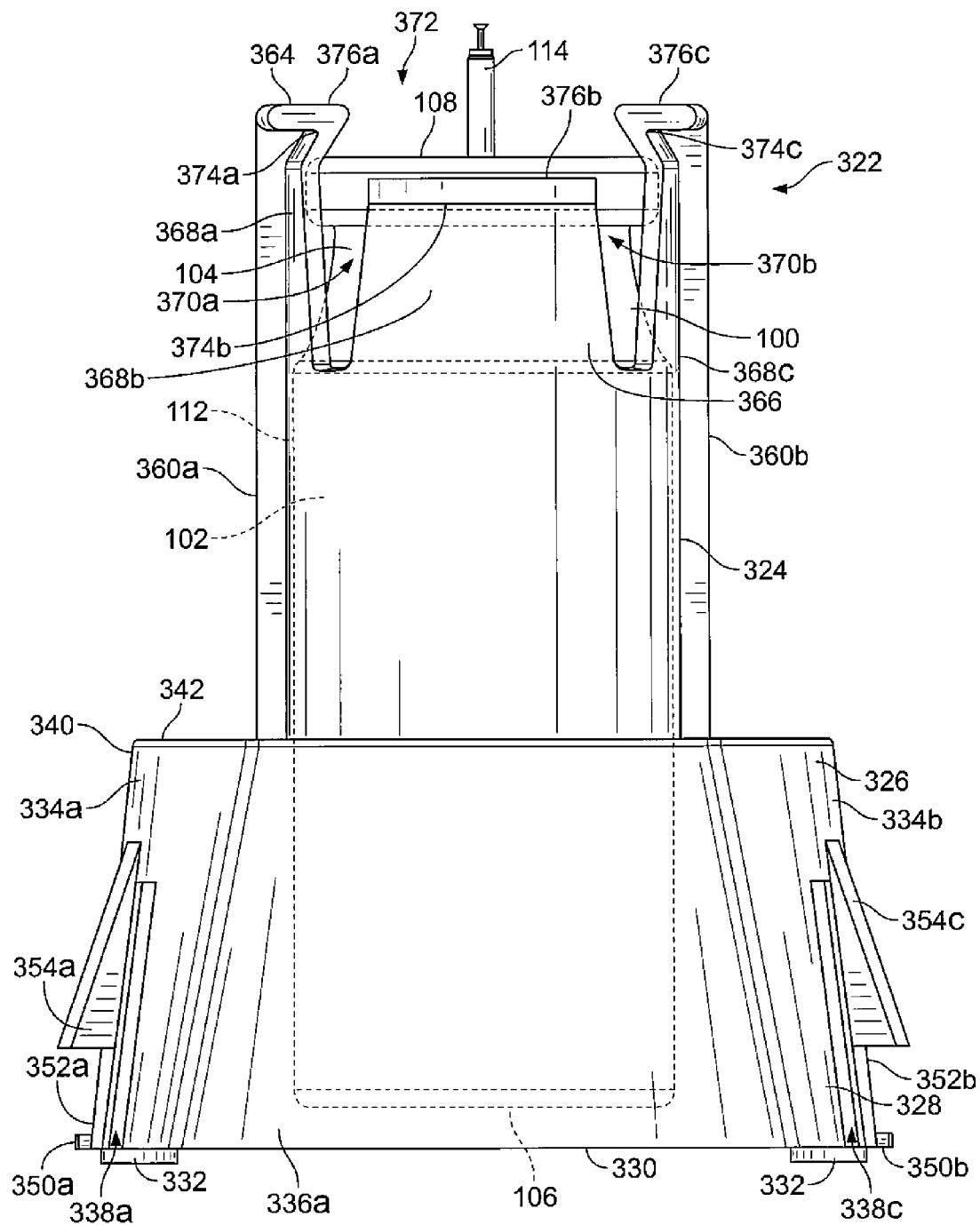
FIG. 22 is a side elevational view of the shroud of FIG. 21 in combination with the aerosol container of FIG. 9 in a pre-operative state.
Figure 22A:
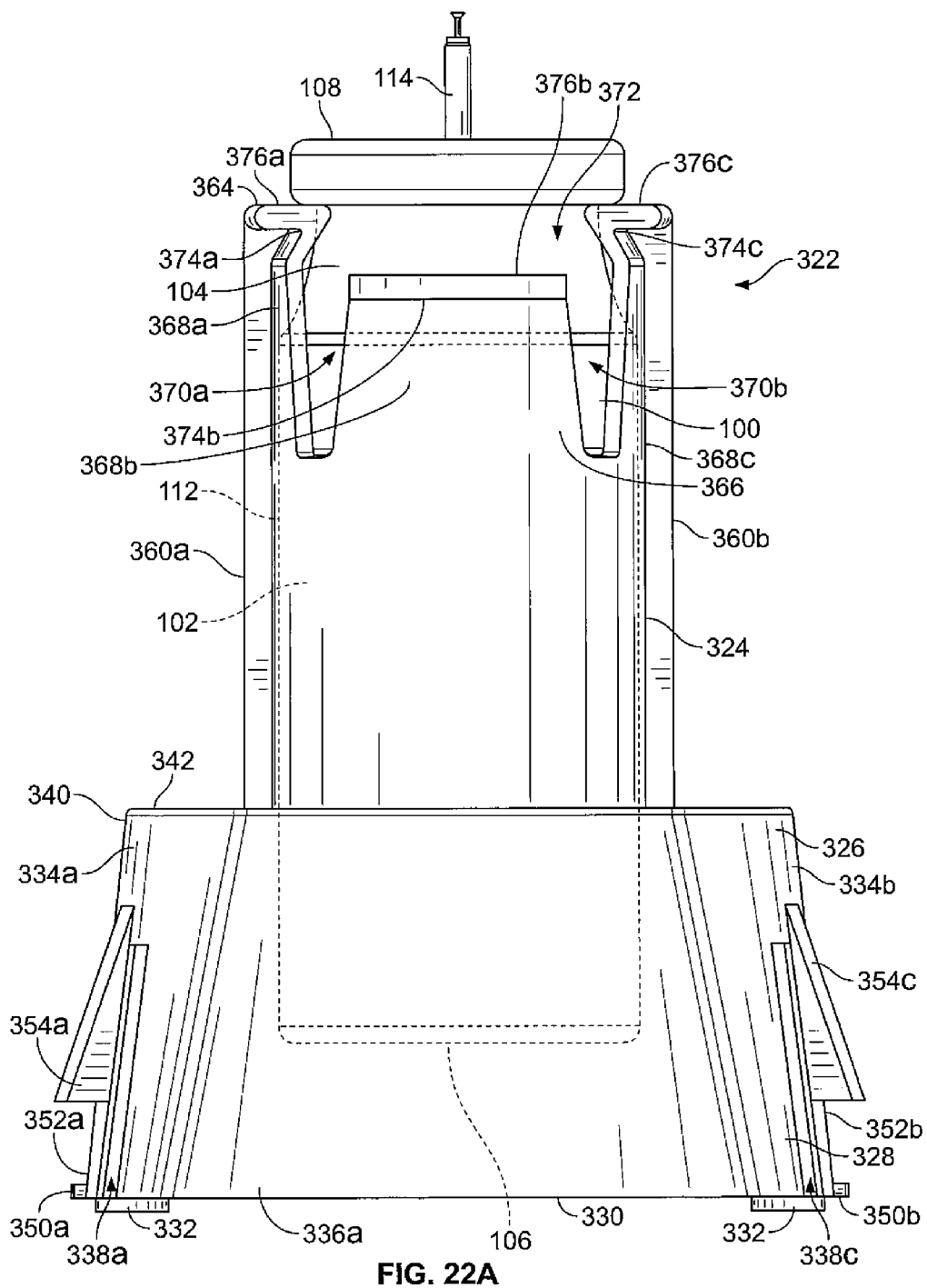
FIG. 22A is view of the shroud and the container of FIG. 22 in an operative state.

FIGS. 21, 22, and 22A depict a third embodiment of a shroud 322 adapted to be used with any of the aerosol dispensers as discussed previously herein. For purposes of the present discussion, the shroud 322 will be described in connection with the housing 77 depicted in FIGS. 5-8 and the container 100 shown in FIG. 9. The shroud 322 includes a cylindrical body portion 324 having a racetrack shaped skirt 326 that extends downwardly and outwardly therefrom. The skirt 326 is defined by a sidewall 328 having a bottom edge 330. A plurality of oval-shaped tabs 332 extend outwardly from the bottom edge 330. The tabs 332 are disposed adjacent corners of the skirt 326 and extend outwardly at an angle with respect to the bottom edge 330. The tabs 332 are adapted to catch on a bottom edge of an adapter 400 as discussed in more detail hereinbelow to prevent over insertion of the shroud 322 into the housing 72, 77. Although four tabs 332 are shown, any number of tabs having a variety of shapes may be used.

The sidewall 328 of the skirt 326 includes opposing first and second ends 334a, 334b connected to one another by opposing first and second medial portions 336a, 336b. The first end 334a is truncated by two elongate vertical openings 338a, 338b and the second end is similarly truncated by elongate vertical openings 338c, 338d (338d not shown). The elongate vertical openings 338a-d extend upwardly from the bottom edge 330 toward a top ridge 340 of the sidewall 328. A flat surface 342 extends inwardly from the top ridge 340 toward the cylindrical body 324.

Still referring to FIGS. 21, 22, and 22A, first and second ridges 350a, 350b, extend outwardly from the bottom edge 330 of opposing first and second finger tabs 352a, 352b. The first and second ridges 350a, 350b provide a gripping surface to assist a user in grasping and squeezing the resilient first and second finger tabs 352a, 352b. The shroud 322 further includes a plurality of tapered protrusions 354a, 354b, 354c, 354d (354d not shown) extending outwardly from the first and second finger tabs 352a, 352b. The protrusions 354a-d are similar to the protrusions 216 discussed above in connection with FIGS. 10-15.

Now turning to the top portion of the shroud 322, two opposing elongate support elements 360a, 360b extend upwardly from opposing sides of the flat surface 342 along the cylindrical body 324. The support elements 360a, 360b extend the length of the body 324 until terminating at an area adjacent a top edge 364 of the body 324. In other embodiments, one or more of the support elements could be imparted with a different shape, such as a curved or triangular arrangement. Indeed, the exact shape of the support elements is not essential to the present disclosure of any of the embodiments herein and may be readily modified. A top portion 366 of the body 324 is divided into four towers 368a, 368b, 368c, 368d by way of v-shaped notches 370a, 370b, 370c, 370d. The towers 368a-d surround a central opening 372 that extends though the cylindrical body 324 and the skirt 326. The second and fourth towers 368b, 368d are disposed on opposing sides of the opening 372 and are shorter in height than the first and third towers 368a, 368c. Each tower 368a-d includes an angled portion 374a, 374b, 374c, 374d disposed below substantially flat terminal portions 376a, 376b, 376c, 376d, respectively.

Figure 33:
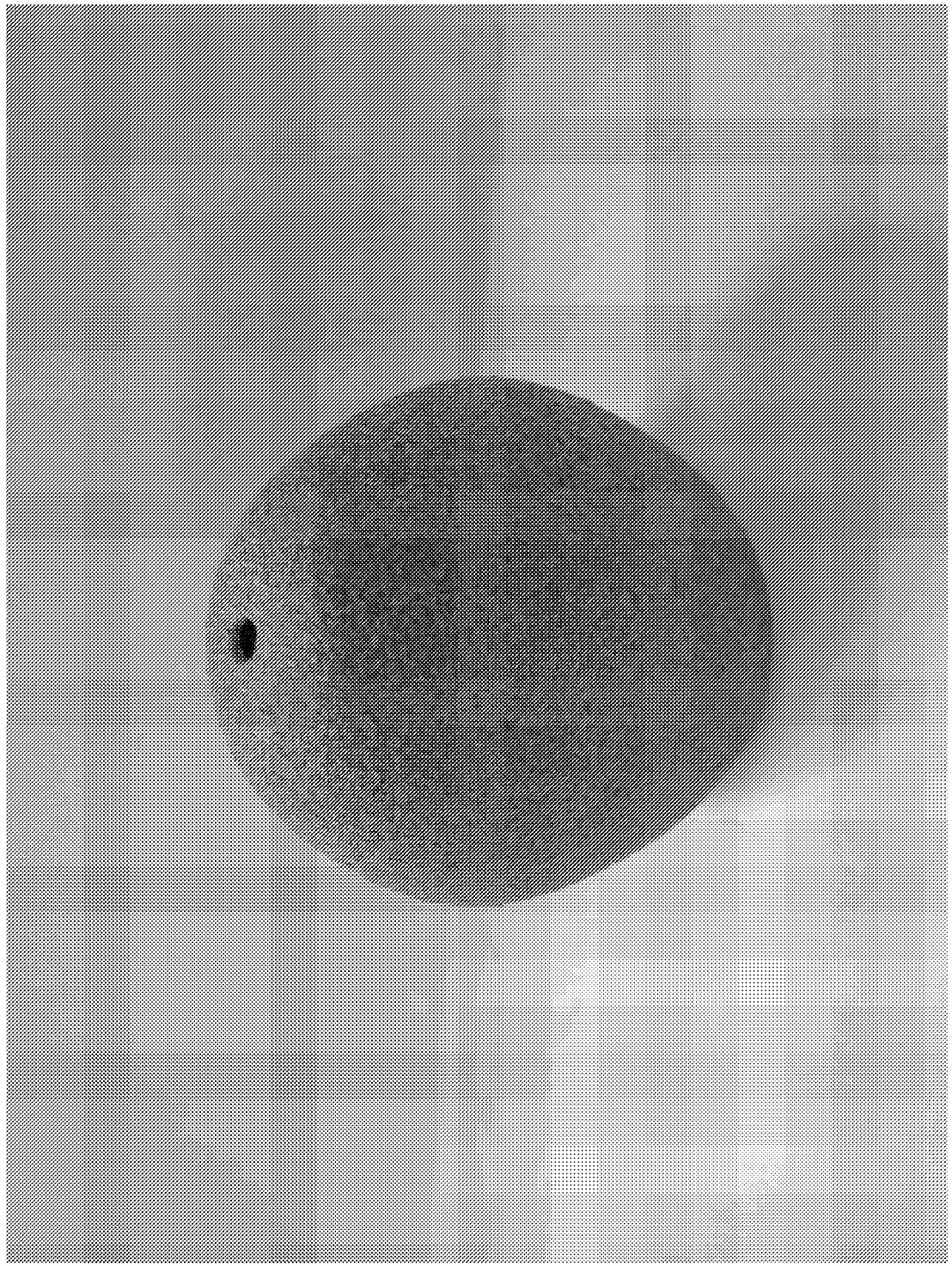
FIG. 33 is a perspective view of one embodiment of a housing with a natural looking appearance.
Figure 34:
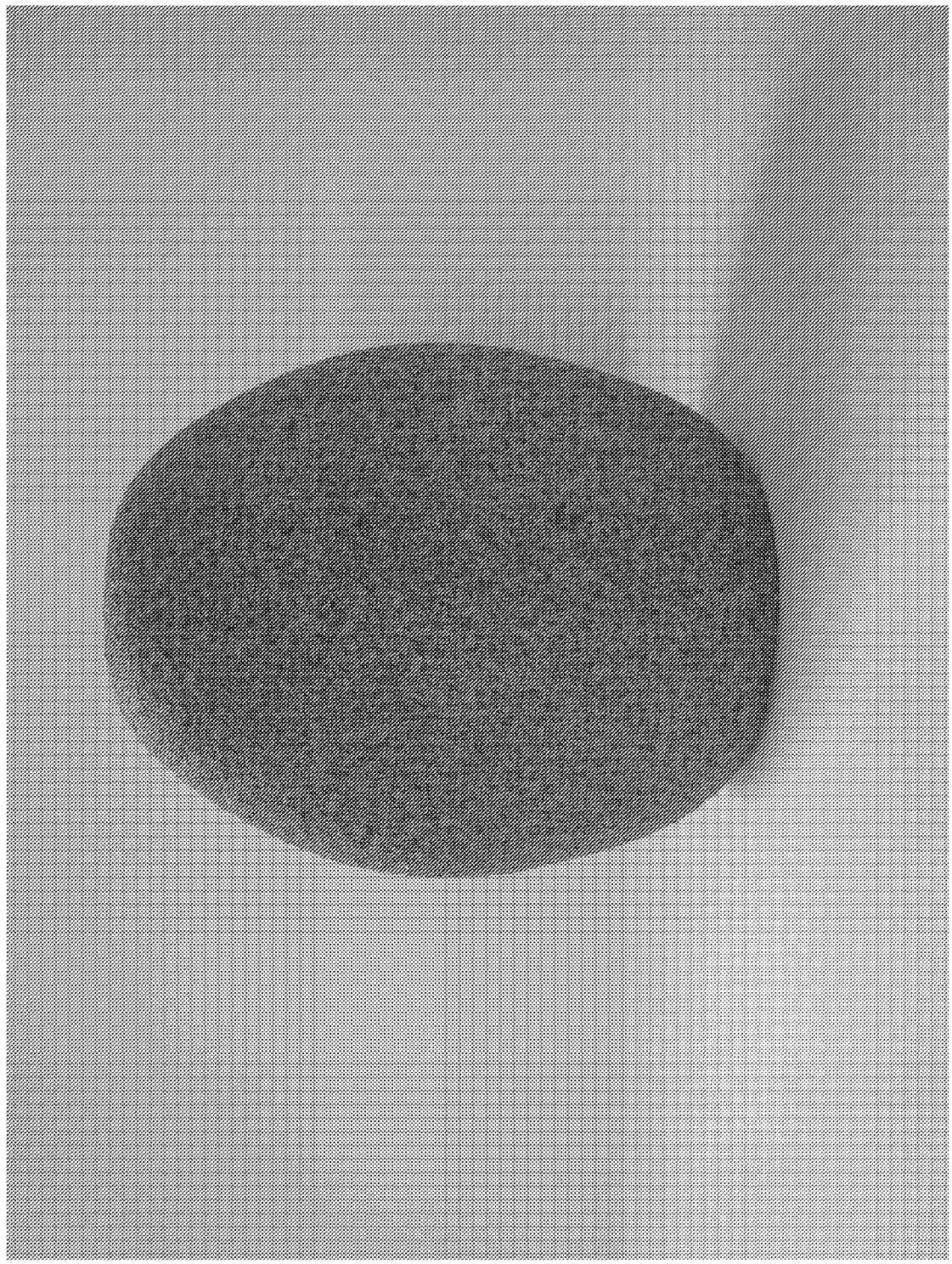
FIG. 34 is a front elevational view of the housing of FIG. 33.
Figure 35:
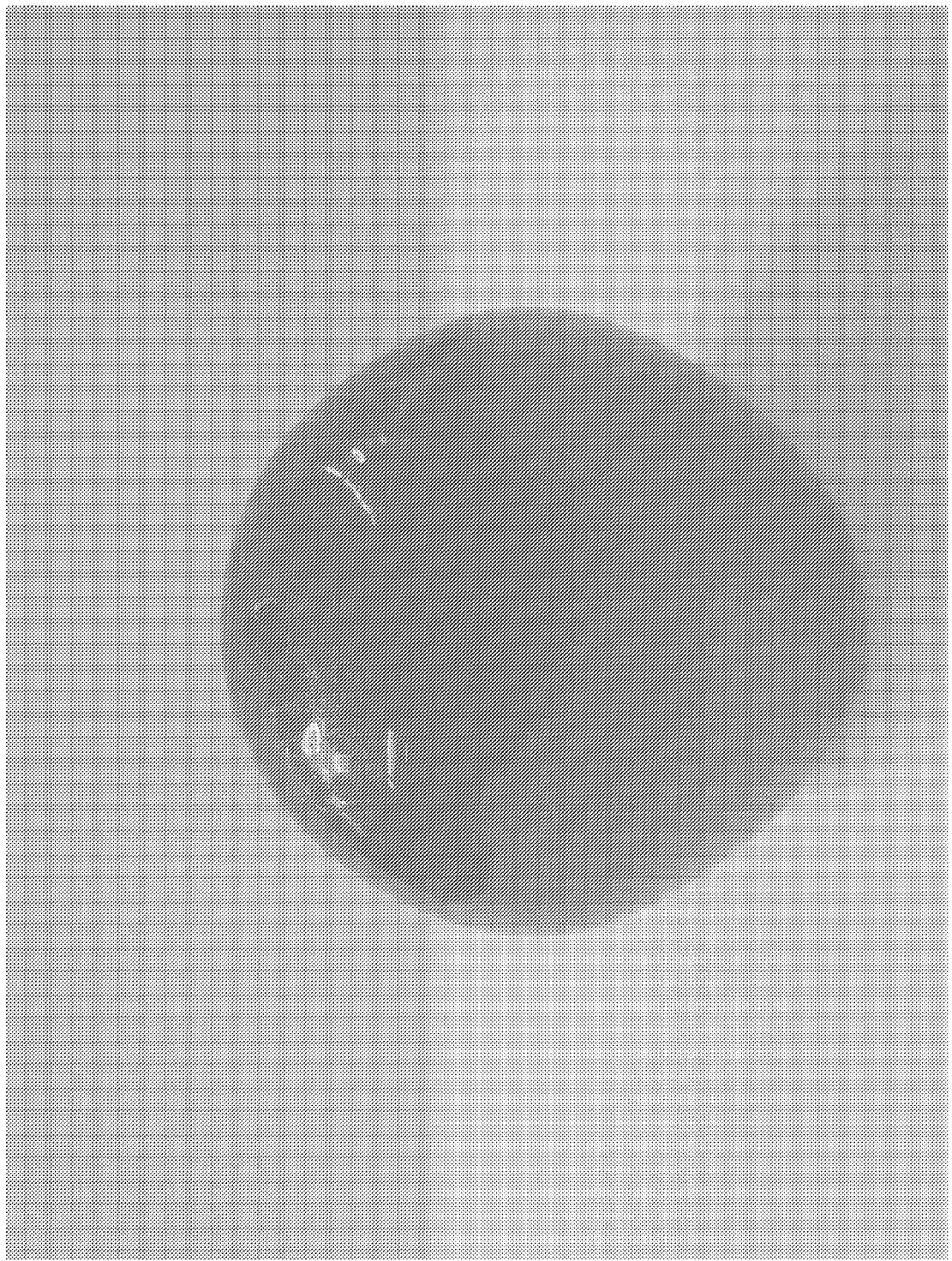
FIG. 35 is a perspective view of another embodiment of a housing with a natural looking appearance.
Figure 36:
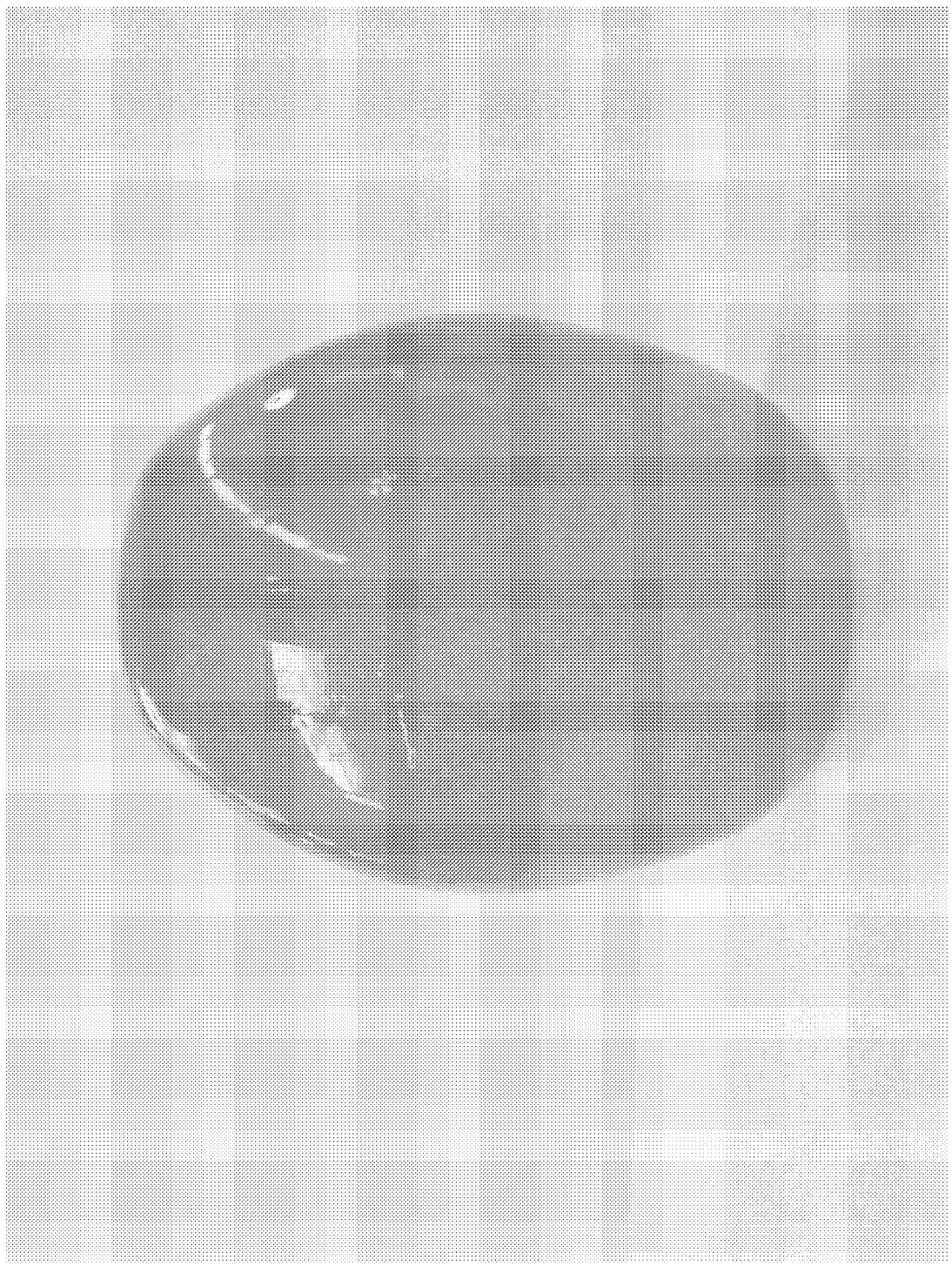
FIG. 36 is a front elevational view of the housing of FIG. 35.
Figure 37:
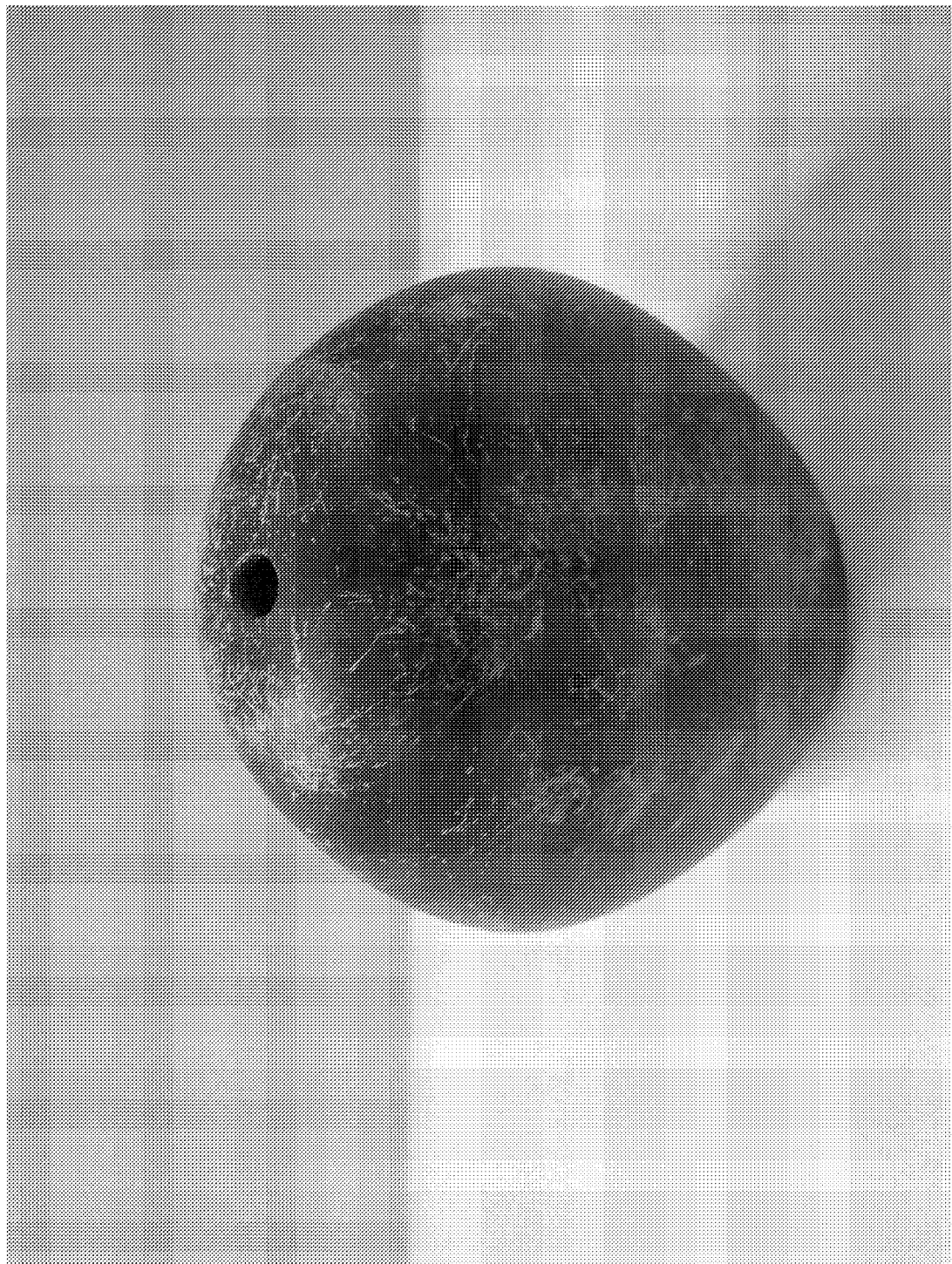
FIG. 37 is a perspective view of a different embodiment of a housing with a natural looking appearance.
Figure 38:
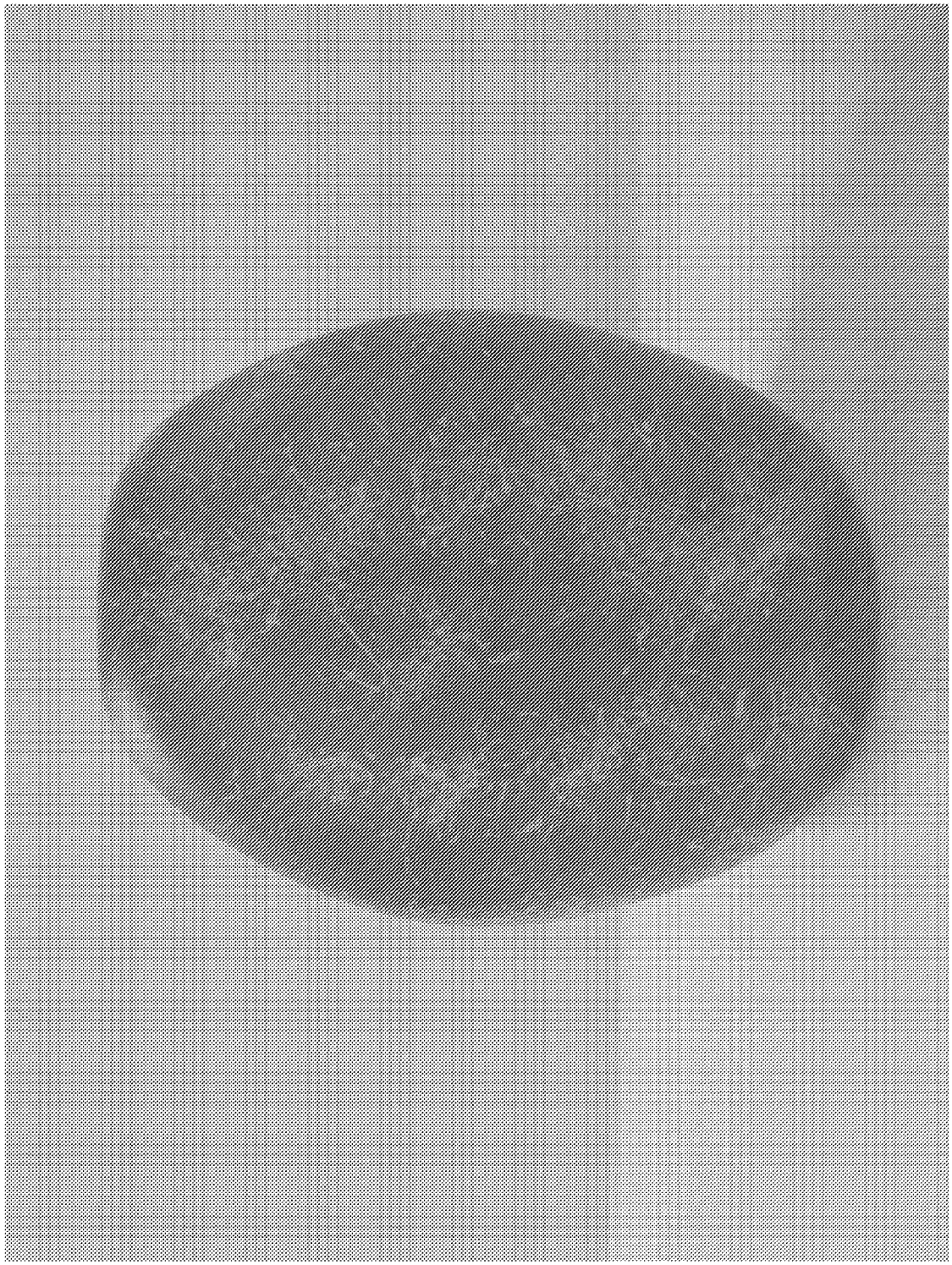
FIG. 38 is a front elevational view of the housing of FIG. 37.

The shroud 322 may be used with a variety of containers, including containers that include caps, collars, peripheral flanges, etc., disposed over the mounting cup 108 of the container 100. For example, a cap similar to the cap 502 depicted in FIGS. 33 and 34 could be used in connection with the shroud 322. The versatility of the present shroud 322 allows for various container refill streams to be used with a single shroud. For example, a cap may or may not be included based on economic considerations, specific structural and space considerations, or regional market considerations that may make a cap desirable or undesirable. In use, peripheral portions of the cap may rest on the substantially flat terminal portions 376a, 376c in addition to or in lieu of the portions 376a-d and angled portions 374a-d interacting with portions of the mounting cup 108. Further, a cap may be provided to act as a stopping mechanism to prevent over insertion of the container 100 and/or shroud 322 within the housing 77 by allowing peripheral portions of the cap to interact with tapered portions and/or angled portions of the inner surface 75 of the housing 77, such as those shown in FIGS. 7 and 8. Similarly, a container 100 provided within the shroud 250 (see FIG. 15) may be used with or without a cap to realize the above-noted benefits.

Figure 23:
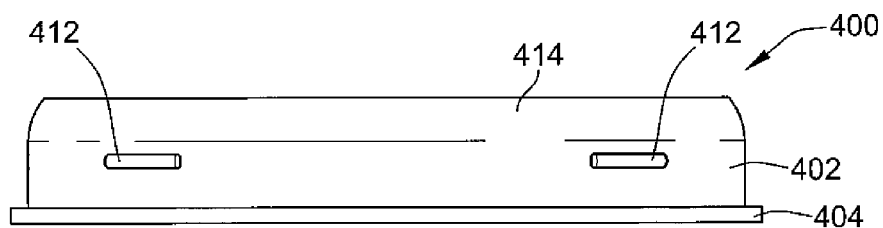
FIG. 23 is a side elevational view of an adapter.
Figure 24:
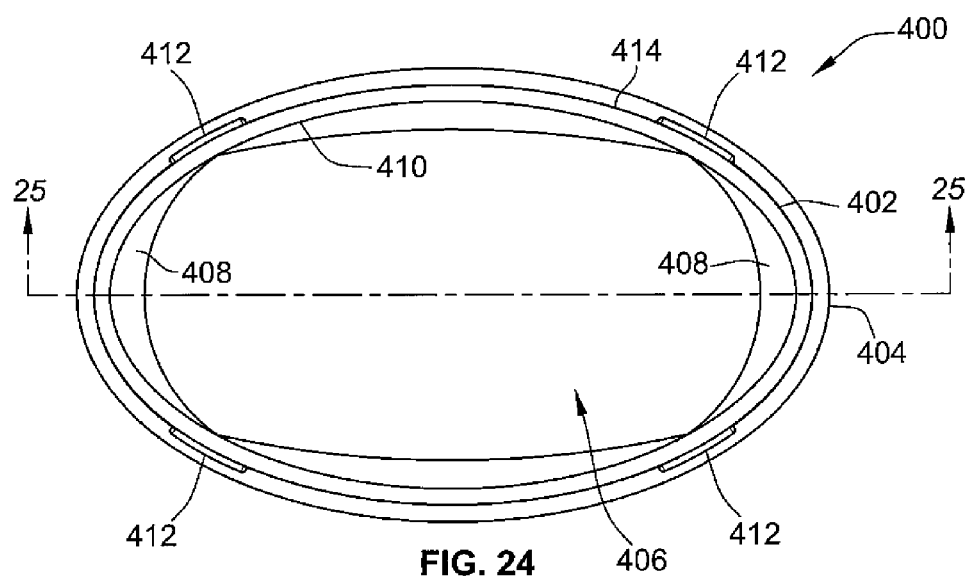
FIG. 24 is a top plan view of the adapter of FIG. 23.
Figure 25:
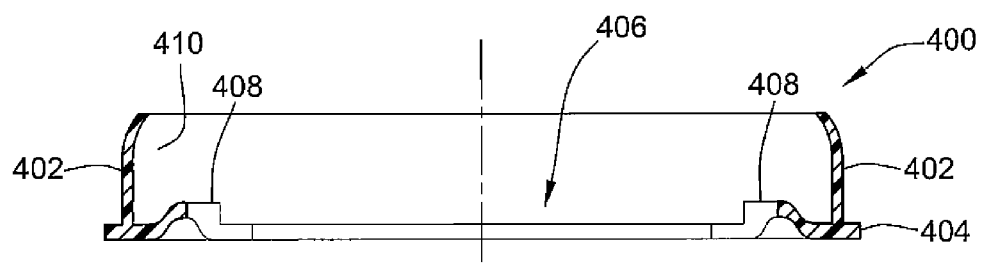
FIG. 25 is a sectional view of the adapter taken along the line 25-25 of FIG. 24.
Figure 26:
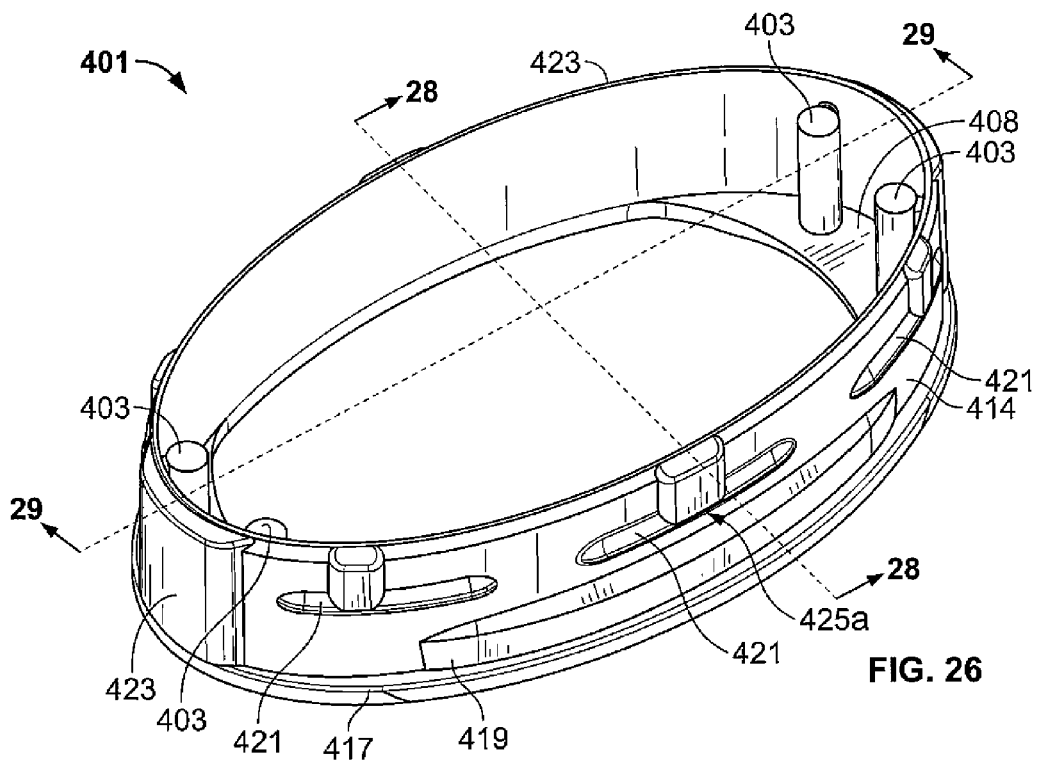
FIG. 26 is a top isometric view of a second embodiment of an adapter.
Figure 27:
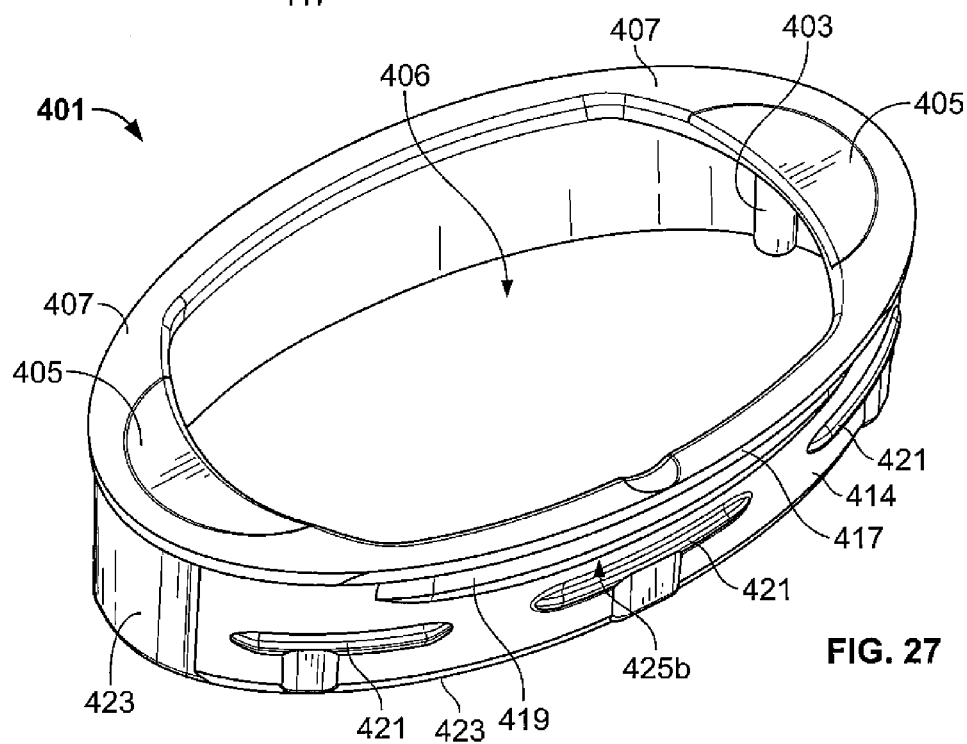
FIG. 27 is a bottom isometric view of the adapter of FIG. 26.

Referring to FIGS. 23-25, a first embodiment of the adapter 400 is illustrated and includes a generally elliptical wall 402 extending upwardly from a similarly shaped base 404. An aperture 406 is disposed through the base 404 and includes four curvilinear sides that are generally similar to the size of a lower portion of the shroud 200, 250. Two support members 408 are disposed on opposing sides of an interior surface 410 of the wall 402. One or more protrusions 412 extend from an external surface 414 of the wall 402. The adapter 400 may optionally include one or more tapered vertical ribs (not shown), which taper downwardly from the interior surface 410 of the wall 402 toward an interior lip of the base 404 adjacent the aperture 406.

Figure 28:
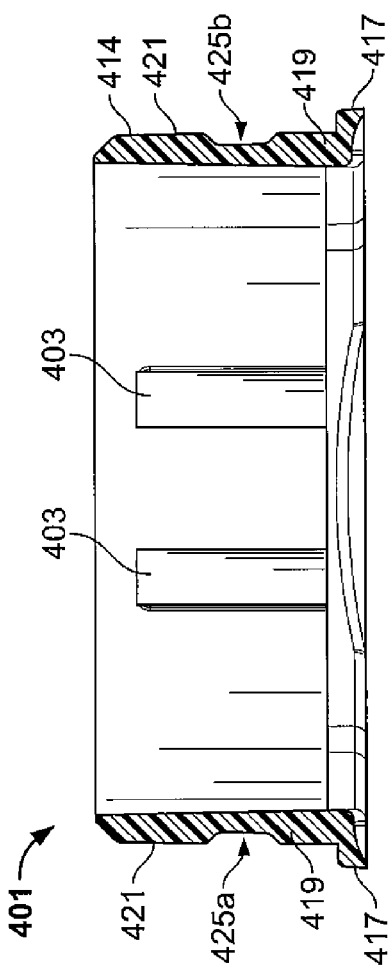
FIG. 28 is a sectional view of the adapter of FIG. 26 taken along the line 28-28 of FIG. 26.
Figure 29:
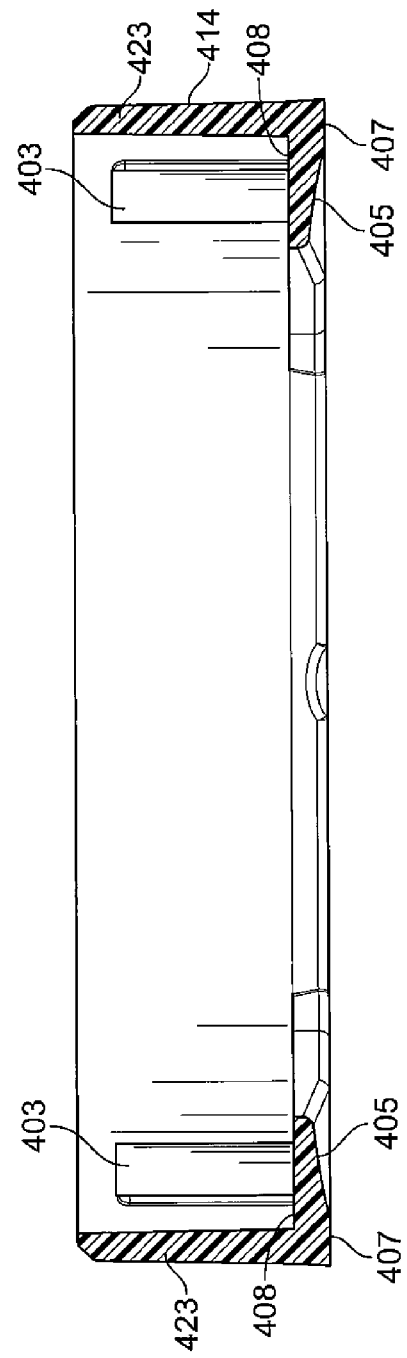
FIG. 29 is a sectional view of the adapter of FIG. 26 taken along the line 29-29 of FIG. 26.

Now turning to FIGS. 26-29, a second embodiment of an adapter 401 is depicted, which is particularly adapted to be used with the dispenser 71 of FIGS. 5-8 and the shroud of FIGS. 21 and 22. The adapter 401 is similar to the first embodiment of the adapter 400 previously discussed except for the differences noted herein. The adapter 401 includes a plurality of cylindrical extension members 403 disposed on, and extending upwardly from, the support members 408. The support members 408 further include depressed portions 405 on exterior bottom sides 407 thereof, which are adapted to provide a contoured support surface for a user's thumb during assembly of the dispenser 71. As best seen in FIG. 28, a sidewall external surface 414 of the adapter 401 includes two opposing ridges 417 disposed along, and extending outwardly from, a lower portion thereof. During assembly of the dispenser 71, the opposing ridges 417 are adapted to interact with the opposing grooves 83 of the housing 77 to prevent the adapter 401 from being inserted too far into the housing 77. Two elongate ribs 419 are disposed adjacent the ridges 417 and also extend outwardly from the external surface 414 of the adapter 401. Further, a plurality of outwardly protruding stop members 421 are disposed on the external surface 414 above the elongate ribs 419 and the ridges 417. Still further, two outwardly protruding rectilinear extension members 423 are disposed at opposing ends of the adapter 401. The area between the protruding rectilinear extension members 423, the protruding stop members 421, and the outwardly extending elongate ribs 419 is substantially flat by comparison and is generally denoted by reference numerals 425a and 425b.

Figure 30:
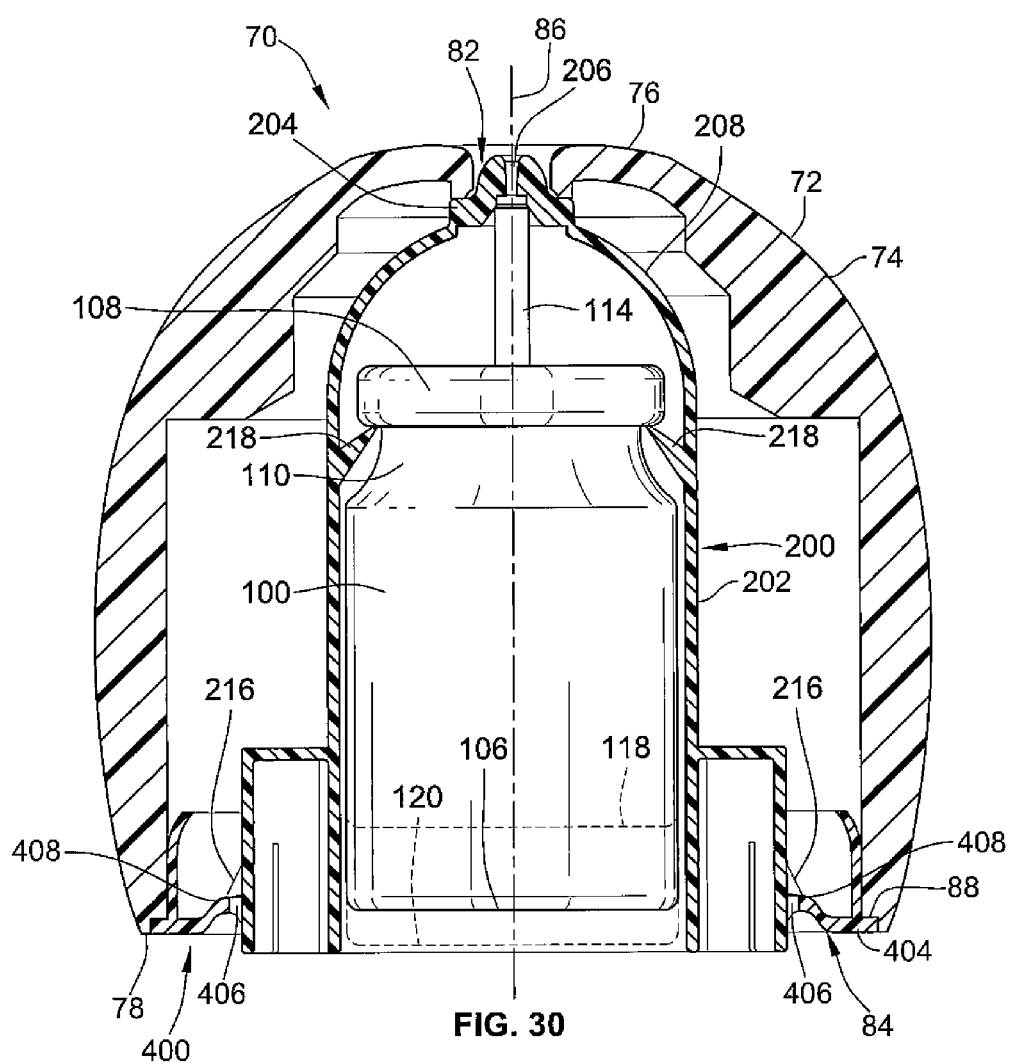
FIG. 30 is a partial sectional view of the aerosol dispenser of FIG. 1 in combination with the shroud of FIG. 10 and the aerosol container of FIG. 9.

Having described the component parts of the aerosol dispenser 70 hereinabove, the inter-relation of all of the parts will now be described. It should be understood that while specific housings are discussed with respect to specific shrouds and/or adapters, that any of the housings, shrouds, adapters, and containers discussed herein may be utilized in connection with any embodiment. Referring to FIG. 30, the aerosol dispenser 70 is shown in cross-section fully assembled. Assembly of the aerosol dispenser 70 may be described sequentially. First, the aerosol container 100 is placed within the shroud 200 such that the flexible internal shoulders 218 snap over the mounting cup 108 on the aerosol container 100 to fixedly hold the aerosol container 100 with respect to the body portion 202 of the shroud 200. The neck 110 of the aerosol container 100 provides a recess into which the shoulders 218 extend to hold the aerosol container 100. The valve stem 114 of the aerosol container 100 is accommodated by and in contact with the actuator socket 204. As indicated by the dashed lines 118, 120 in FIG. 30, the aerosol container 100 may have any number of different lengths. The aerosol container 100 may also have any number of different widths (not shown in FIG. 30), which may be accommodated by the shroud 200 and the internal shoulders 218.

The adapter 400 is placed into the second aperture 84 so that the one or more protrusions 412 thereon snap over the lips 90 extending from the interior surface 92 of the housing 72. The base 404 of the adapter 400 is accommodated by the groove 88 around the periphery of the second aperture 84 such that a bottom surface of the adapter 400 is flush with the bottom end 78 of the housing 72. A user may remove the adapter 400 from the second aperture 84 by simply reversing this process and pulling the adapter 400 out of the second aperture 84.

The shroud 200 with the aerosol container 100 held within is inserted into the housing 72 through the aperture 406 of the adapter 400 until the tapered protrusions 216 snap over the support members 408. The aerosol dispenser 70 is in a rest state when a top end of the shroud 200, i.e., the actuator socket 204, is in physical communication with a portion of the housing 72 defining the first aperture 82 and the tapered protrusions 216 are in physical communication with the support members 408. As illustrated in FIG. 30, in the rest state, the lower edge of the shroud 200 extends from the second aperture 84 and is held adjacent a support surface (not shown). The container 100 is prevented from further inward movement within the shroud 200 through the interaction of the valve stem 114 exerting a force against the actuator socket 204 and the interaction of the internal shoulders 218 with the mounting cup 108. Only exertion of a downward force component onto the housing 72 causes same to move axially downward, i.e., in a direction parallel to the longitudinal axis 86, in relation to the shroud 200, thereby causing compression of the valve stem 114 and the resultant release of the contents of the aerosol container 100.

Figure 19:
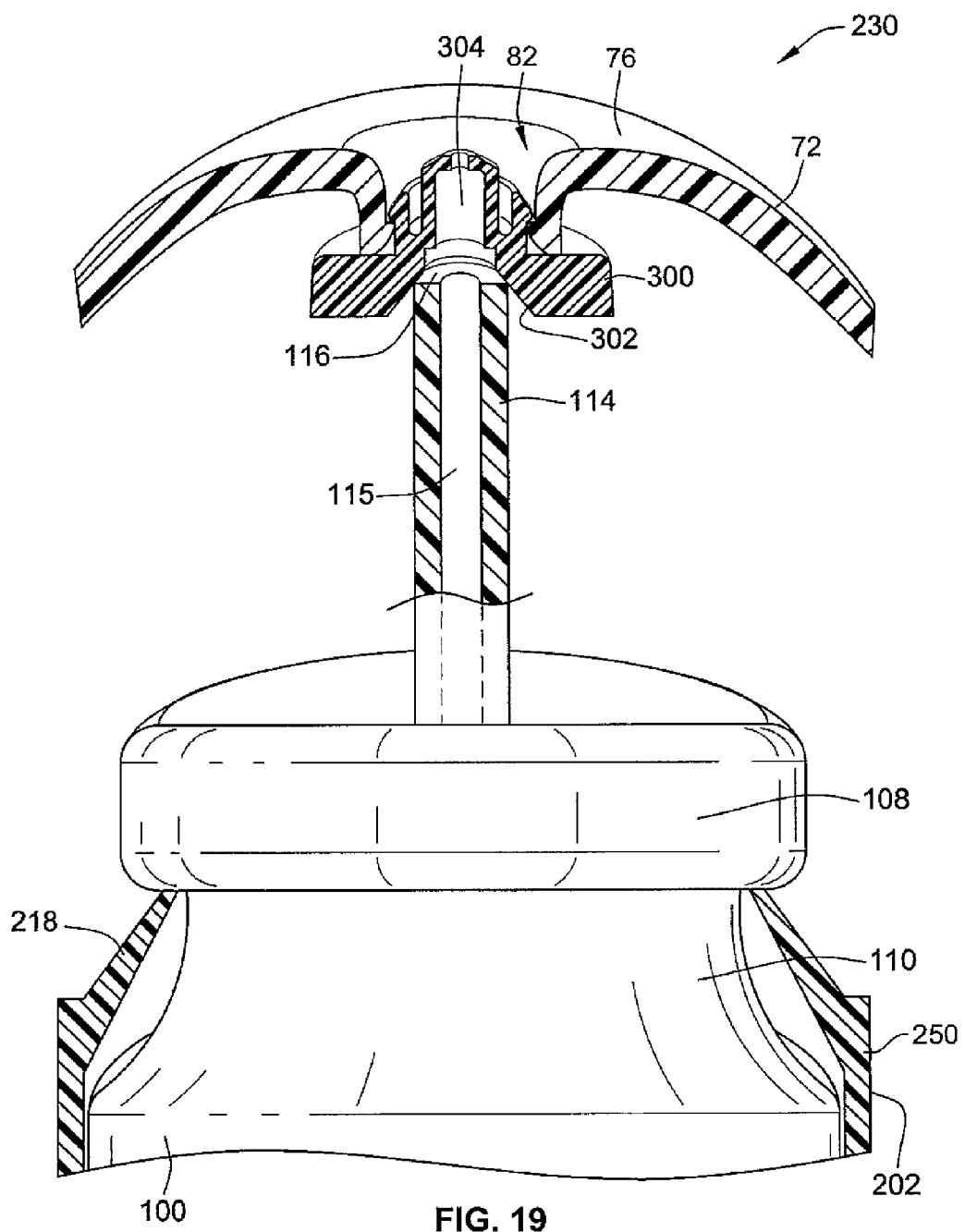
FIG. 19 is an enlarged, partial sectional view of the aerosol dispenser of FIG. 1 in combination with the shroud of FIG. 15 and the aerosol container of FIG. 9.

Turning again to the aerosol dispenser 230 depicted in FIG. 19, the operation of the dispenser 230 is substantially similar to the aerosol dispenser 70 described hereinabove with regard to FIG. 30. The aerosol container 100 is placed into the shroud 250 and inserted into the housing 72 in a similar manner as described in connection with FIG. 30. The aerosol dispenser 230 is in a rest state with the distal end 116 of the valve stem 114 exerting a force against the actuator socket 300 and the tapered protrusions 216 in physical communication with the support members 408 (see FIG. 30). In the rest state, a lower portion of the shroud 250 extends from the second aperture 84. Only exertion of a downward force component onto the housing 72 causes same to move axially downward in relation to the shroud 250, thereby causing compression of the valve stem 114 and the resultant release of the contents of the aerosol container 100. The optional flange extending radially outwardly from the periphery of the mounting cup 108 may provide additional surface area against which upper ends of the internal shoulders 218 may push. In addition, the support elements associated with the internal shoulders 218 add strength to same to inhibit collapse of the internal shoulders 218 by the exertion of a downward force component onto the housing 72 (not shown).

The distal end 116 of the valve stem 114 may tend to press fit into the actuator socket 300 upon use and resist removal when the aerosol container 100 is desired to be replaced. When removing the shroud 250 from the housing 72, the tapering neck 110 may cause the internal shoulders 218 to be pushed radially outwardly and to slip past the neck 110 and over the body 102, thereby leaving the aerosol container 100 within the bore 80. The optional support elements add strength to the internal shoulders 218 to inhibit separation thereof during removal of the shroud 250. Indeed, the shroud 322 depicted in FIGS. 21 and 22 include two opposing elongate support elements 360a, 360b that provide for a similar functionality. Additionally, the optional tapered vertical ribs that taper downwardly from the interior surface 410 of the wall 402 of the adaptor 400 inhibit the mounting cup 108, or the peripheral flange optionally associated therewith, from catching on the base 404 when removing the aerosol container 100 from the housing 72.

Figure 20:
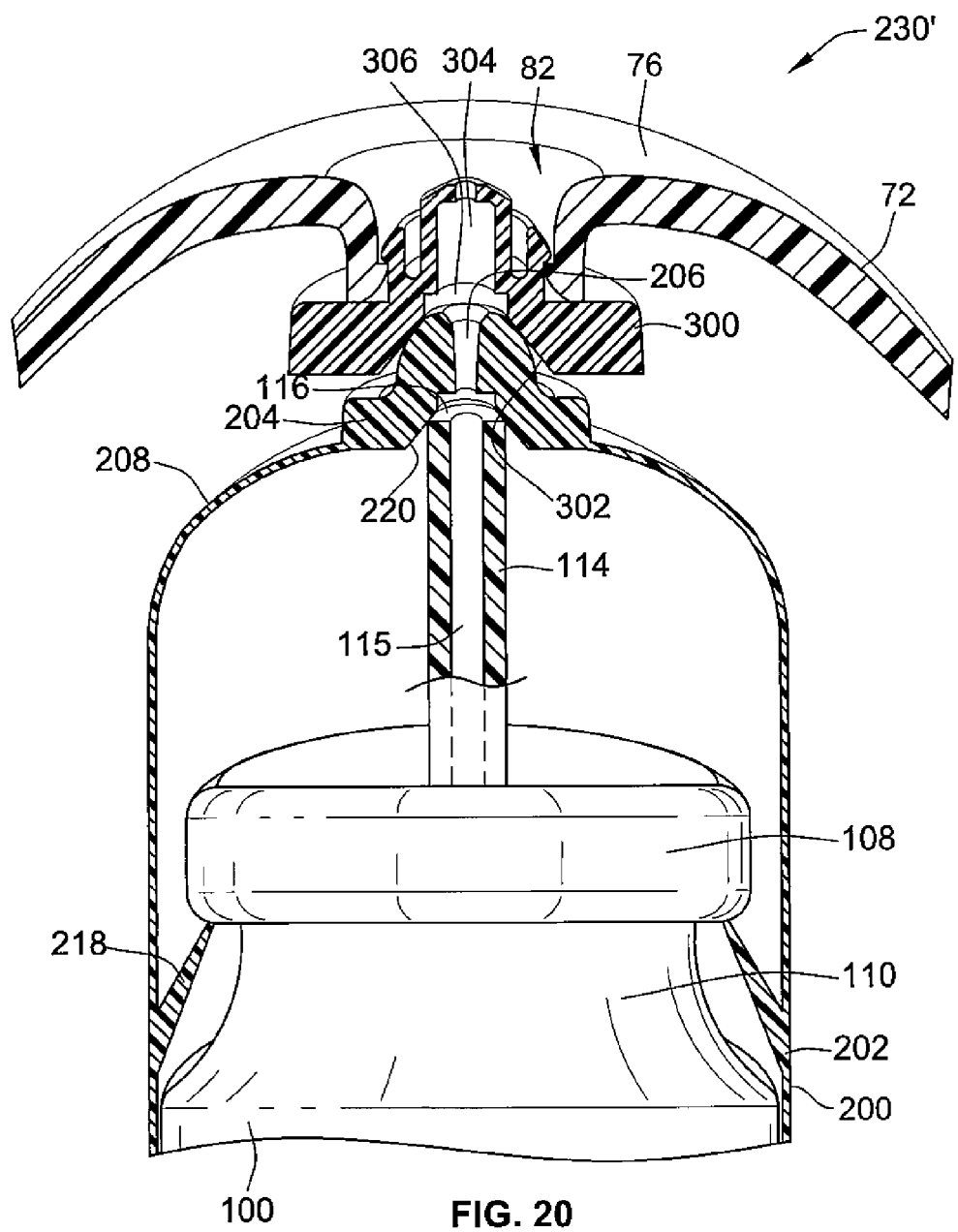
FIG. 20 is an enlarged, partial sectional view of the aerosol dispenser of FIG. 1 in combination with the actuator socket of FIG. 16, the shroud of FIG. 10, and the aerosol container of FIG. 9.

As noted above, another embodiment of an aerosol dispenser 230' is illustrated in FIG. 20. The aerosol dispenser 230' is substantially similar to the aerosol dispenser 70 described hereinabove with regard to FIG. 30 except for the following difference. The actuator socket 204 is retained within the inlet portion 302 of the actuator socket 300 and the actuator socket 300 is disposed adjacent surfaces of the housing 72 defining the first aperture 82. The aerosol dispenser 230' otherwise operates in an identical fashion as the aerosol dispensers 70, 230 described hereinabove and includes a rest state wherein a lower portion of the shroud 200 extends from the second aperture 84.

Figure 31:
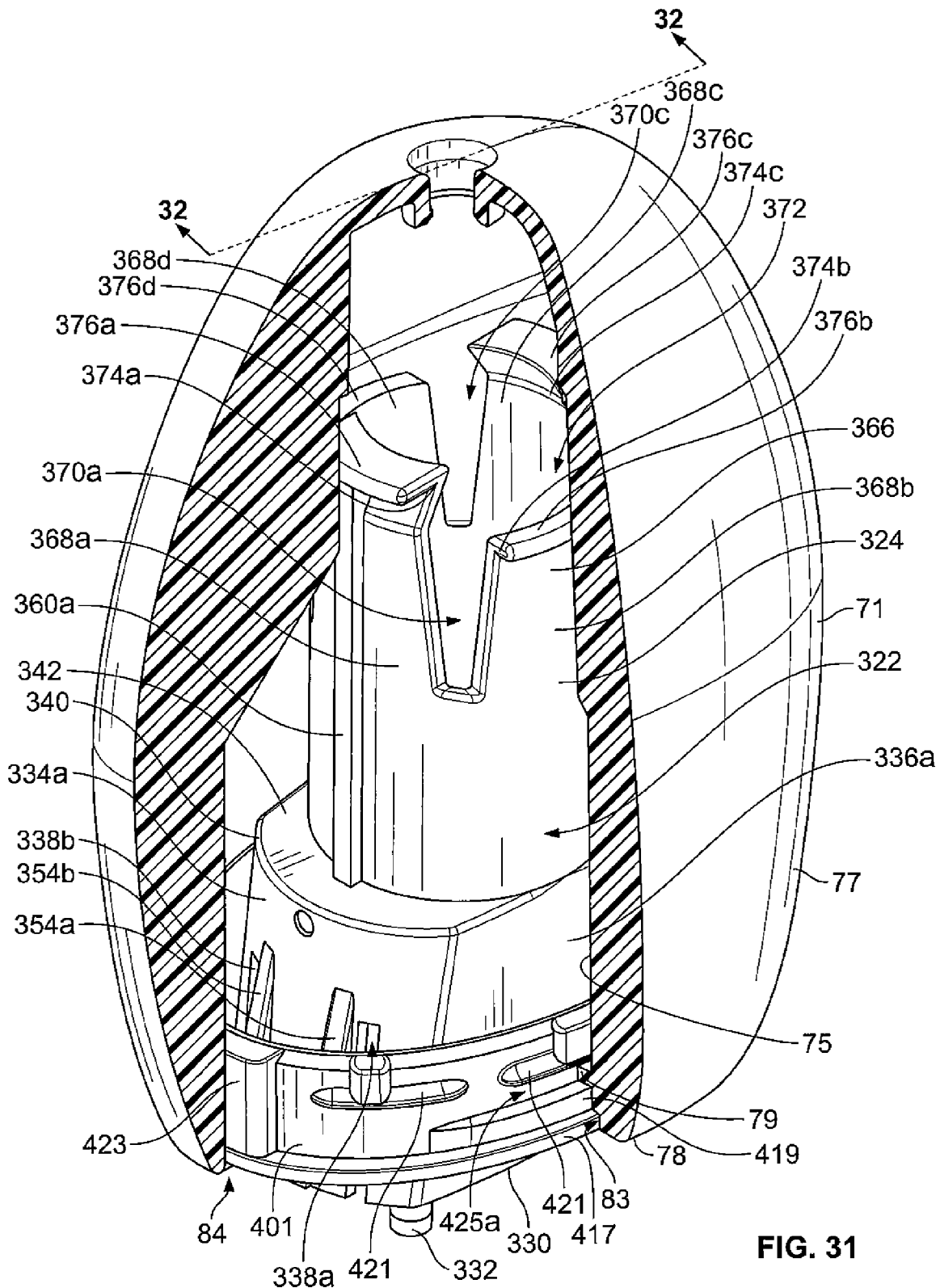
FIG. 31 is an isometric view of the aerosol dispenser of FIG. 5 in combination with the shroud of FIG. 21 and the adapter of FIG. 26, wherein a portion of the dispenser has been cutaway for clarity.
Figure 32:
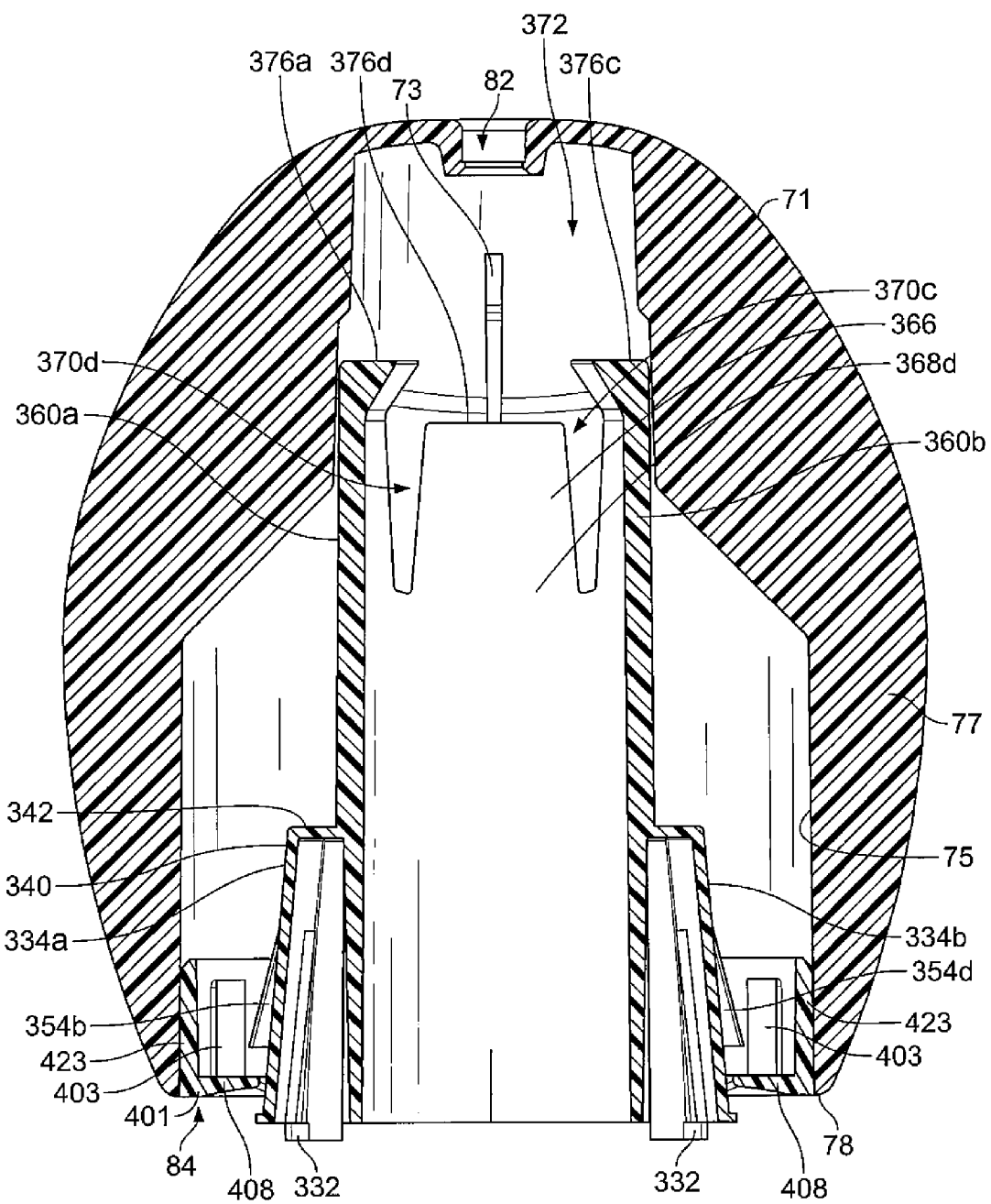
FIG. 32 is a partial sectional view of the aerosol dispenser of FIG. 5 in combination with the shroud of FIG. 21 and the adapter of FIG. 26 taken along the line 32-32 shown in FIG. 31.

Referring to FIGS. 31 and 32, the aerosol dispenser is substantially similar to the aerosol dispenser 70 described hereinabove with regard to FIG. 30 except for the following differences. The container (not shown) is inserted into the central opening 372 through the top portion 366 of the cylindrical body 324. Insertion of the container 100 causes the towers 368a-d to flex outwardly to accommodate the container 100. Once the container 100 is disposed fully therein, the towers 368a-d flex inwardly toward the mounting cup 128 of the container 100. The mounting cup 128 interacts with the angled portions 374a-d- of the towers 368a-d to hold the container 100 inside of the shroud 322. Alternatively, the dispenser may be inserted into the opening 84 disposed at the bottom edge 330 of the shroud 322 and is locked into place in a similar manner as described previously herein.

Figure 31A:
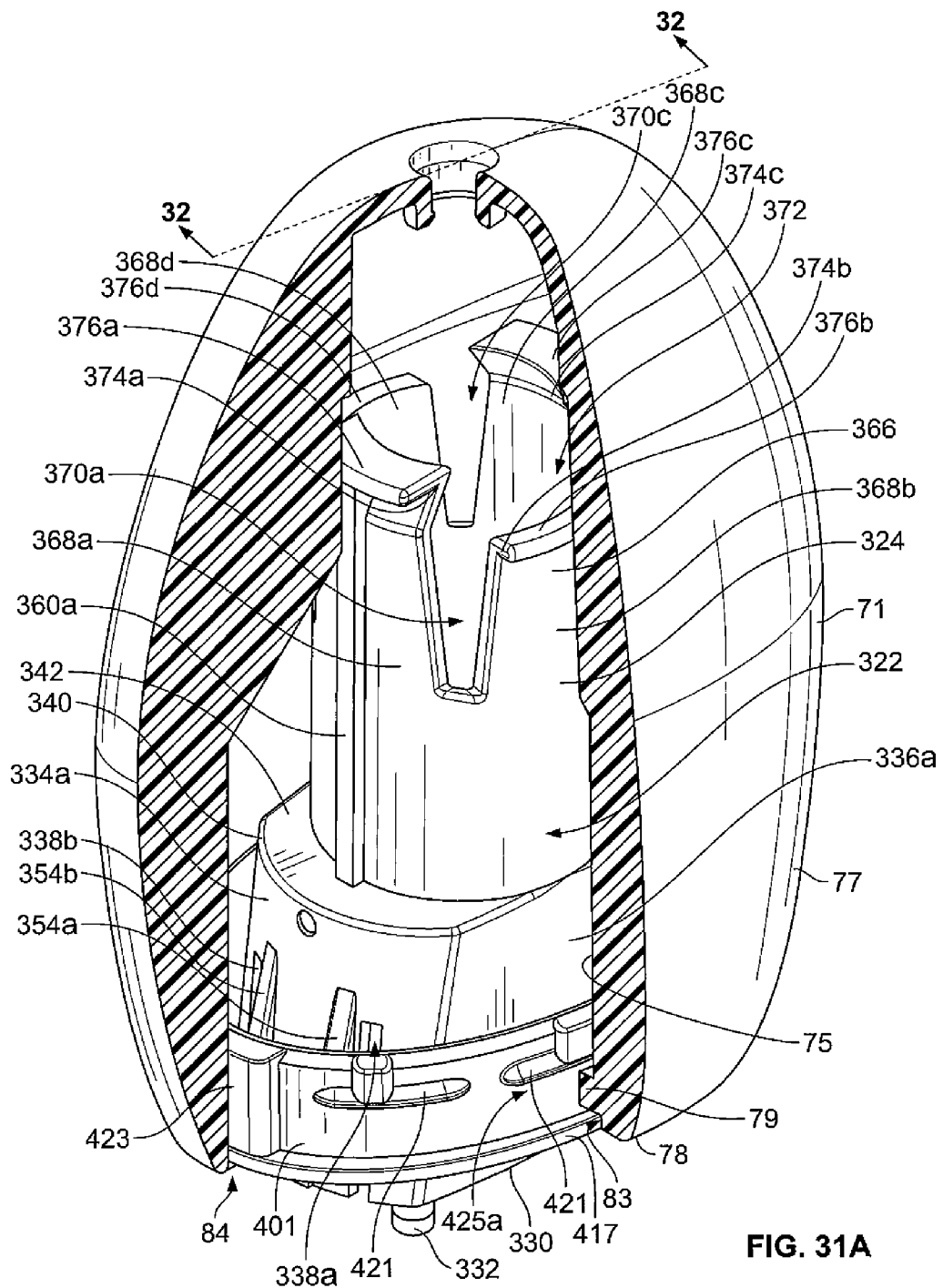
FIG. 31A is a view similar to the one depicted in FIG. 31 showing a modification to the adapter.

As best seen in FIG. 31, the adapter 401 is placed into the second aperture 84 so that the plurality of outwardly protruding stop members 421 are forced past the two curvilinear protrusions 79 that circumscribe a portion of the inner surface 75 of the housing 77. Thereafter, the two curvilinear protrusions 79 are seated in the areas denoted by 425a and 425b between the stop members 421 and the elongate ribs 419 of the adapter 401. FIG. 31A depicts an alternative embodiment, which omits the elongate ribs 419 and provides for the receipt of the two curvilinear protrusions 79 between the stop members 421 and the ridges 417. With respect to both embodiments, the ridges 417 of the adapter 401 are accommodated within the groove 83 around the periphery of the second aperture 84 such that a bottom surface of the adapter 401 is flush with the bottom end 78 of the housing 77. A user may remove the adapter 401 from the second aperture 84 by simply reversing this process and pulling the adapter 401 out of the second aperture 84.

The shroud 322 with the aerosol container 100 held within is inserted into the housing 77 through the aperture 406 of the adapter 401 until the tapered protrusions 354a-d snap over the support members 408. The aerosol dispenser 71 is in a rest state when a top end of the shroud 322 is in physical communication with a portion of the housing 72 defining the first aperture 82 and the tapered protrusions 354a-d are in resilient physical communication with the support members 408. Similar to the shrouds 200, 250, the shroud 322 may also utilize the actuator socket 300. The aerosol dispenser 71 otherwise operates in an identical fashion as the dispensers 70, 230, 230' described hereinabove and includes a rest state wherein a lower portion of the shroud 200 extends from the second aperture 84.

It is contemplated that any of the aerosol dispensers 70, 71, 230, 230' described hereinabove could be utilized, for example, by placing the aerosol dispenser 70, 71, 230, 230' on a support surface with the first aperture 82 facing away from the support surface and the second aperture 84 facing downwardly toward the support surface. Subsequent downward force applied to the housing 72, 77 results in same telescopically sliding about the longitudinal axis 86, or substantially parallel thereto, in relation to the shroud 200, 270, 320, 322. Displacement of the housing 72, 77 results in axial compression of the valve stem 114, which opens the valve assembly within the aerosol container 100. Fluid emitted from the aerosol container 100 passes through the passage 115 of the valve stem 114, out the distal end 116 thereof, through the respective actuator socket 204, 300, out the first aperture 82, and into the ambient environment. In one embodiment, the fluid is dispensed from the aerosol container 100 through the first aperture 82 in a direction substantially parallel to the axis 86 of the housing 72, 77. In other embodiments, the fluid is dispensed at an angle from the axis 86 of the housings 72, 77 through the first aperture 82. In yet other embodiments, fluid from the aerosol container 100 may be directed via tubing (not shown) or other means to the aperture 82, which may or may not be aligned with the axis 86 of the housing 72, 77.

Figure 5:
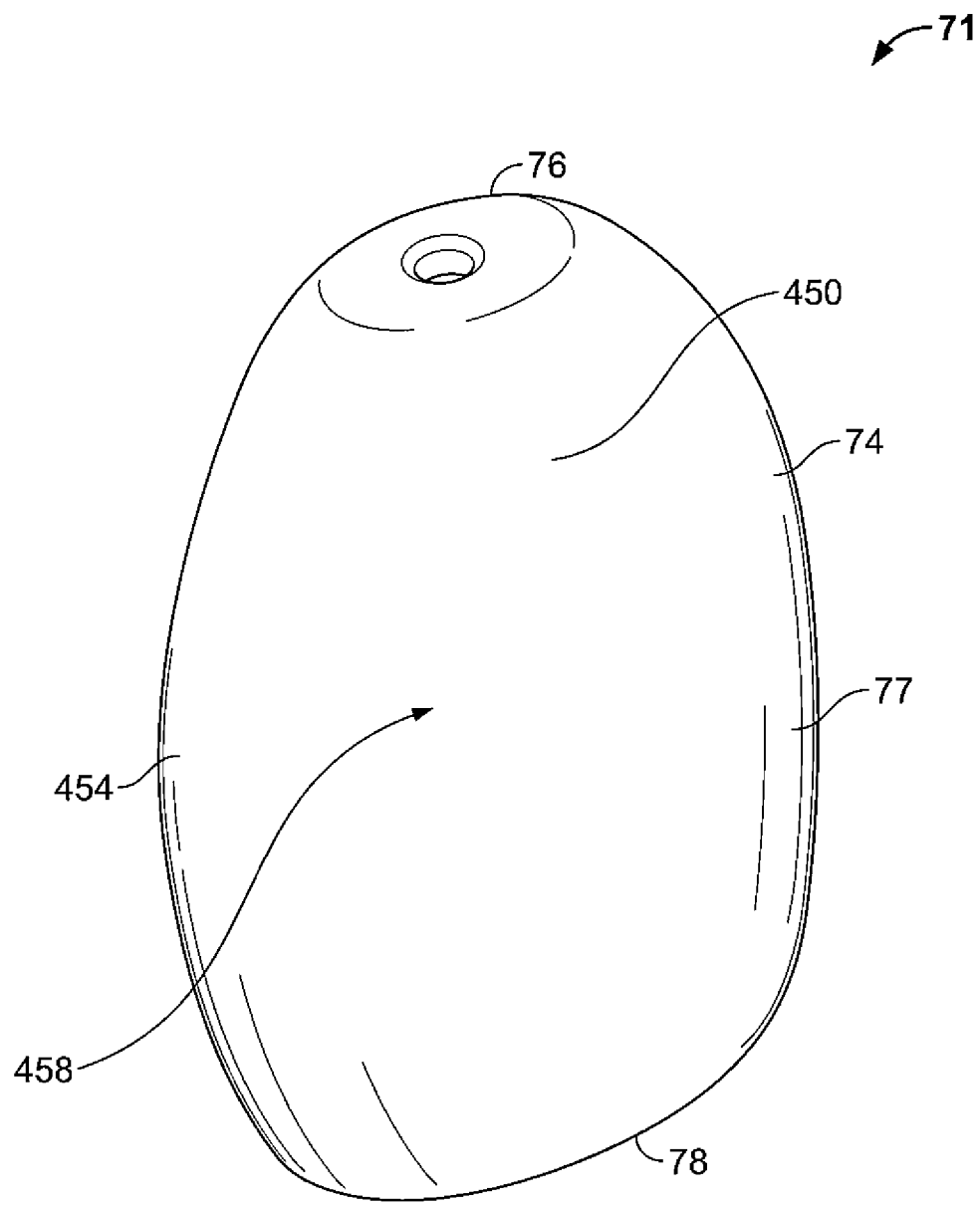
FIG. 5 is a top, front, and left side isometric view of a second embodiment of an aerosol dispenser.
Figure 6:
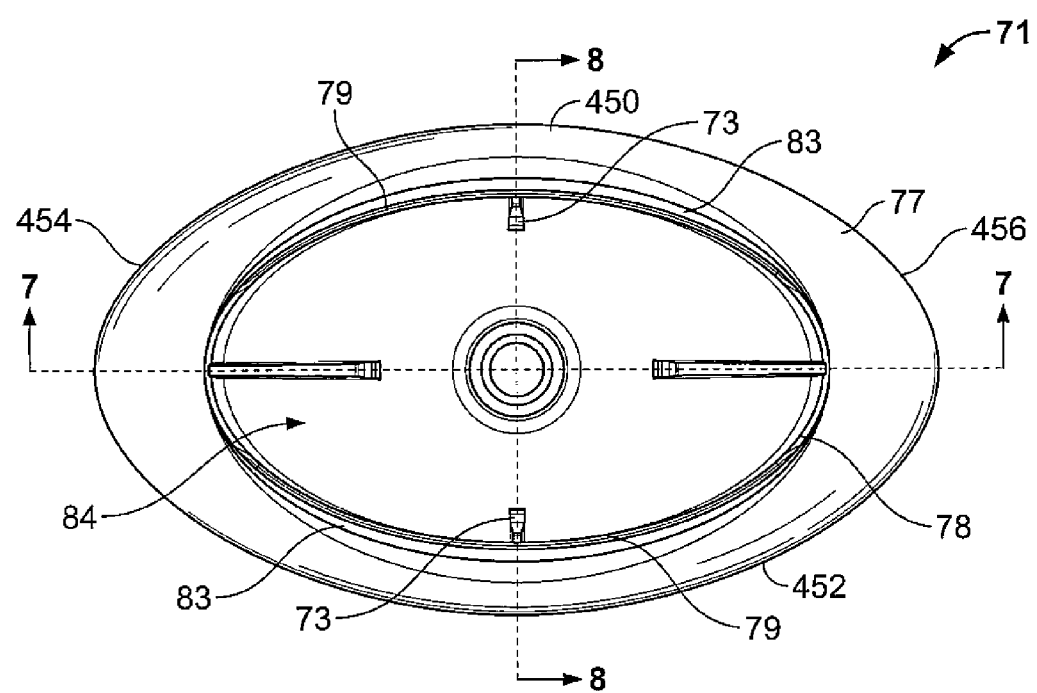
FIG. 6 is a bottom elevational view of the aerosol dispenser of FIG. 5.
Figure 7:
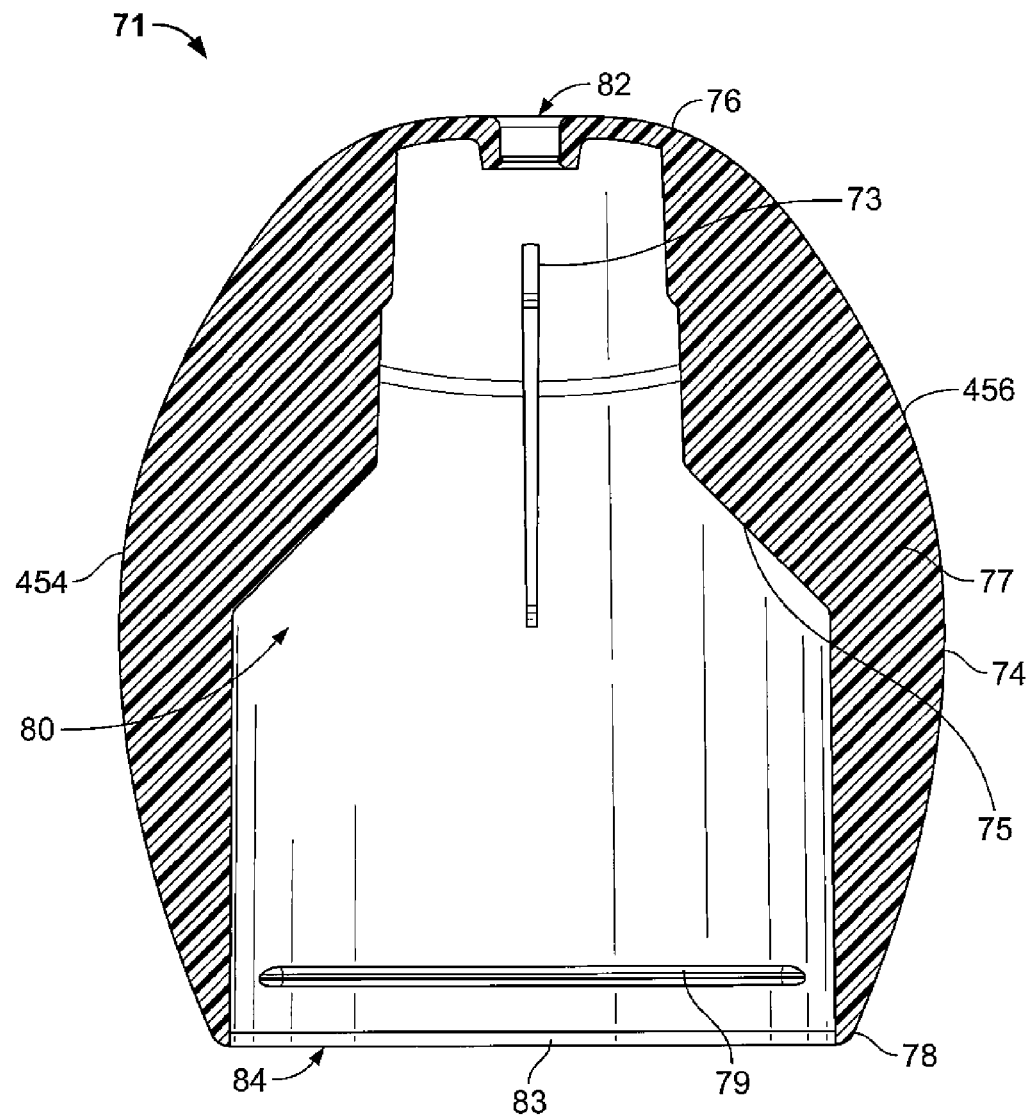
FIG. 7 is a sectional view of the aerosol dispenser of FIG. 5 taken along the line 7-7 of FIG. 6.
Figure 8:
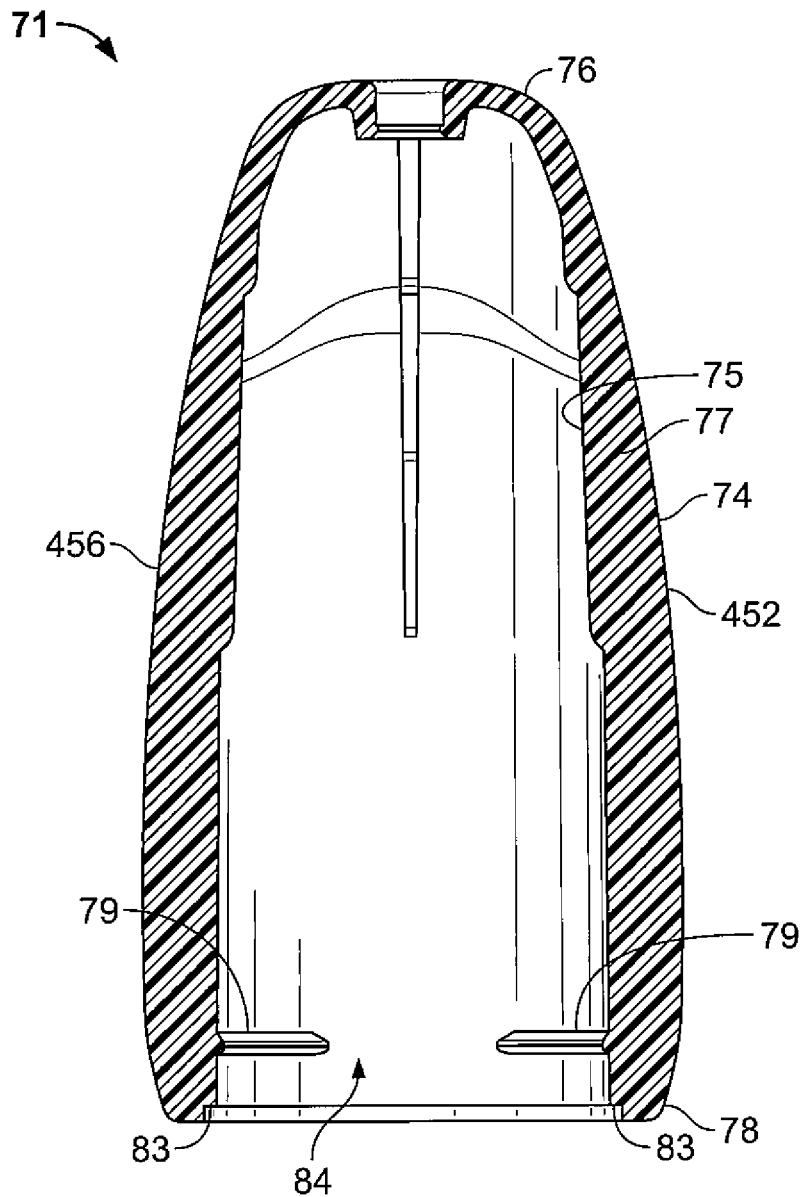
FIG. 8 is a sectional view of the aerosol dispenser of FIG. 5 taken along the line 8-8 of FIG. 6.

A user's grip on the housing during axial movement thereof is important to effective dispensing. Turning to FIGS. 2, 3, and 5 the housing 72, 77 is provided with smooth or textured curvilinear sides 74, wherein the curvilinear sides 74 lack any discontinuities, straight lines, or right angles. The curvilinear sides 74 comprise first and second faces 450, 452, respectively, having width dimensions substantially greater than third and fourth faces 454, 456, respectively. See, generally, FIGS. 1-8. A medial portion 458 of the faces 450-456 extends radially outwardly from the longitudinal axis 86 of the housing 72, 77 to a greater extent than portions of the faces 450-456 adjacent the top end 76 and the bottom end 78. However, it is anticipated that one or more other and/or different portions of the housing 72, 77 may extend radially outwardly from the longitudinal axis 86 to a greater extent. Alternatively, the faces 450-456 may extend radially outwardly from the longitudinal axis 86 of the housing 72, 77 the entire length of the housing 72, 77 between the top end 76 and the bottom end 78.

The tapering cross-sectional width of the housing 72, 77 provides an ergonomic gripping surface that conforms to the contour of a user's palm and/or fingers when gripping the housing 72, 77. Indeed, it has been found that the varying cross-sectional width affords any shape of hand a comfortable resting place to effectively grip the housing 72, 77, i.e., smaller hands may find it more comfortable to grip the housing 72, 77 to a greater extent above the medial portion 458 than a user with a larger hand. Further, a user may grip the housing 72, 77 so as to place their palm adjacent the faces 450, 452 with a greater width, the faces 454, 456 with a smaller width, or any combination thereof. It is anticipated that the slope and degree to which the faces 450-456 taper outwardly from the top end 76 toward the medial portion 458 and inwardly from the medial portion 458 to the bottom end 78, may be varied. It is also anticipated that the widths of any of the faces 450-456 may be varied. However, keeping a natural contour to the faces 450-456 without any apparent discontinuities is important to ensure varying sized hands may grip the container and to providing an ergonomic gripping surface.

Another consideration for the consumer is the appearance of the housing 72, 77, which preferably has a natural look, such as a smooth or textured pebble. With this consideration in mind, the housing 72, 77 has been provided with the smooth or textured curvilinear sides 74 that give the impression of lacking any man-made features. The curvilinear sides 74 may also be provided with a natural looking pattern, such as a wood grain, a stone pattern with or without inclusions, a fossil pattern, etc. For example, FIGS. 33-38 depict several embodiments of housings imparted with a natural looking rock pattern. It has been found that shaping the housing 72, 77 to mimic the shape of a naturally occurring object and/or such that the housing 72, 77 comprises a naturally occurring object, provides the above-noted benefits to gripping the surface of the housing 72, 77. It has also been found that shaping the housing 72, 77 like a naturally occurring object and/or forming the housing 72, 77 from a natural object has the added aesthetic benefit of blending into surroundings in a home, work, or other environment more easily, i.e., the aerosol dispenser 70, 71 does not intrusively stand in the user's environment and appear as a man-made aerosol dispenser. Other shapes presently contemplated include stones, shells, or any other natural occurring object, insofar as the shape lacks any discontinuities, straight lines, or right angles over the faces 450-456.

Figure 39:
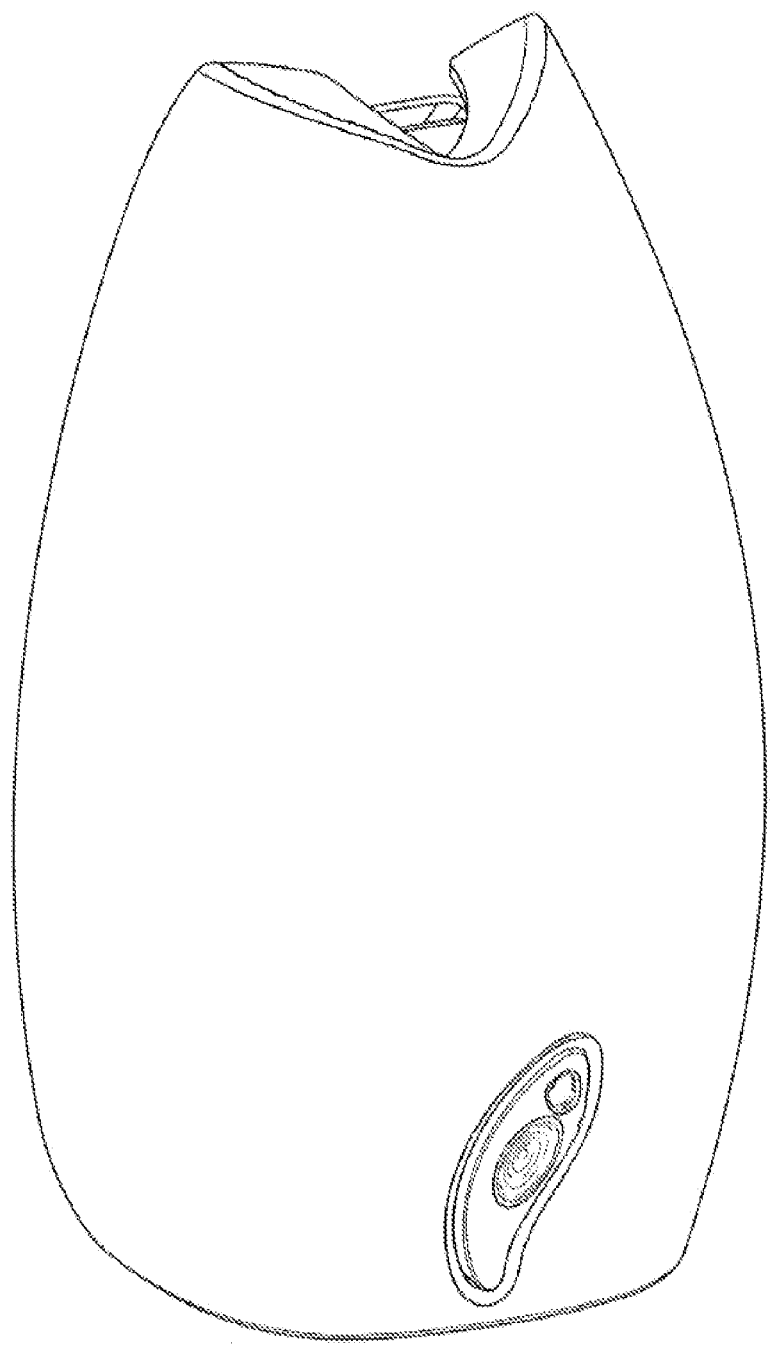
FIG. 39 is an isometric view of an alternative aerosol dispenser utilizing an electro-mechanical drive unit, which is provided with a natural looking pattern.
Figure 39A:
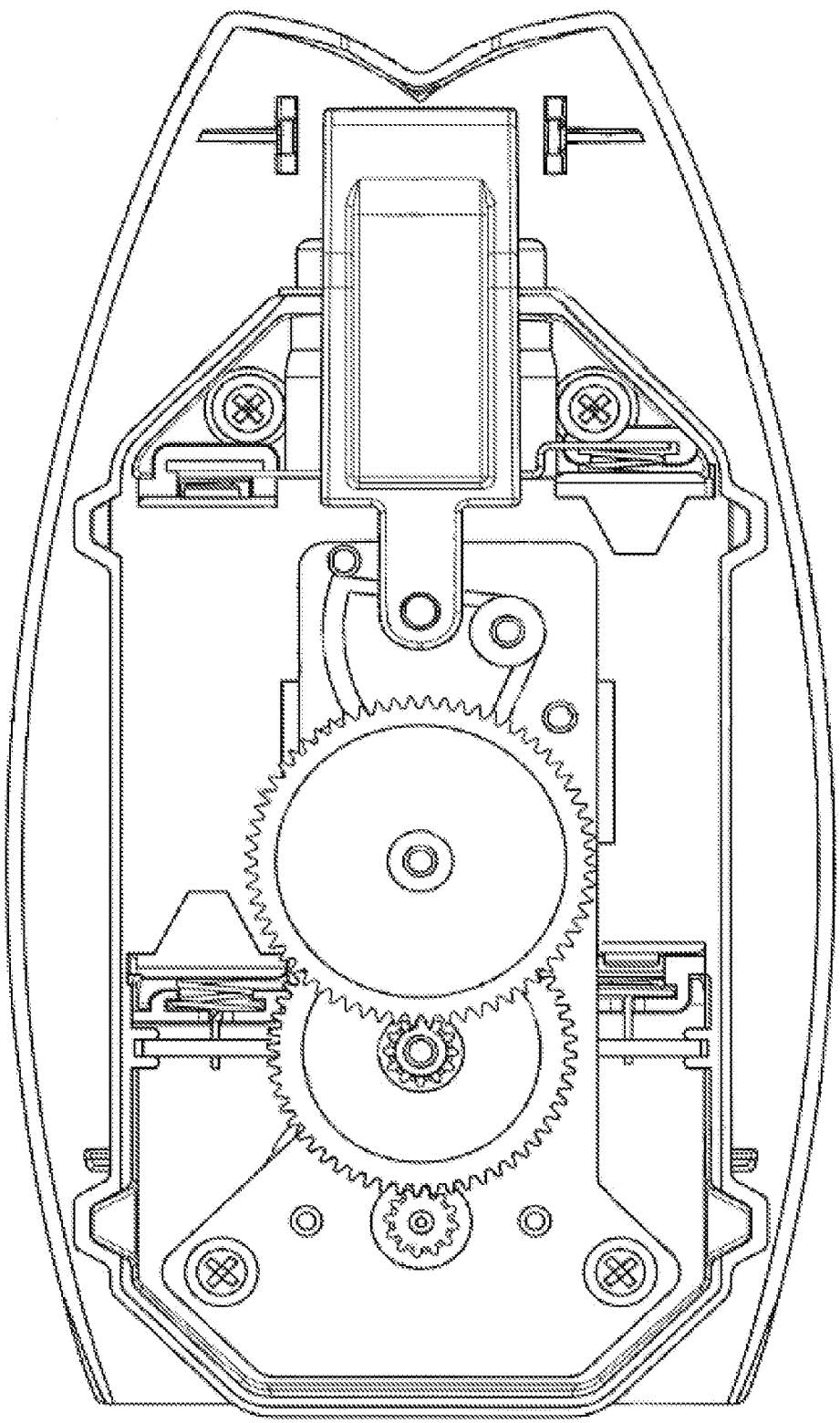
FIG. 39A is a rear elevational view of the dispenser of FIG. 39 with a rear panel removed to shown the electro-mechanical drive unit.
Figure 40:
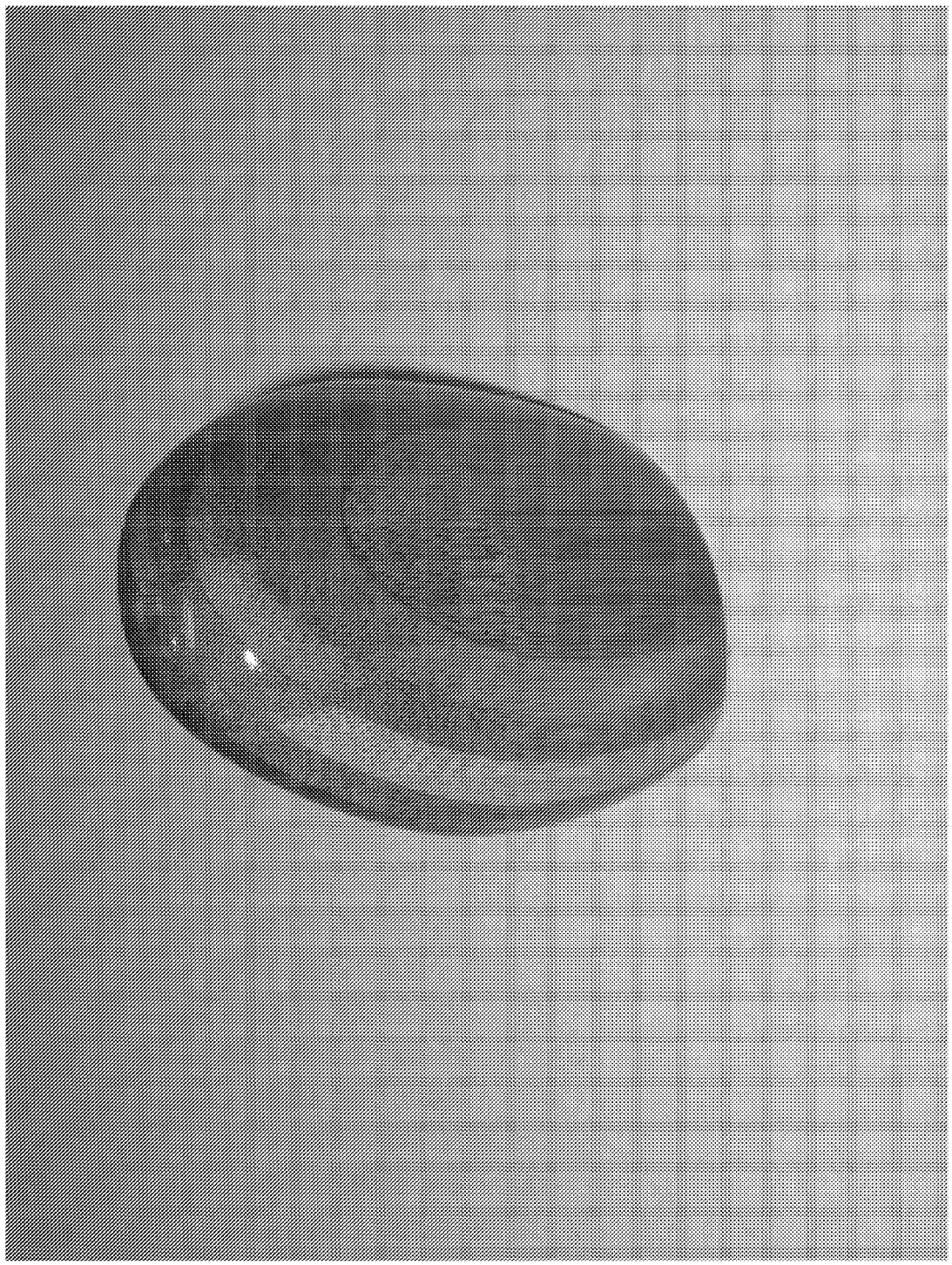
FIGS. 40-44 are perspective views other dispensers similar to the ones depicted in FIGS. 1-8, which are formed from naturally occurring objects.
Figure 41:
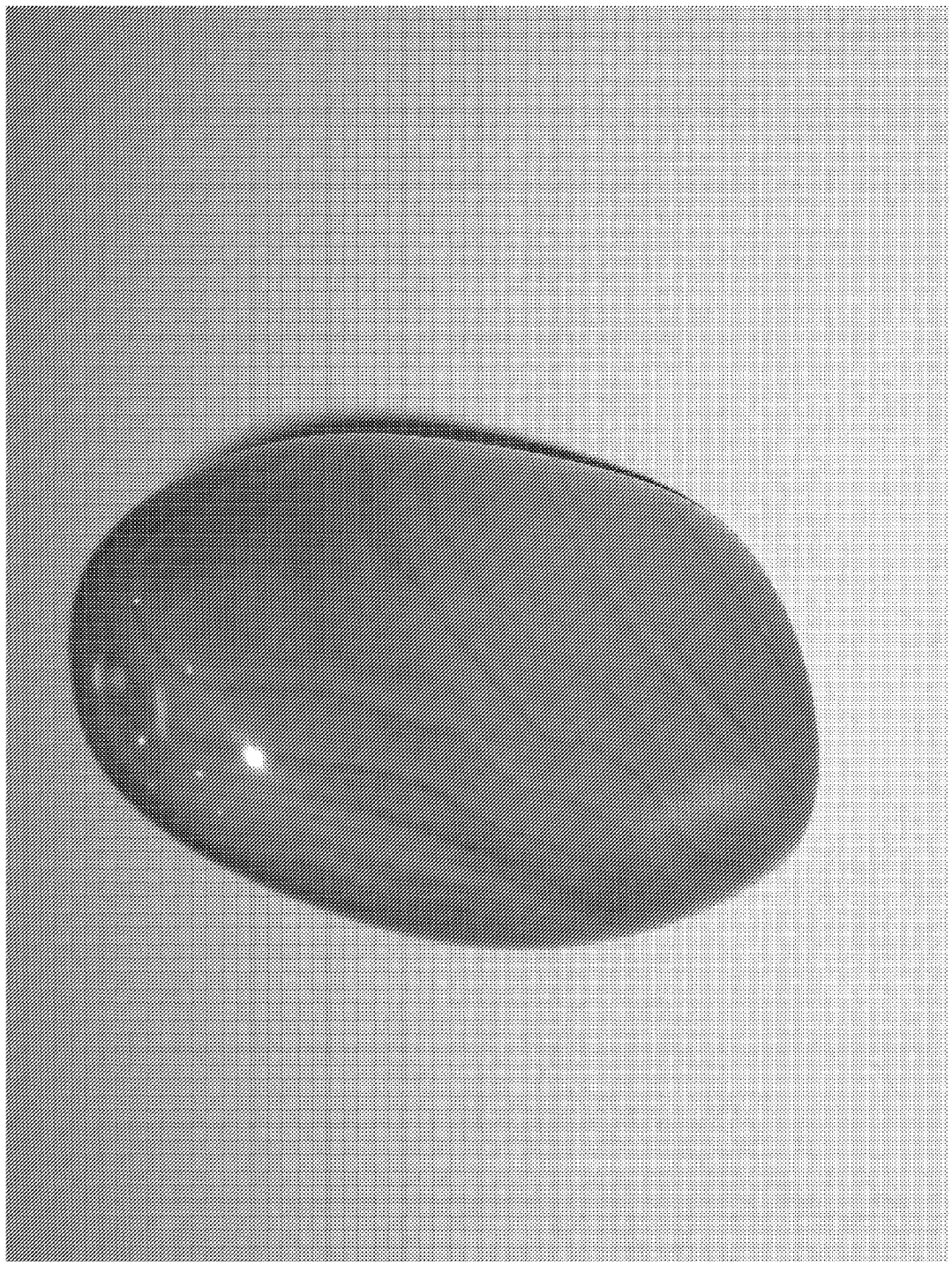
Figure 42:
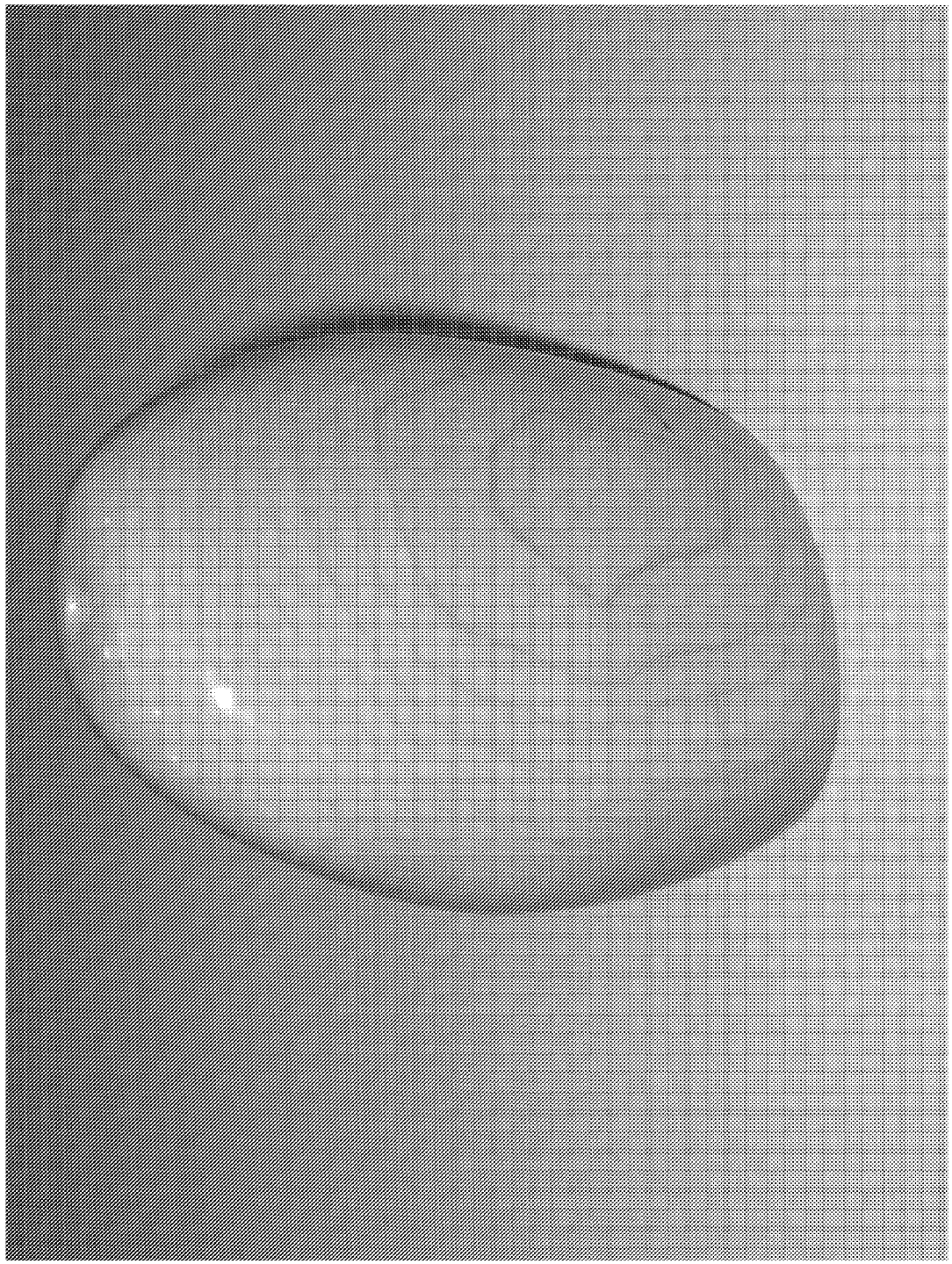
Figure 43:
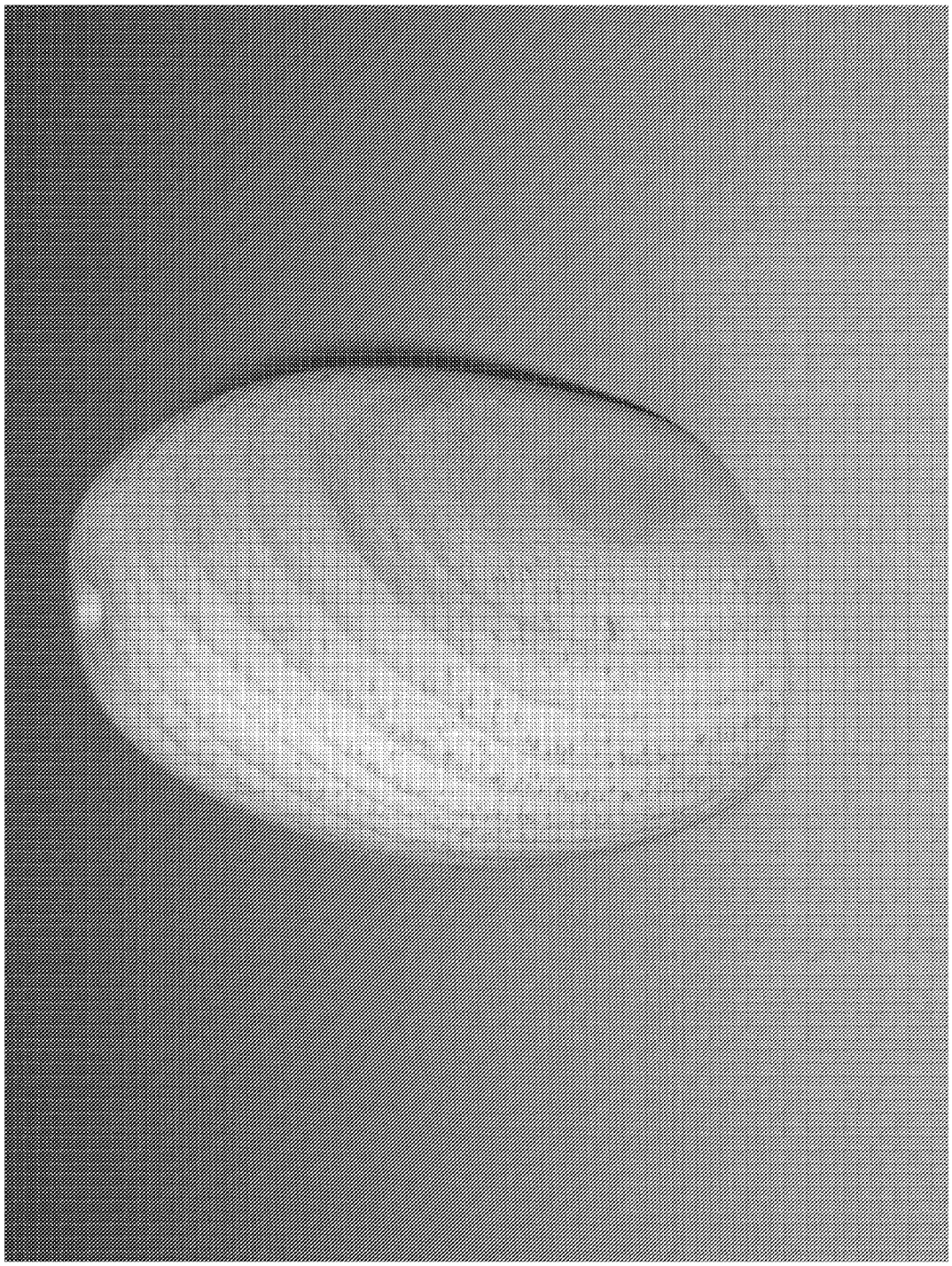
Figure 44:
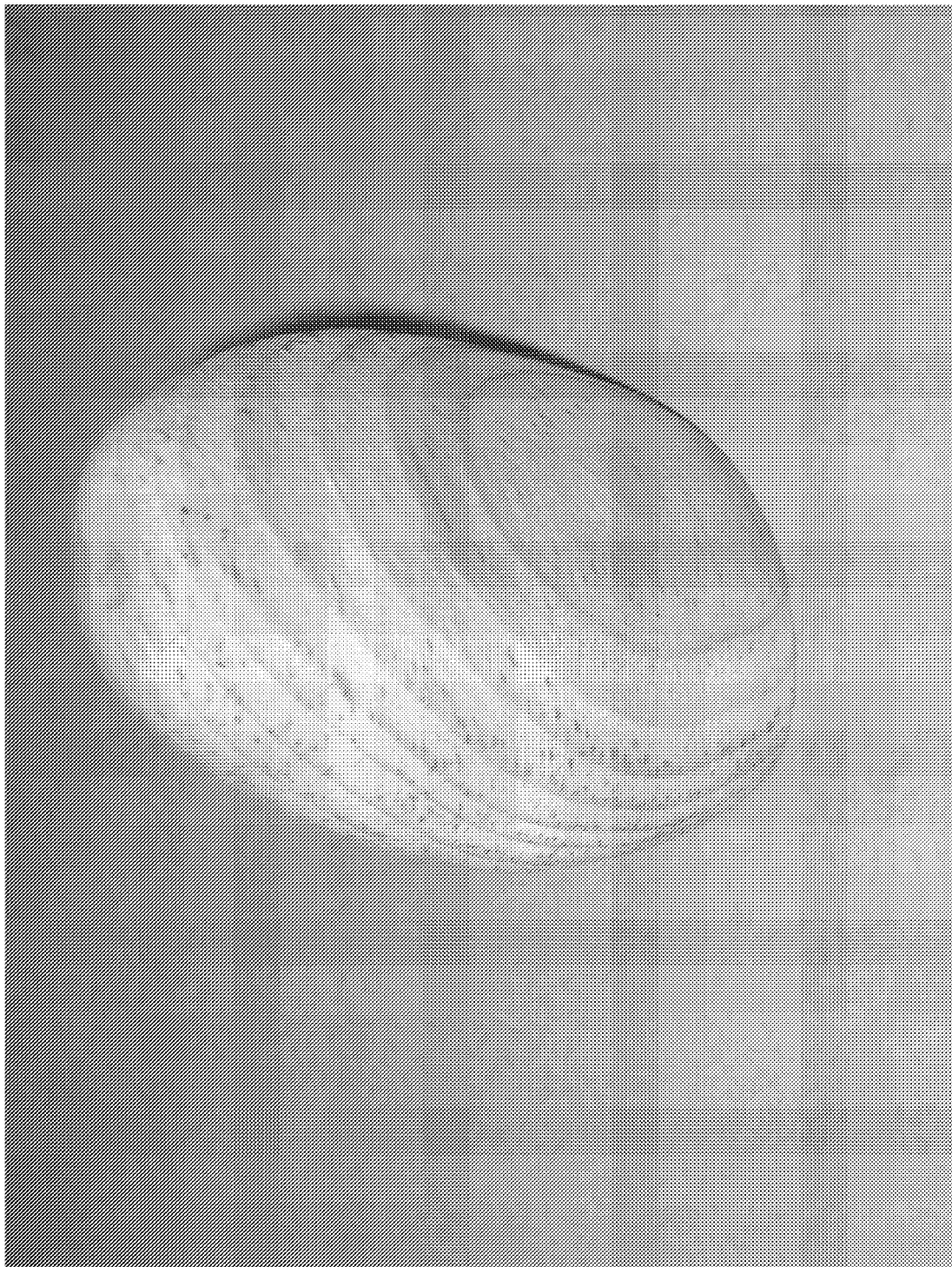
Figure 45:
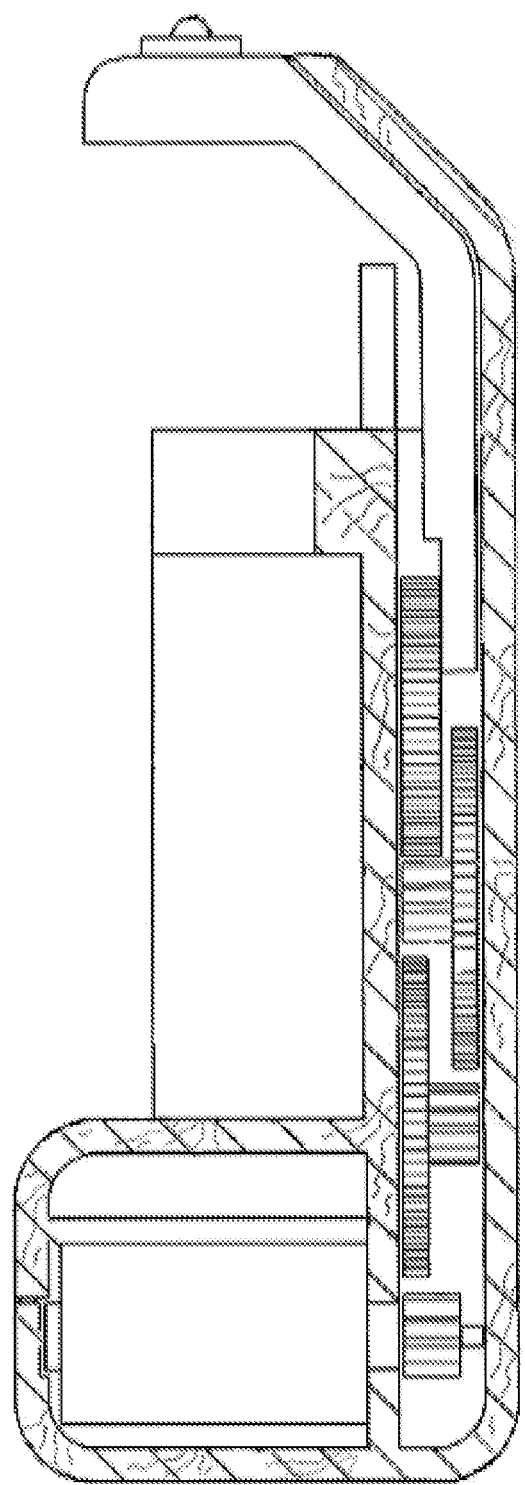
FIG. 45 is a cross-sectional view of another alternative dispenser utilizing an electro-mechanical drive unit, which is partially formed from a naturally occurring object.

It is also contemplated that other types of housings, e.g., telescopic housings or housings utilizing electronic elements, can similarly encompass the above-noted characteristics. For example, the electro-mechanical dispensing systems disclosed in U.S. patent application Ser. Nos. 11/725,402 and 11/893,532, which are incorporated herein by reference in their entirety, may be modified to include a natural look to give the impression that the dispenser does not fully or partially include any man-made features as noted above. For example, the dispenser could be fully or partially imparted with a natural looking pattern (see FIGS. 39 and 39A for an example of a cover that could be imparted with a natural looking pattern), mimic the shape of a naturally occurring object (see housings 72 and 77 of the previously disclosed embodiments), or be formed from a naturally occurring object (see FIGS. 40-44 depicting several housings similar to the ones noted herein formed from wood and FIG. 45 showing a different housing that is partially made from wood). However, it is also contemplated that other housings could be made from different materials such as pebbles, stones, fossilized articles, etc. Further, other mechanically operable dispensing systems such as the one described in U.S. Prov. App. No. 61/347,285, which is incorporated herein by reference in its entirety, may be similarly modified.

A further consideration for the consumer is the use of engagement mechanisms to ensure the proper operation of the dispenser. Various engagement mechanisms in the form of control mechanisms shown in FIGS. 46-74 may be used with any of the aerosol dispensers described hereinabove. Engagement mechanisms are helpful in ensuring that an improper container is not inserted into the dispenser. For example, if the dispenser is placed in a living room of a user's home he or she may inadvertently place a container of an aerosolized insecticide within the dispenser if a proper engagement mechanism is not provided. An engagement mechanism can also assist in preventing the mixture of different aerosolized products. For example, if a first aerosol is inadvertently replaced by a different second aerosol, residual components of the first aerosol still within the dispenser will mix with the components of the second aerosol. While various engagement mechanisms are known to those skilled in the art, the engagement mechanisms described in U.S. Pat. No. 6,830,164 and U.S. Pat. No. 6,978,914, which are herein incorporated by reference in their entirety, are of particular interest.

Figure 46:
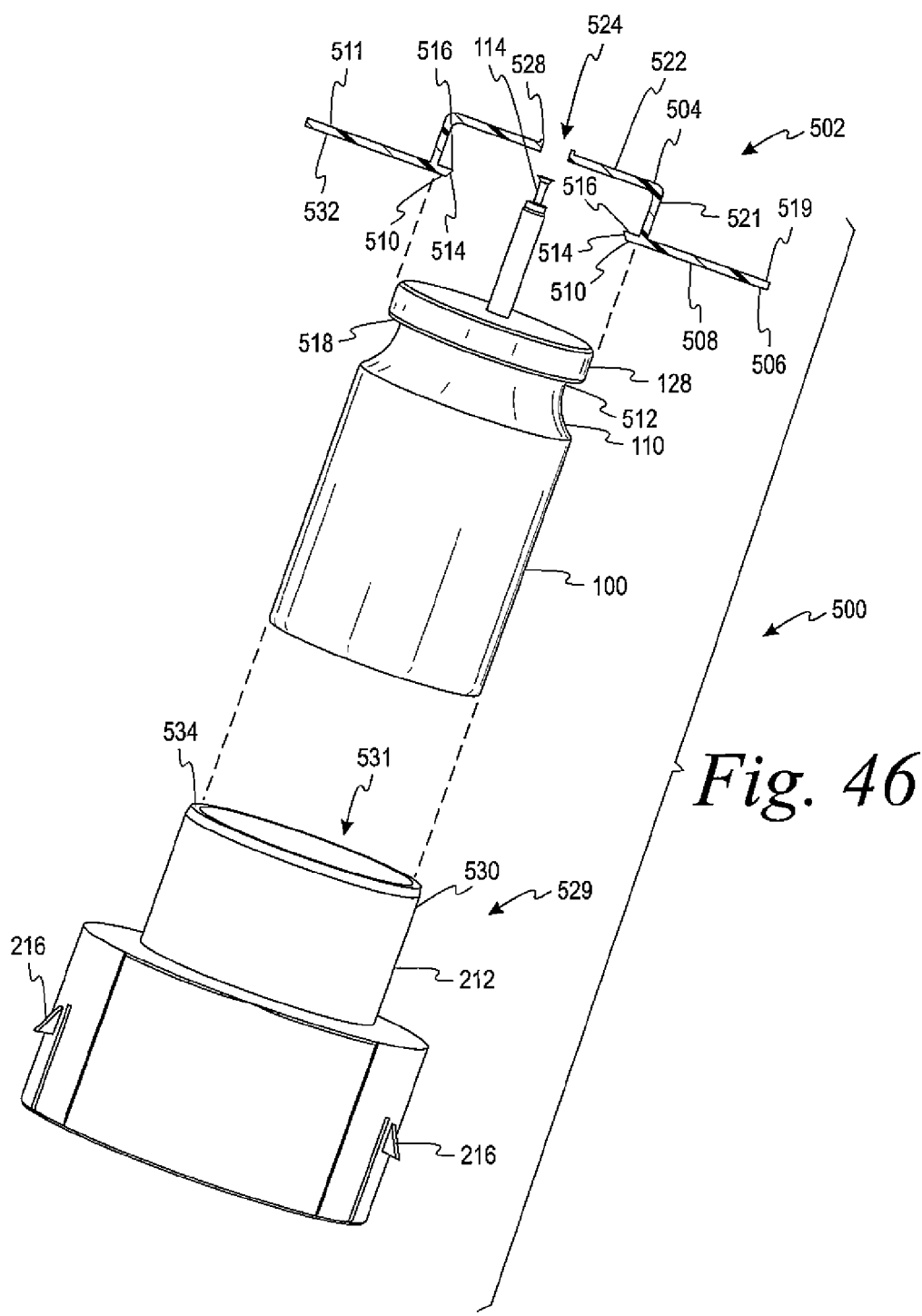
FIG. 46 is an exploded, partial sectional, isometric view of a first embodiment of an engagement mechanism including a container adapted to be inserted into a shroud and receive an adapter thereon.
Figure 47:
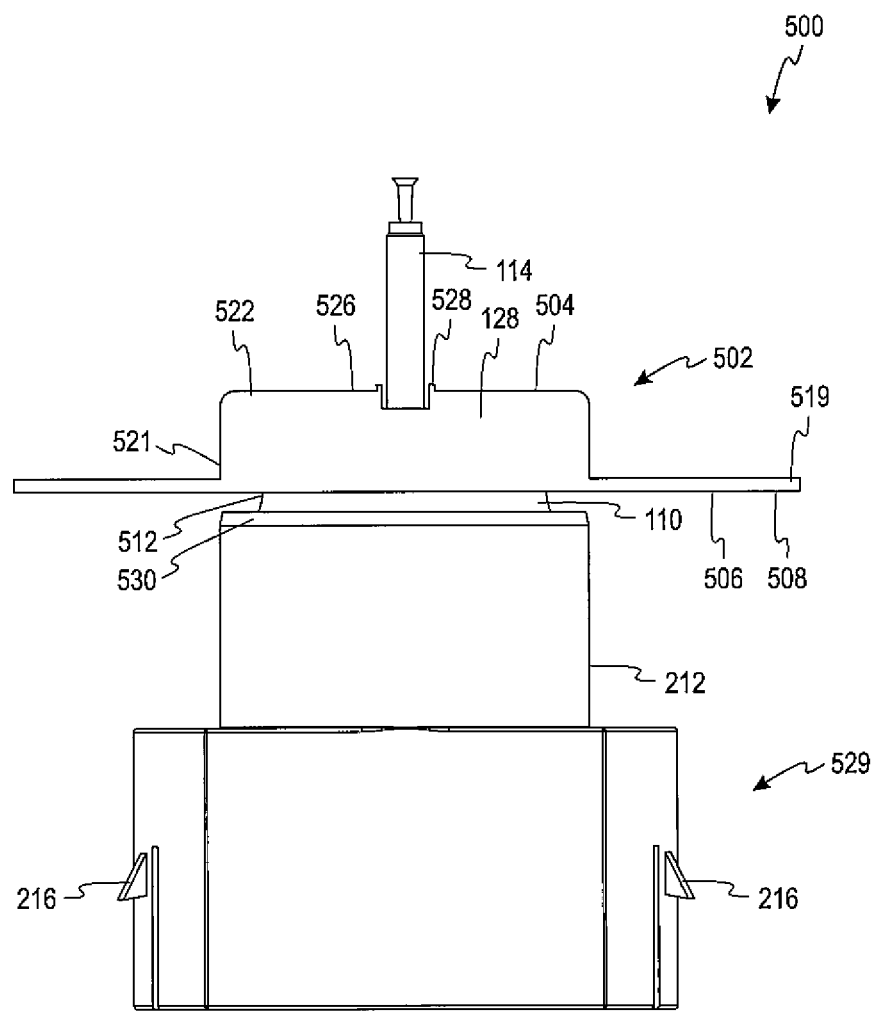
FIG. 47 is a front elevational view of the engagement mechanism of FIG. 46.
Figure 48:
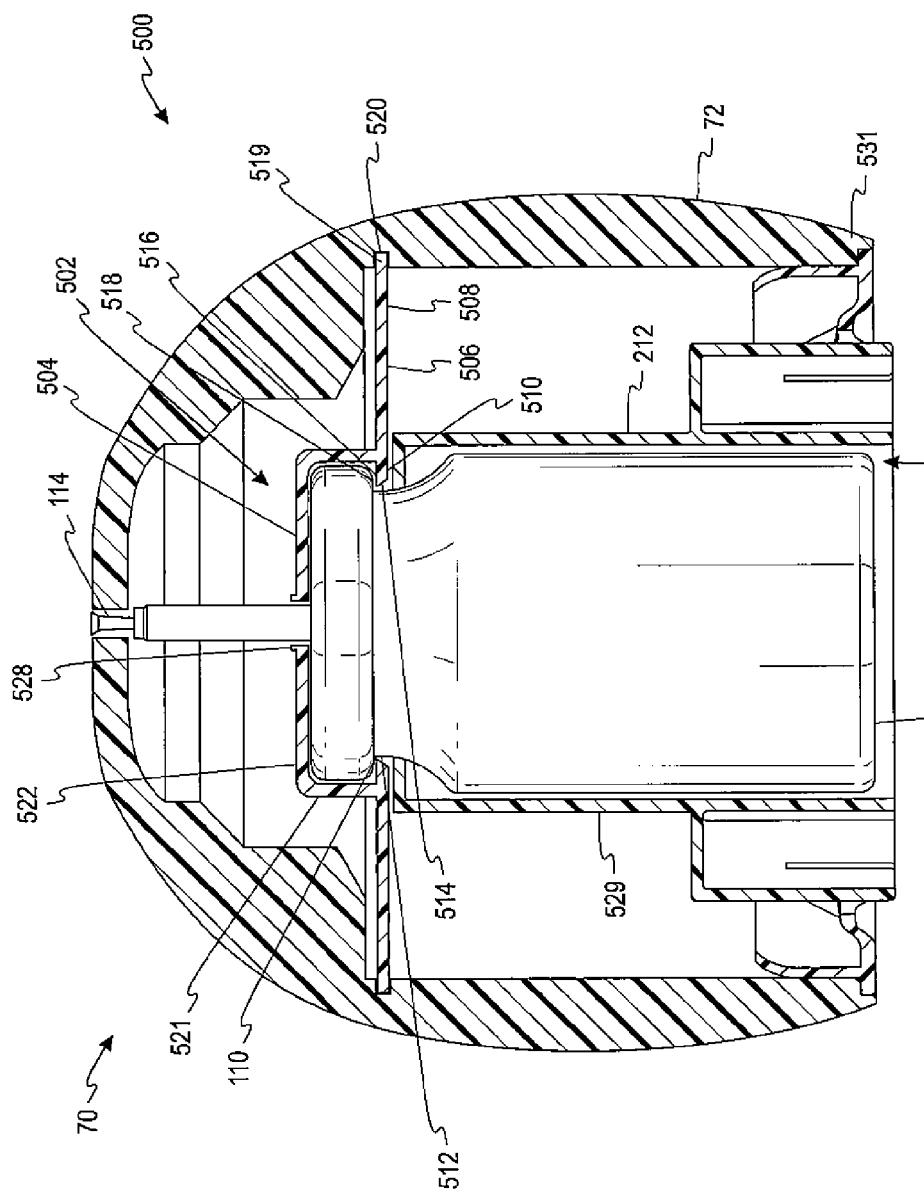
FIG. 48 is a partial sectional view of the engagement mechanism of FIG. 46 in combination with the housing of FIG. 1.

Referring to FIGS. 46-48, a control mechanism 500 includes a generally annular cap 502 having an upper portion 504 and a lower portion 506. The upper and lower portions 504, 506 are adapted to be fixedly connected to the neck 110 of the aerosol container 100 previously disclosed herein. The container 100 with the cap 502 is thereafter inserted into the housing 72 as previously disclosed herein.

The lower portion 506 of the cap 502 includes a collar 508 having an inwardly extending ledge 510, which is shaped to conform to a space 512 between the neck 110 and the mounting cup 128 of the aerosol container 100. As shown in FIG. 46, the ledge 510 tapers to a point 514 at an end thereof that includes a substantially flat top wall 516 adapted to interact with a lower surface 518 of the mounting cup 128. A rim 519 extends from an outside portion of the collar 508, which, in one embodiment, is adapted to interact with a corresponding groove 520 formed in the housing 72, shown in FIG. 48. A substantially vertical wall 521 joins the upper portion 504 and the lower portion 506 of the cap 502. The vertical wall 521 terminates at a substantially flat upper wall 522, which extends inwardly toward an aperture 524 provided in a central portion thereof. An upwardly extending wall 528 circumscribes the aperture 524. The aperture 524 is shaped to allow the valve stem 114 of the container 100 to extend therethrough. The actuator socket 300 discussed previously herein may or may not be used in conjunction with the cap 502. It is contemplated that the actuator socket 300 may include an interaction mechanism (not shown) to secure the actuator socket 300 to the cap 502 such that the container 100 is capable of being actuated.

Figure 15:
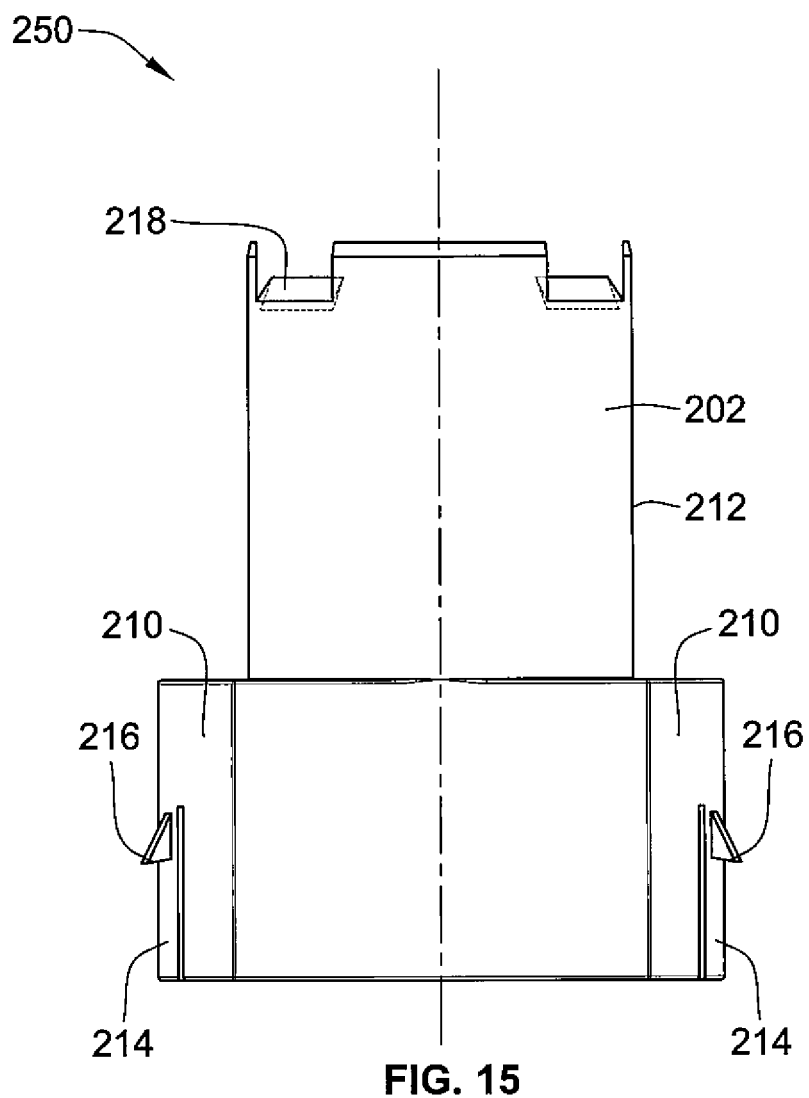
FIG. 15 is a side elevational view of a second embodiment of a shroud.

Still referring to FIGS. 46-48, the cap 502 is adapted to be used with the container 100 and a shroud 529. The shroud 529 is substantially similar to the shroud 250 described hereinabove with respect to FIG. 15, except that the shroud 529 does not include internal shoulders 218 (as shown in FIG. 15, for example), but rather has a substantially flat exterior surface 212. The internal shoulders 218 discussed with respect to previous embodiments allow the aerosol container 100 to snap into and be retained by the shroud 250. In contrast, the cap 502 is adapted to supply a surface that extends outwardly from the container 100 and physically interacts with the shroud 529. Without the shoulders 218, an aerosol container 100 without the cap 502 will not be retained by the shroud 529 and will slide downwardly out of the bottom of the shroud 529. The cap 502 may include a rim 519 having a length that extends any distance outwardly so long as the rim 519 is long enough to keep the container 100 retained within the shroud 529 as discussed further hereinbelow. The cap 502 may further include any type of protrusions and/or projections to matingly receive corresponding protrusions or projections from the container 100.

In use, the cap 502 is supplied with the aerosol container 100 and/or may be provided separately. If supplied separately, a user may slide the cap 502 onto the container 100 and secure the cap 502 thereto in any manner known in the art. As shown in FIG. 46, once the cap 502 is attached to the container 100, the container 100 is inserted downwardly from a top portion 530 of the shroud 529 into a central channel 531 thereof. The collar 508 interacts with an upper edge 534 of the shroud 529 to support the container 100 thereon. Thereafter, the actuator socket 300 may be attached (not shown) to the cap 502 to facilitate actuation. Referring to FIG. 48, the shroud 529 with the container 100 disposed therein is inserted upwardly through a bottom end 531 into a bore 533 of the housing 72. In one embodiment, at least a portion of the cap 502 is made of a somewhat flexible material to allow the cap 502 to flex as the container 100 and cap 502 traverse the bore 533. Once the cap 502 reaches the top of the housing 52, the rim 519 of the cap 502 extends outwardly into the groove 520 to secure the container 100 in the housing 52. At the same time, the shroud 529 attaches to the housing 52 in any manner previously disclosed herein.

In a different embodiment (not shown), a shorter length rim 519 is utilized that does not lock into the housing 72. In this embodiment, the rim 519 protrudes outwardly a sufficient distance to interact with the upper edge 534 of the shroud 529. However, the rim 519 does not lock into a groove in the housing 72. The container 100 and the shroud 529 of this embodiment are secured to the housing 72 using other methods described previously herein, e.g., the tapered protrusion 216, which could extend from the shroud 529.

Figure 49:
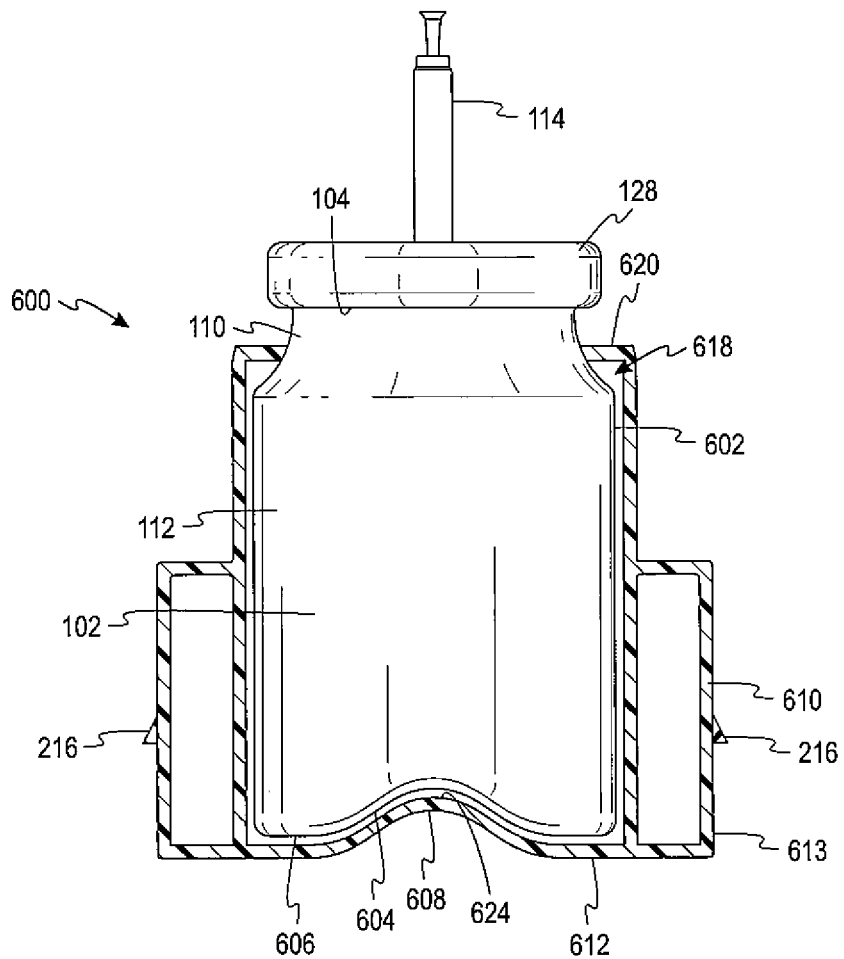
FIG. 49 is a partial sectional view of a different embodiment of an engagement mechanism including a shroud having a protrusion and a container with a recess.

Turning to FIG. 49, a second embodiment of a control mechanism 600 includes an aerosol container 602 with a curved recess 604 formed in a bottom surface 606 thereof. The recess 604 forms a curved depression that is adapted to interact with a corresponding curved protrusion 608 on a shroud 610. Alternatively, the recess 604 may be other shapes and sizes as known to one of skill in the art. The shroud 610 is substantially similar to the shroud 250 discussed hereinabove with respect to FIG. 15, except that the shroud 610 includes a bottom wall 612 that extends across the surface area defined by a bottom end 613 of the shroud 610. The protrusion 608 extends from a central portion of the bottom wall 612. The protrusion 608 is complementary to and is sized to extend into the recess 604 of the container 602. Although the protrusion 608 is depicted in a central location of the bottom wall 612, the protrusion 608 can be placed anywhere on the bottom wall 612 and may comprise any shape and size, e.g., the protrusion 608 could take the form of a rectangular ridge, an elongate flange, a triangular protuberance, etc. Further, in a different embodiment, a plurality of protrusions is used with a plurality of corresponding recesses. Still further, in a different embodiment, a protrusion extends outwardly from a bottom wall of the container 602 and interacts with a corresponding recess located in the bottom wall 612 of the shroud 610.

In use, the container 602 is inserted into a channel 618 formed in a top portion 620 of the shroud 610. As the container 602 slides downwardly through the channel 618 and reaches the bottom end 613 of the shroud 610, the recess 604 cooperates with the complementary protrusion 608 of the shroud 610. The shroud 610 and the container 602 are thereafter inserted into and secured to the housing 72 in a manner previously described herein. If a container without a recess 604 is inserted into the shroud 610, a bottom surface of the container will rest on a pinnacle 624 of the curved protrusion 608. Unauthorized containers without a recess will extend too far out of the shroud 610 and will be too large to fit into the housing (not shown).

Figure 50:
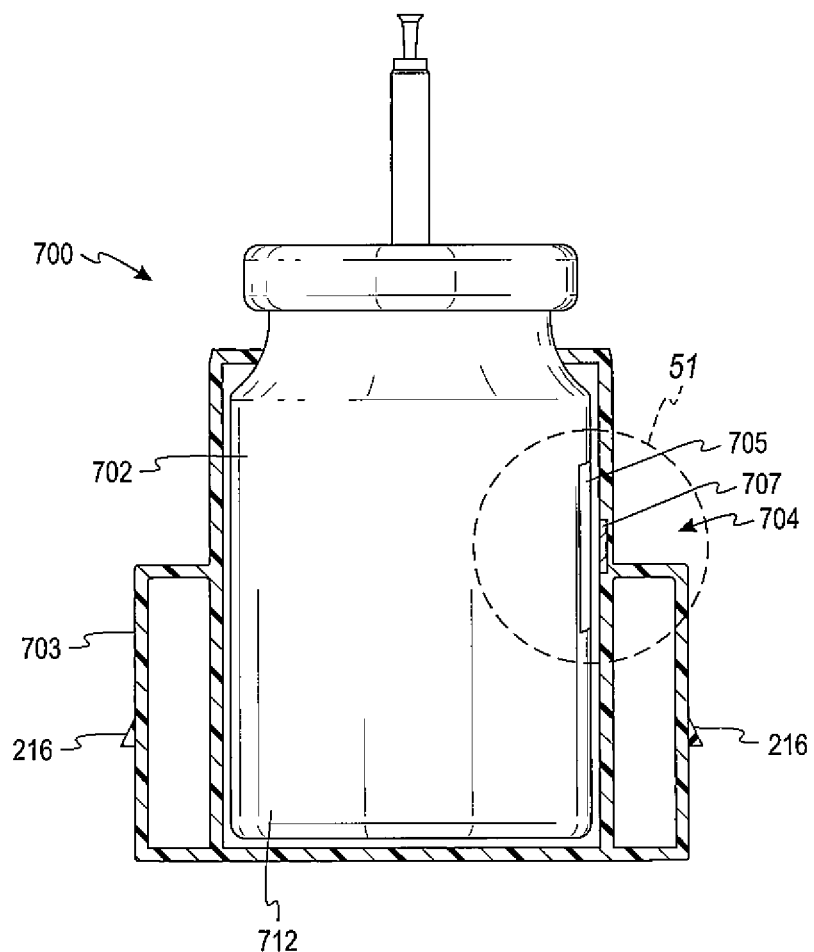
FIG. 50 is a partial sectional view of another embodiment of an engagement mechanism including a shroud and a container disposed therein with an electrical system.
Figure 51:
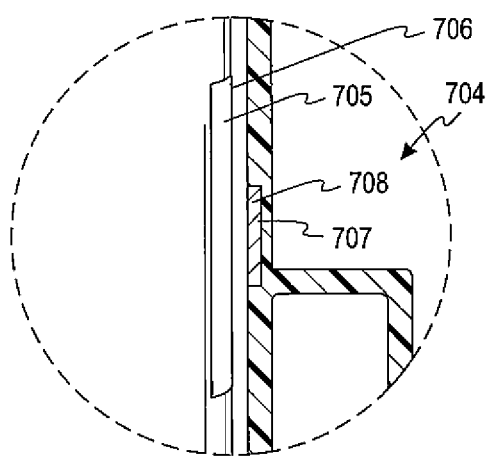
FIG. 51 is an enlarged sectional view of the electrical system of FIG. 50.

Referring to FIGS. 50 and 51, a third embodiment of a control mechanism 700 includes a container 702 and a shroud 703 with an electrical control system 704. The electrical control system 704 comprises a first component 705 and a second component 707 adapted to interact with each other and facilitate the operation of the dispenser. In one embodiment, the first component 705 is attached to the container 702 and the second component 707 is attached to the shroud 703. Alternatively, in a different embodiment, the first component 705 is attached to the container 702 and the second component 707 is attached to a housing (not shown). Any number of other combinations could be utilized as well. The shroud 703 and the housing may take the form of any of the embodiments disclosed herein. It is contemplated that the dispenser will only operate if the first and second components 705, 707 are compatible with one another.

In one embodiment, the first component 705 is supplied in the form of a magnet 706 and the second component 707 is supplied in the form of a micro reed switch 708. The magnet 706 is applied to the container 702 as a strip, a coating, an inlaid member, etc., in a position such as that shown in FIGS. 50 and 51. Alternatively, in a different embodiment, the magnet 706 is supplied in a bottom portion 712 of the container 702 (not shown). The magnet 706 is preferably supplied with the container 702 during the manufacturing and distribution process. In this embodiment, the micro reed switch 708 is attached to the shroud 703 or housing. The micro reed switch 708 is preferably attached to the shroud 703 or housing in a location that corresponds to the positioning of the magnet 706 in the container 702 such that the switch 708 is able to detect the presence of the magnet 706. The micro reed switch 708 is of the conventional kind known to one of skill in the art that is responsive to alternatively open and close when in the presence of a magnetic field. The micro reed switch 708 can be electrically connected to any conventional operating system known to one of skill in the art, e.g., a microcontroller, to facilitate the activation and deactivation thereof. For example, automated dispensers such as the ones disclosed in U.S. patent application Ser. No. 11/725,402, which is incorporated herein by reference in its entirety, could utilize any of the control mechanism embodiments disclosed herein. The positioning of the first component 705 in relation to the second component 707 depends on a number of factors including materials used, thickness of the walls of the individual components, strength properties of the components, and the like. Therefore, one having ordinary skill in the art can adjust the placement of the first and second components 705, 707, as desired.

In a different embodiment, the first component 705 may be any one of an optical light emitter, magnet, and the like, and the second component 707 is in the form of a sensor that is adapted to correspond and operate in response to the first component 705. For example, if a container 702 without an LED is inserted into the shroud 703 and/or housing that includes a light sensor, the dispenser will not activate. Alternatively, if the container 702 that includes the LED is inserted into the shroud 703 and/or housing that includes the sensor, the dispenser will activate.

Figure 52:
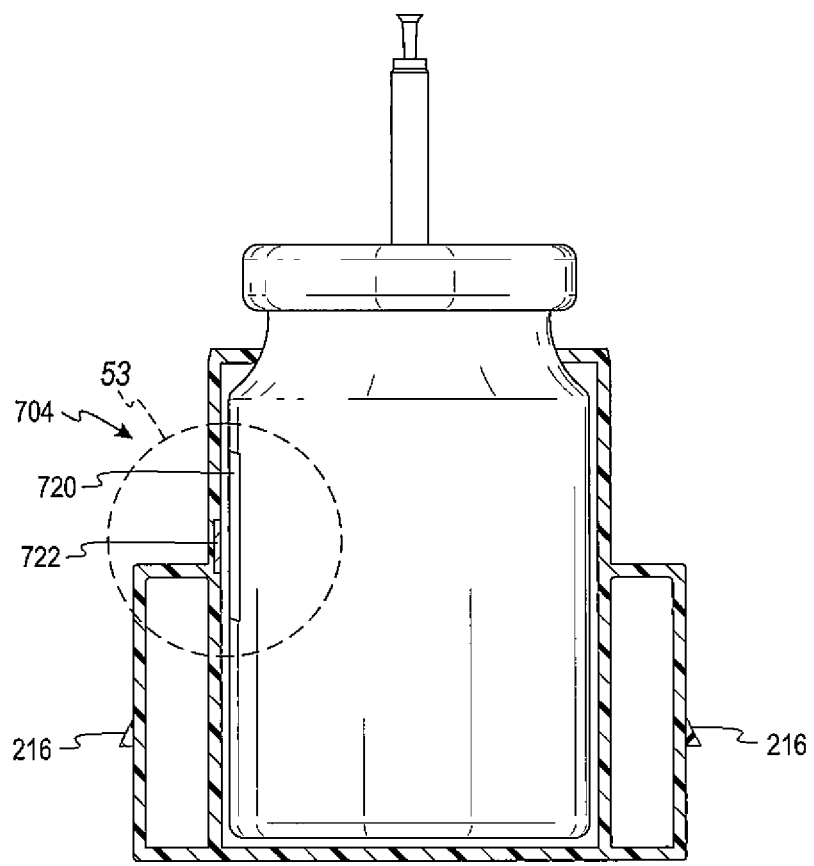
FIG. 52 is a partial sectional view of yet another embodiment of an engagement mechanism including a shroud and a container disposed therein with a different embodiment of an electrical system.
Figure 53:
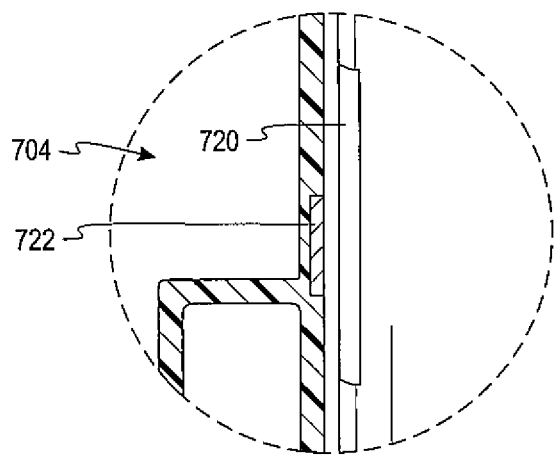
FIG. 53 is an enlarged sectional view of the electrical system of FIG. 52.

In a different embodiment shown in FIGS. 52 and 53, the electrical system 704 utilizes a conventional radio-frequency identification ("RFID") tag 720 in combination with an interrogator 722, such as those known by one of ordinary skill in the art. The RFID tag 720 and the interrogator 722 operate in a similar manner to the magnet 706 and reed switch 708 of the previous embodiment in that the dispenser will not operate if the interrogator 722 does not receive the appropriate signal from the RFID tag 720. Specifically, the RFID tag 720 is programmed to contain dispensing information, which is used to determine whether the dispenser should be activated. In other embodiments, the RFID tag 720 could contain information related to a specific dispensing sequence or to identify the source of fluid in the container to affect an appropriate dispensing response from the dispenser. It is also anticipated that other electrical control mechanisms disclosed herein may similarly control operative aspects of the dispenser.

In yet a different embodiment depicted in FIGS. 54 and 55, the first component 705 is disposed in the collar 508 of the annular adapter 502, which is discussed in connection with FIGS. 46-48. In one embodiment, the first component 705 is the magnet described in connection with FIGS. 50 and 51 and the second component 707 is a reed switch. The second component 707 is disposed within a wall 727 of the housing 72. Indeed, any of the control mechanisms discussed herein may be utilized in connection with this embodiment.

Figure 56:
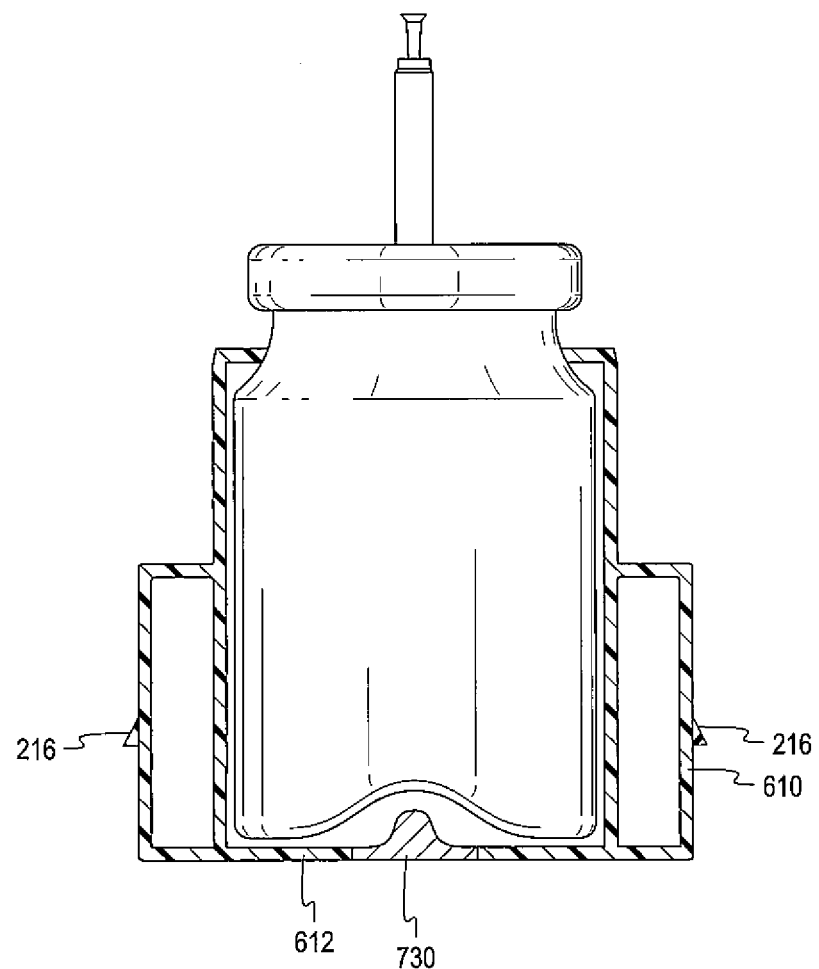
FIG. 56 is a partial sectional view of another embodiment of an engagement mechanism including a shroud and a container disposed therein.

In yet a different embodiment shown in FIG. 56, a sensor 730 is disposed in the bottom wall 612 of the shroud 610. The sensor 730 is adapted to respond to the presence or absence of a component within the container. For example, if the container depresses or otherwise deactivates the sensor 730, the sensor will not allow the operation of the container. Alternatively, if a container with a depression is inserted into the shroud 610, the sensor, which is electrically attached to a controller, will allow the operation thereof.

Figure 57:
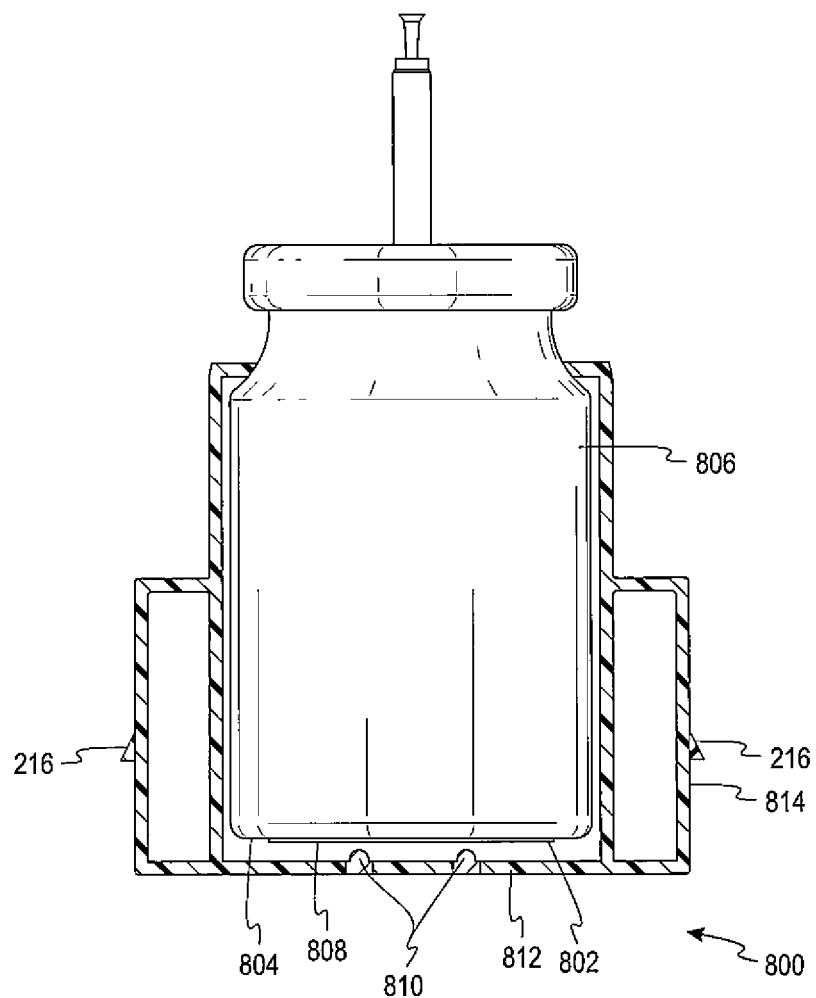
FIG. 57 is a partial sectional view of a different embodiment of an engagement mechanism including a shroud and a container having an insulator strip disposed thereon.

Turning to FIG. 57, a fourth embodiment of a control mechanism 800 includes an insulator 802 disposed on a bottom wall 804 of a container 806. The insulator 802 is in the form of a strip or sticker 808 that is applied to the wall 804. The sticker 808 can be applied using any method such as, for example, an adhesive. The insulator 802 is adapted to prevent electrical contacts 810 from touching the container 806. The electrical contacts 810 are disposed, for example, in a bottom wall 812 of shroud 814. The shroud 814 is similar to the shroud 610 discussed with respect to FIG. 49. Similar to other embodiments, the insulator 802 and corresponding contacts 810 may be disposed on any portion of the container 806 and shroud 814. In use, a forward or reverse sensing circuit (not shown) is associated with and electrically connected to the contacts 810. Thereafter, the presence or absence of a conductive material (such as the container wall) or insulative strip 802 will allow for the activation or deactivation of the circuit, which in turn allows for the operation of the dispenser.

Figure 58:
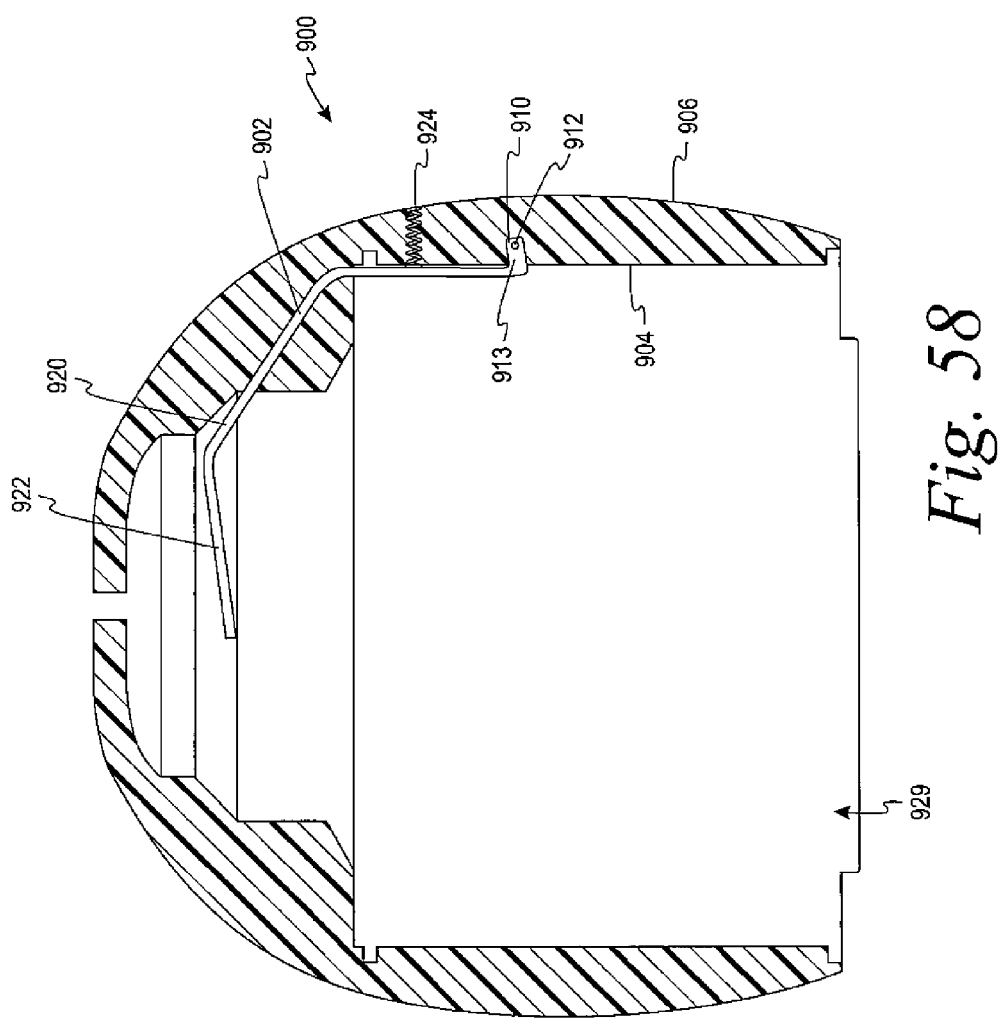
FIG. 58 is a partial sectional view of a different embodiment of an engagement mechanism including a housing having a blocker, wherein the blocker is in a first position.
Figure 60:
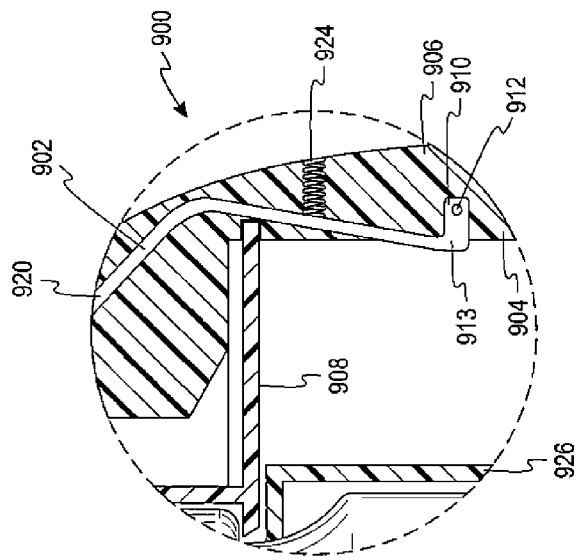
FIG. 60 is an enlarged partial sectional view of the embodiment of FIG. 59.
Figure 59:
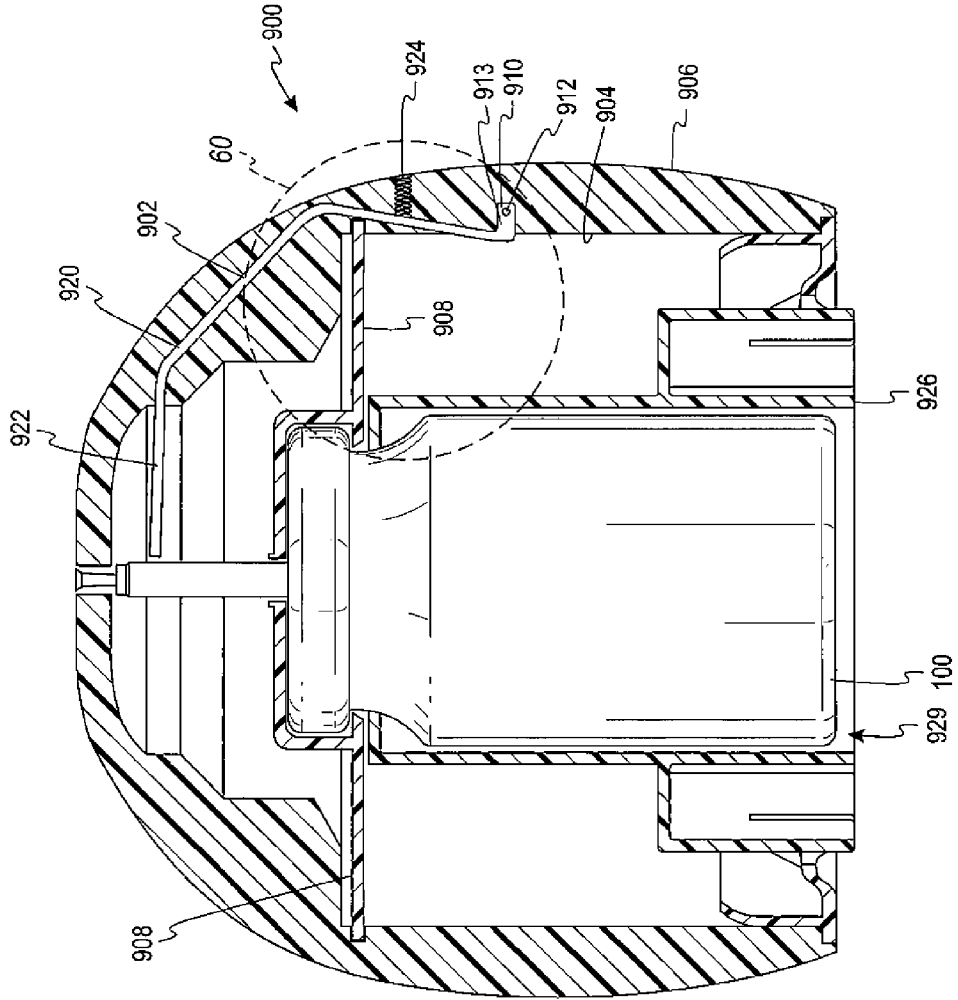
FIG. 59 is a partial sectional view of the embodiment of FIG. 58 including a housing having a blocker and a container with an adapter inserted therein, wherein the blocker is in a second position.

Referring to FIGS. 58-60, a fifth embodiment of a control mechanism 900 includes a blocker 902 that is attached to an inner wall 904 of a housing 906. The blocker 902 is adapted to be used in conjunction with the container 100, which includes a collar 908 similar to the collar 508 discussed in connection with FIGS. 46-48. The blocker 902 includes a connector section 910 disposed at a first end 913 thereof. The connector section 910 is adapted to be attached to the inner wall 904 of the housing 906. The connector section 910 may be attached in any manner, e.g., by using a pin 912 that extends through a void in the connector section 910. The pin 912 fits into catches that are attached to the inner wall 904 of the housing 906 on opposing sides of the connector section 910. Using a pin 912 and catches allows the blocker 902 to rotate from a first position to a second position. The blocker 902 further includes an upwardly extending wall 920 that terminates at a substantially flat wall 922, which extends outwardly away from the inner wall 904 of the housing 906. As best seen in FIG. 58, a spring 924 is disposed on the inner wall 904 of the housing 906 and is connected to the blocker 902. The spring 924 pushes the blocker 902 into the first, locked position (shown in FIG. 58) when a container 100 without a collar 908 or no container is disposed within the housing 906. The blocker 902 is adapted to cover the valve stem of the container and prevent insertion thereof if an unauthorized container is inserted into the housing 906.

In use, the approved container 100 is attached to a shroud 926 that is similar to the shroud 250 discussed with respect to previous embodiments. The container 100 and shroud 926 are inserted upwardly through a channel 929 in the housing 906. As the collar 908 makes contact with the blocker 902, the blocker 902 rotates about the pin 912 toward the inner wall 904 of the housing 906. Once the container 100 and the shroud 926 are fully inserted, the blocker 902 rests in the second, or unlocked position, which is depicted in FIGS. 59 and 60. Thereafter, the container 100 can be actuated in a similar manner as described hereinabove.

Figure 61:
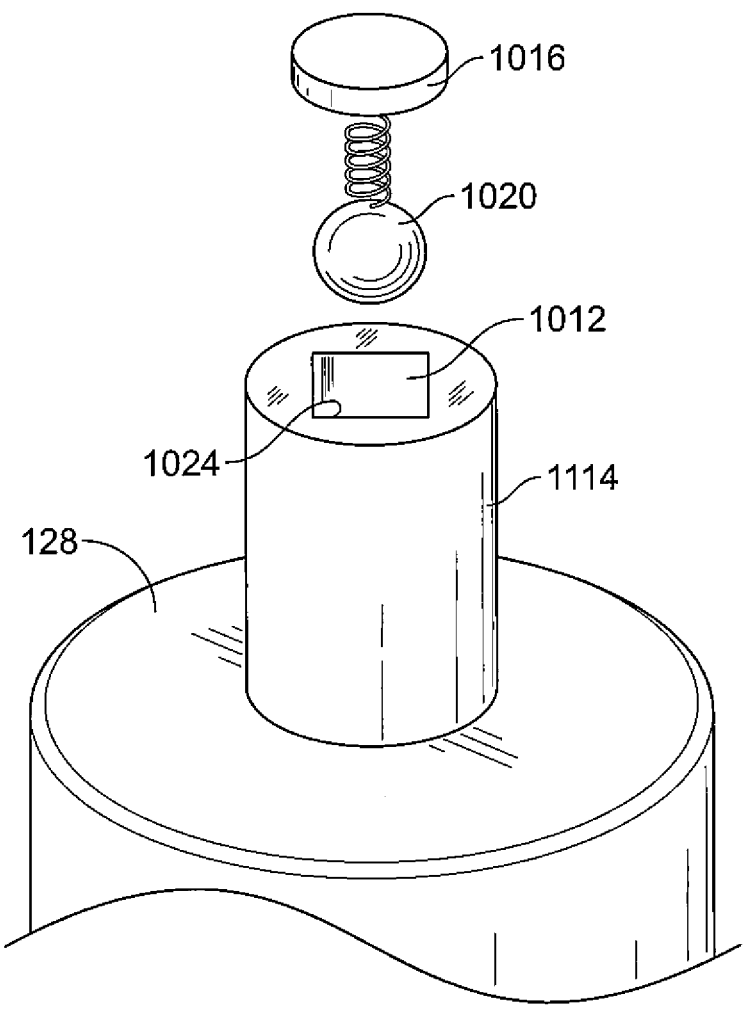
FIG. 61 is an enlarged isometric view of a valve stem.

Other engagement mechanisms may be utilized that are specific to any of the valve stems and/or actuator sockets 204, 300, as discussed herein. For example, FIG. 61 depicts the valve stem 1114 having a square axial passage 1012. An actuating element 1016 is provided that includes a spherical spring-biased ball 1020. When the ball 1020 and the valve stem 1114 are engaged during a dispensing sequence, the ball 1020 is at least partially disposed within the axial passage 1012. Fluid ejected through the valve stem 1114 may pass through one or more clearances 1024 provided about the periphery of the axial passage 1012. If a conventional cylindrical valve stem were to be engaged with the ball 1020, there would be no (or substantially no) clearance for the emission of the fluid. The square axial passage 1012 may be modified to take on any shape and/or size so long as the corresponding actuating element 1016 has a different shape and/or size to allow for clearance to exist therebetween.

Figure 62:
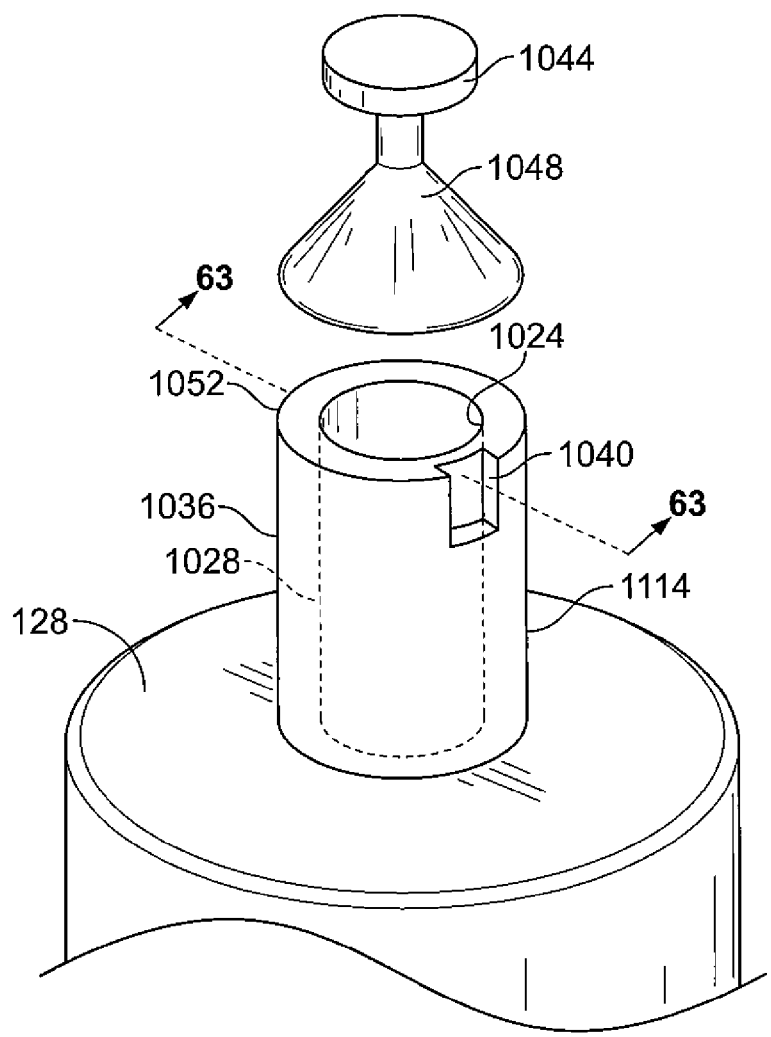
FIG. 62 is a view similar to FIG. 61 of another embodiment of an actuating element adjacent a valve element.
Figure 63:
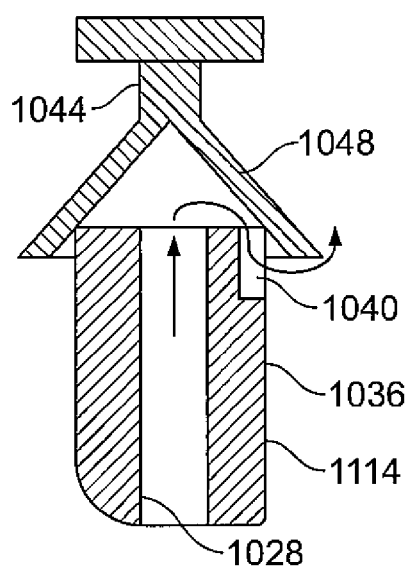
FIG. 63 is a sectional view taken generally along the lines 63-63 of FIG. 62 with the actuating element in engagement with the valve element.
Figure 64:
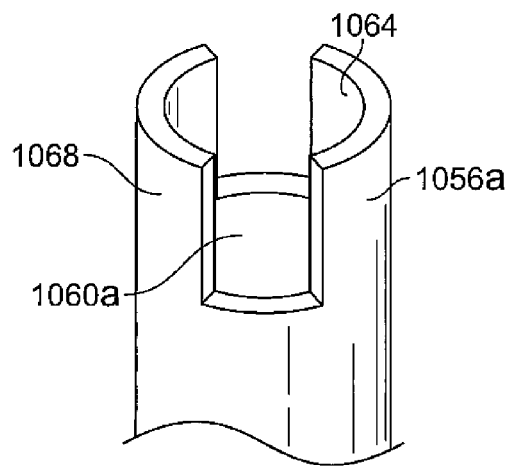
FIGS. 64-74 are enlarged isometric views of alternative valve stems that may be used in conjunction with the embodiments described herein.
Figure 65:
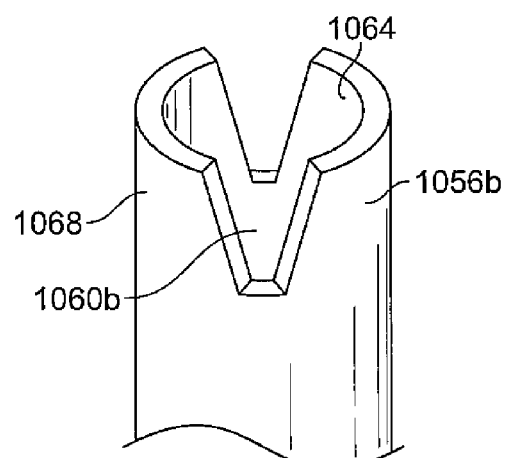
Figure 66:
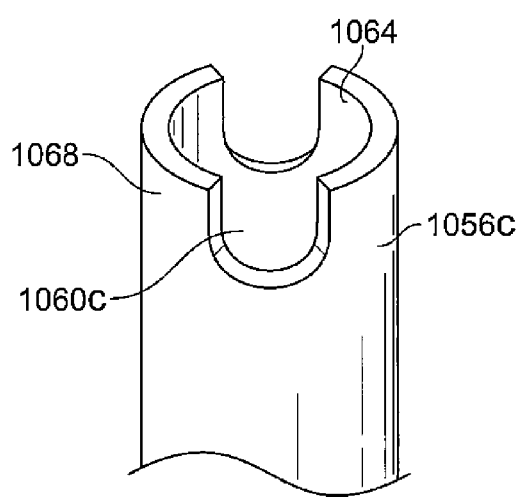
Figure 67:
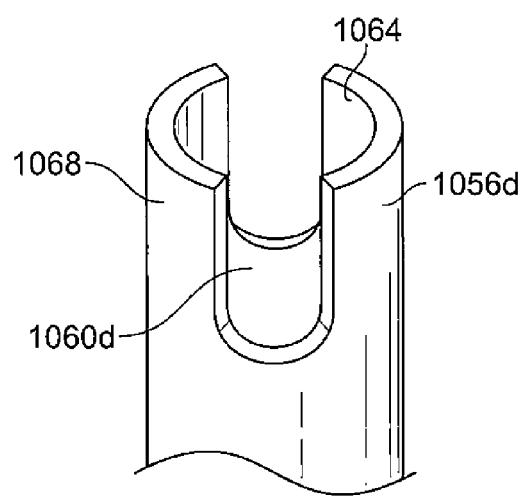
Figure 68:
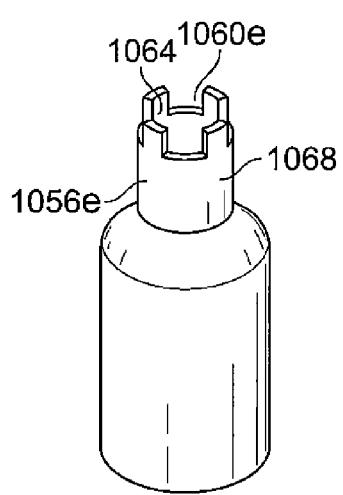
Figure 69:
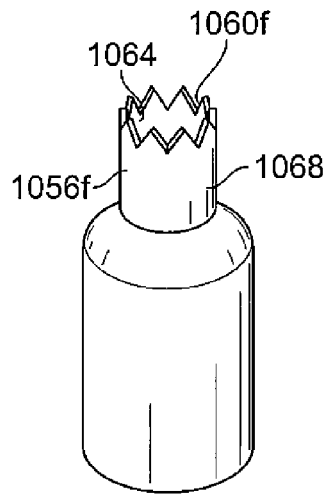
Figure 70:
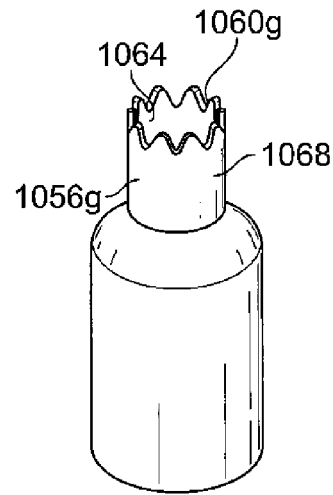
Figure 71:
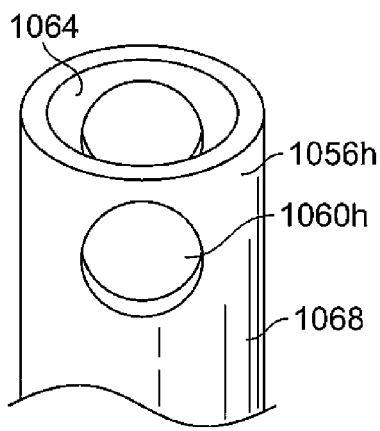
Figure 72:
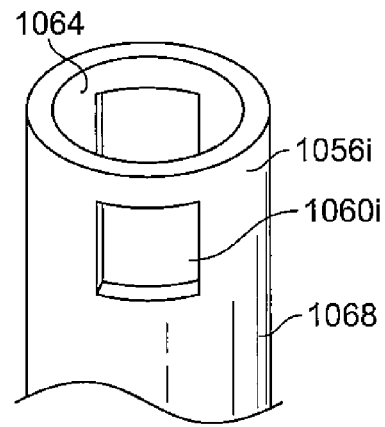
Figure 73:
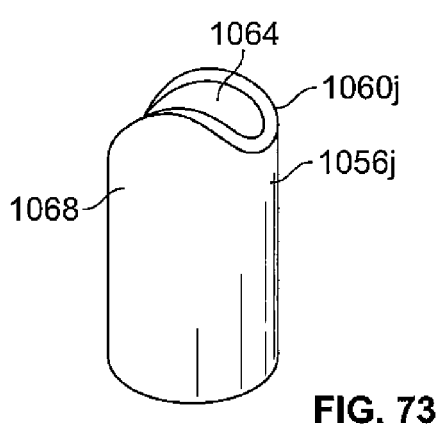
Figure 74:
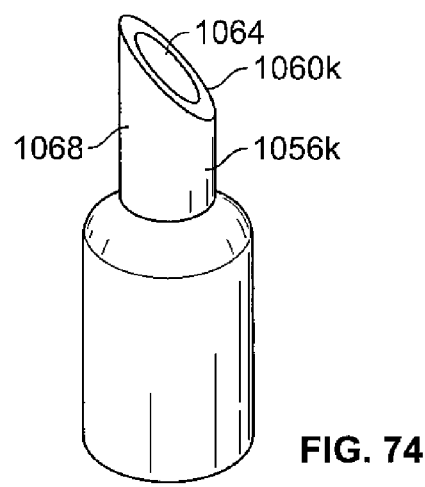

FIGS. 62 and 63 depict yet another embodiment of the valve element 1114 that includes an interior surface 1024 defining a first channel 1028 and an exterior surface 1036 that includes a second channel 1040 disposed therein. An actuating element 1044 includes a hollow engagement member 1048, which has a generally inverted frustoconical shape for sealing engagement with a peripheral surface 1052 of the valve stem 1114. When the valve element 1114 and the engagement member 1048 are engaged during a dispensing sequence, the fluid first flows in the direction of the arrow upwardly through the first channel 1028 and thereafter downwardly through the second channel 1040. If a conventional cylindrical valve stem is utilized with the present embodiment the fluid will be trapped within the engagement member 1048 and no (or substantially no) fluid will be discharged from the valve element 1114.

In a different embodiment, the valve element 1114 is modified to include the structure shown in any of FIGS. 64-74. All of the modified valve elements include exterior ends 1056a-k having reduced diameters and at least one side opening 1060a-k, respectively. The side openings 1060a-k extend from an interior axial chamber 1064 of the valve stem 1114 through an outer wall 1068 thereof. The various arrangements described above will prevent emission of the contents of a container, which does not include a valve stem with at least one side opening and a reduced diameter at an upper end thereof.

Any of the embodiments described herein may be modified to include any of the structures or methodologies disclosed in connection with different embodiments. Further, the present disclosure is not limited to the housings 72, 77 as specifically shown.

INDUSTRIAL APPLICABILITY

An aerosol dispenser may commonly be used to dispense a volatile material stored within an aerosol container. Commonly sold aerosol containers can include volatile materials such as air fresheners, deodorants, insecticides, germicides, decongestants, perfumes, and the like and can have a variety of lengths and/or widths. An aerosol dispenser is presented that can accommodate aerosol containers of different lengths and/or widths. Further, a dispenser is presented that has a variety of control mechanisms that prevent the use of unauthorized refills from being used therein.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

I claim:

1. A shroud, comprising:
a body portion for receipt in a dispenser having a first and a second opening for receipt of one of at least two different containers through the first and the second opening, wherein an upper portion of the body portion is adapted to retain one of the containers if inserted through the first or second opening.

2. The shroud of claim 1, wherein the body portion is substantially cylindrical.

3. The shroud of claim 1, wherein one of the at least two different containers is an aerosol container.

4. The shroud of claim 1, wherein one of the at least two different containers is fittingly received through the first opening.

5. The shroud of claim 4, wherein one of the at least two different containers is fittingly received through an upper end of the body portion.

6. The shroud of claim 4, wherein one of the at least two different containers is fittingly received through a lower end of the body portion.

7. The shroud of claim 4, wherein one of the at least two different containers includes a cap portion disposed on an upper portion thereof.

8. The shroud of claim 1, wherein the first opening is adapted to receive both a container with a cap portion and a container without a cap portion.

9. The shroud of claim 1 further including at least one flexible internal shoulder at the upper portion of the body portion for engaging a portion of a container.

10. The shroud of claim 9, wherein four flexible internal shoulders are provided for engaging a mounting cup of a container.

11. The shroud of claim 1 further including a plurality of notches in the upper portion of the body portion, wherein first and third opposing towers are provided having a first height and second and fourth opposing towers are provided having a second height less than the first height.

12. The shroud of claim 11, wherein the first through fourth towers include angled portions provided on upper ends thereof with substantially flat terminal portions thereabove.

13. The shroud of claim 12, wherein a container is fittingly received through the second opening and at least the angled portions and the substantially flat terminal portions of the first and third towers are resiliently received beneath a mounting cup of the container.

14. A shroud, comprising:
a body portion having an upper portion truncated by a plurality of notches, wherein first and third independent opposing towers are provided having a first height and second and fourth independent opposing towers are provided having a second height less than the first height;
a skirt extending downwardly and outwardly from the body portion; and
an opening extending through the body portion and the skirt adapted to receive a container.

15. The shroud of claim 14, wherein the body portion is substantially cylindrical.

16. The shroud of claim 14, wherein the first through fourth towers include angled portions provided on upper ends thereof with substantially flat terminal portions thereabove.

17. The shroud of claim 14, wherein the skirt is substantially oval shaped.

18. The shroud of claim 14, wherein the skirt is defined by a sidewall having opposing first and second ends and opposing first and second medial portions.

19. The shroud of claim 18 further including a flat surface extending outwardly from a bottom portion of the body portion toward a top ridge of the sidewall.

20. The shroud of claim 18, wherein the skirt further includes opposing first and second finger tabs provided within the first and second ends, respectively.

21. The shroud of claim 20, wherein the skirt further includes two elongate vertical openings within the first end and two elongate vertical openings within the second end.

22. The shroud of claim 20, wherein the skirt further includes a plurality of tapered protrusions extending outwardly from the first and second finger tabs.

23. The shroud of claim 14, wherein a plurality of oval-shaped tabs extend outwardly from a bottom edge of the skirt.

24. The shroud of claim 14, wherein a container is fittingly received through the opening.

25. The shroud of claim 24, wherein the container is fittingly received through an upper end of the body portion.

26. The shroud of claim 24, wherein the container is fittingly received through a lower end of the skirt.

27. The shroud of claim 24, wherein the container includes a cap portion disposed on upper portions thereof.

28. The shroud of claim 24, wherein the opening is adapted to receive both a container with a cap portion and a container without a cap portion.

29. The shroud of claim 16, wherein a container is fittingly received through the opening and at least the angled portions and substantially flat terminal portions of the first and third towers are resiliently received beneath a mounting cup of the container.

* * * * *